United States Patent
Gotoh et al.

(10) Patent No.: US 10,584,284 B2
(45) Date of Patent: Mar. 10, 2020

(54) ANTIOXIDANT HAVING DIFLUOROMETHOXY GROUP, LIQUID CRYSTAL COMPOSITION, AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Gotoh, Tokyo (JP); Teizi Satou, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/934,155

(22) Filed: Nov. 6, 2015

(65) Prior Publication Data

US 2016/0130501 A1 May 12, 2016

(30) Foreign Application Priority Data

Nov. 10, 2014 (JP) ................. 2014-228125

(51) Int. Cl.
- *C07C 43/23* (2006.01)
- *C09K 19/54* (2006.01)
- *C07C 69/75* (2006.01)
- *C07C 69/94* (2006.01)
- *C09K 19/20* (2006.01)
- *C09K 19/30* (2006.01)
- *C09K 19/32* (2006.01)
- *C09K 19/04* (2006.01)
- *C09K 19/34* (2006.01)

(52) U.S. Cl.
CPC .............. *C09K 19/54* (2013.01); *C07C 43/23* (2013.01); *C07C 69/75* (2013.01); *C07C 69/94* (2013.01); *C09K 19/20* (2013.01); *C09K 19/3066* (2013.01); *C09K 19/32* (2013.01); *C09K 19/322* (2013.01); C07C 2601/14 (2017.05); C09K 2019/0448 (2013.01); C09K 2019/0466 (2013.01); C09K 2019/3425 (2013.01)

(58) Field of Classification Search
None
See application file for complete search history.

(56) References Cited

U.S. PATENT DOCUMENTS

| | | |
|---|---|---|
| 6,444,278 B1 | 9/2002 | Reiffenrath et al. |
| 2002/0066888 A1* | 6/2002 | Shibata ................... C07C 17/16 252/299.61 |

FOREIGN PATENT DOCUMENTS

| | | |
|---|---|---|
| EP | 2808376 | 12/2014 |
| JP | 09-124529 | 5/1997 |
| JP | 2002-256267 | 9/2002 |
| JP | 2003160525 A * | 6/2003 |
| JP | 2010-180266 | 8/2010 |
| WO | 2014/162587 | 10/2014 |

OTHER PUBLICATIONS

English Translation of JP200316525.*

* cited by examiner

*Primary Examiner* — Cynthia H Kelly
*Assistant Examiner* — Anna Malloy
(74) *Attorney, Agent, or Firm* — JCIPRNET

(57) ABSTRACT

A compound represented by formula (1), a liquid crystal composition to which the compound is added, and a liquid crystal display device containing the composition.

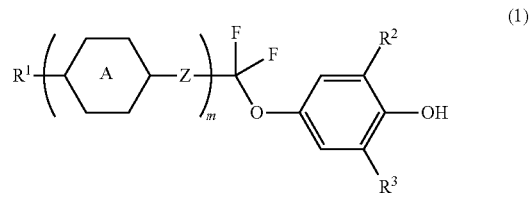

In formula (1), $R^1$ is hydrogen or alkyl having 1 to 20 carbons, or the like; $R^2$ and $R^3$ are independently methyl, ethyl, isopropyl, or t-butyl; ring A is 1,4-cyclohexylene, 1,4-phenylene or the like; Z is a single bond or alkylene having 1 to 6 carbons, or the like; and m is 0, 1, or 2.

10 Claims, No Drawings ered. The stability of
the composition to ultraviolet light and heat relates to
service life of the liquid crystal display device. When the
stability is high, the device has long service life. Such
characteristics are preferred in an AM device for use in
liquid crystal projectors and liquid crystal TVs, etc. A large
elastic constant in the composition contributes to a large
contrast ratio and short response time in the device. Therefore, a large elastic constant is preferred.
ANTIOXIDANT HAVING DIFLUOROMETHOXY GROUP, LIQUID CRYSTAL COMPOSITION, AND LIQUID CRYSTAL DISPLAY DEVICE

CROSS-REFERENCE TO RELATED APPLICATION

This application claims the priority benefit of Japan application serial no. 2014-228125, filed on Nov. 10, 2014. The entirety of the above-mentioned patent application is hereby incorporated by reference herein and made a part of this specification.

FIELD OF THE INVENTION

The invention relates to a phenol-based antioxidant, a liquid crystal composition, and a liquid crystal display device. More specifically, the invention relates to a 2,6-dialkyl-4-substituted phenol, a liquid crystal composition to which the compound is added, and a liquid crystal display device containing the composition.

DESCRIPTION OF THE RELATED ART

For liquid crystal display devices, a classification based on an operating mode of liquid crystals includes phase change (PC), twisted nematic (TN), super twisted nematic (STN), electrically controlled birefringence (ECB), optically compensated bend (OCB), in-plane switching (IPS), vertical alignment (VA), fringe field switching (FFS), polymer sustained alignment (PSA), and field induced photo-reactive alignment (FPA) modes, etc. A classification based on a driving mode of the device includes passive matrix (PM) and active matrix (AM). The PM type is classified into static type and multiplex type, etc.; the AM type is classified into thin-film transistor (TFT) type and metal insulator metal (MIM) type, etc. The TFT type is classified into amorphous silicon and polycrystal silicon. The latter is classified into a high temperature type and a low temperature type according to a production process. A classification based on a light source includes a reflective type utilizing natural light, a transmissive type utilizing backlight, and a transflective type utilizing both natural light and backlight.

These devices contain a liquid crystal composition having suitable characteristics. The liquid crystal composition has a nematic phase. General characteristics of the composition can be improved to obtain an AM device having good general characteristics. The following Table 1 summarizes a relationship of the general characteristics between two aspects. The general characteristics of the composition are further described based on a commercially available AM device. A temperature range of the nematic phase relates to a temperature range in which the device can be used. A preferred maximum temperature of the nematic phase is about 70° C. or higher, and a preferred minimum temperature of the nematic phase is about −10° C. or lower. Viscosity of the composition relates to response time of the device. Short response time is preferred for displaying moving images on the device. Accordingly, small viscosity in the composition is preferred, and small viscosity at low temperature is more preferred. An elastic constant of the composition relates to contrast of the device. A large elastic constant in the composition is more preferred for increasing the contrast in the device.

TABLE 1

General Characteristics of Composition and AM Device

| No | General characteristics of composition | General characteristics of AM device |
|---|---|---|
| 1 | Wide temperature range of a nematic phase | Wide usable temperature range |
| 2 | Small viscosity[1] | Short response time |
| 3 | Suitable optical anisotropy | Large contrast ratio |
| 4 | Large positive or negative dielectric anisotropy | Low threshold voltage; small electric power consumption Large contrast ratio |
| 5 | Large specific resistance | Large voltage holding ratio; large contrast ratio |
| 6 | High stability to ultraviolet light and heat | Long service life |
| 7 | Large elastic constant | Large contrast ratio; short response time |

[1]The time for pouring the composition into a liquid crystal cell can be shortened.

Optical anisotropy of the composition relates to the contrast ratio of the device. A product (Δn×d) of the optical anisotropy (Δn) of the composition and a cell gap (d) of the device is designed so as to maximize the contrast ratio. A suitable value of the product depends on the type of the operating mode. In a device in a mode such as TN, the suitable value is about 0.45 μm. In a device in the VA mode, the suitable value is in the range of about 0.30 to 0.40 μm; in a device in the IPS or FFS mode, the suitable value is in the range of about 0.20 to 0.30 μm. In this case, a composition having large optical anisotropy is preferred for a device having a small cell gap. A large absolute value of dielectric anisotropy in the composition contributes to a low threshold voltage, small electric power consumption and a large contrast ratio in the device. Accordingly, a large absolute value of dielectric anisotropy is preferred. Large specific resistance in the composition contributes to a large voltage holding ratio and a large contrast ratio in the device. Accordingly, a composition having large specific resistance not only at room temperature but also at a temperature close to the maximum temperature of the nematic phase at an early stage is preferred. A composition having large specific resistance not only at room temperature but also at a temperature close to the maximum temperature of the nematic phase after a long-time use is preferred. The stability of the composition to ultraviolet light and heat relates to service life of the liquid crystal display device. When the stability is high, the device has long service life. Such characteristics are preferred in an AM device for use in liquid crystal projectors and liquid crystal TVs, etc. A large elastic constant in the composition contributes to a large contrast ratio and short response time in the device. Therefore, a large elastic constant is preferred.

In order to prepare a composition having such characteristics, the type and ratio of a liquid crystal compound as a component are carefully selected. However, such characteristics sometimes cannot be maintained for a long time. Display defects may occur in the device due to aging. The reason is presumably that the liquid crystal compound is oxidized. For preventing the oxidation, an antioxidant is added to the composition. Examples of the antioxidant include 2,6-di-t-butyl-4-methylphenol (Patent Documents 1 and 2), a compound (BH7) (Patent Document 3) and a compound (BH3L) (Patent Document 4), but a more useful antioxidant is needed. It is expected that an antioxidant that has low vapor pressure and high solubility to the composition and that is effective even in a small amount can be developed.

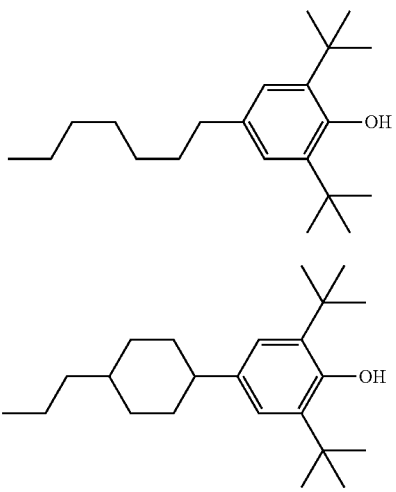

(BH7)

(BH3L)

PRIOR-ART DOCUMENTS

Patent Documents

[Patent Document 1] JP 2002-256267

[Patent Document 2] JP 2010-180266

[Patent Document 3] WO 2014/162587

[Patent Document 4] JP H09-124529

SUMMARY OF THE INVENTION

Problems to be Solved by the Invention

One object of the invention is a compound useful as an antioxidant. Other objects include a liquid crystal composition that contains the compound and satisfies at least one of characteristics such as high maximum temperature of a nematic phase, low minimum temperature of a nematic phase, small viscosity, suitable optical anisotropy, large positive or negative dielectric anisotropy, large specific resistance, high stability to ultraviolet light, high stability to heat, and a large elastic constant, etc. Other objects include a liquid crystal composition that achieves a suitable balance between at least two of these characteristics. Other objects include a liquid crystal display device that contains such a composition and has characteristics such as short response time, a large voltage holding ratio, a low threshold voltage, a large contrast ratio, and long service life, etc. Other objects include a liquid crystal composition that has high stability to ultraviolet light, and a device that hardly undergoes a decrease in voltage holding ratio even after a long-time use.

Means for Solving the Problems

The invention relates to a compound represented by formula (1), a liquid crystal composition to which the compound is added, and a liquid crystal display device containing the composition.

In formula (1), $R^1$ is hydrogen or alkyl having 1 to 20 carbons, wherein at least one —$CH_2$— in the alkyl is optionally replaced with —O—, —S—, —CO—, or —$SiH_2$—, and at least one —$CH_2CH_2$— in the alkyl is optionally replaced with —CH=CH— or —C≡C—; $R^2$ and $R^3$ are independently methyl, ethyl, isopropyl, or t-butyl; ring A is 1,4-cyclohexylene, 1,4-cyclohexenylene, decahydronaphthalene-2,6-diyl, 1,2,3,4-tetrahydronaphthalene-2,6-diyl, 1,4-phenylene, or naphthalene-2,6-diyl, wherein at least one —$CH_2$— in these groups is optionally replaced with —O—, —S—, —CO—, or —$SiH_2$—, at least one —$CH_2CH_2$— in these groups is optionally replaced with —CH=CH— or —CH=N—, and at least one hydrogen in these divalent groups is optionally replaced with fluorine, chlorine, —C≡N, —$CF_3$, —$CHF_2$, —$CH_2F$, —$OCF_3$, —$OCHF_2$, or —$OCH_2F$; Z is a single bond or alkylene having 1 to 6 carbons, wherein at least one —$CH_2$— in the alkylene is optionally replaced with —O—, —S—, —CO—, or —$SiH_2$—, one or two —$CH_2CH_2$— in the alkylene are optionally replaced with —CH=CH— or —C≡C—, and at least one hydrogen in these divalent groups is optionally replaced with fluorine or chlorine; and m is 0, 1, or 2, wherein when m=2, two rings A may be the same or different, and two Z's may be the same or different.

Effects of the Invention

One advantage of the invention is a compound that has low vapor pressure and high solubility and that is useful as an antioxidant. Other advantages include a liquid crystal composition that contains the compound and satisfies at least one of characteristics such as high maximum temperature of a nematic phase, low minimum temperature of a nematic phase, small viscosity, suitable optical anisotropy, large positive or negative dielectric anisotropy, large specific resistance, high stability to ultraviolet light, high stability to heat, and a large elastic constant, etc. Other advantages include a liquid crystal composition that achieves a suitable balance between at least two of these characteristics. Other advantages include a liquid crystal display device that contains such a composition and has characteristics such as short response time, a large voltage holding ratio, a low threshold voltage, a large contrast ratio, and long service life, etc. Other advantages include a liquid crystal composition that has high stability to ultraviolet light, and a device that hardly undergoes a decrease in voltage holding ratio even after a long-time use.

DESCRIPTION OF THE EMBODIMENTS

The terms in this specification are defined as follows. "Liquid crystal composition" and "liquid crystal display device" are sometimes simply referred to as "composition" and "device," respectively. "Liquid crystal display device" is a generic term for liquid crystal display panels and liquid crystal display modules. "Liquid crystal compound" means a compound having a liquid crystal phase such as nematic phase or smectic phase etc., or a compound having no liquid crystal phase but being useful as a component of a composition. This compound has, e.g., a six-membered ring such as 1,4-cyclohexylene or 1,4-phenylene, and a rod-like molecular structure. "Polymerizable compound" is a compound that is added for producing a polymer in the composition. At least one compound selected from the group consisting of compounds represented by formula (1) is sometimes simply referred to as "compound (1)." "Compound (1)" means one compound represented by formula (1), a mixture of two compounds represented by formula (1), or a mixture of three or more compounds represented by formula (1). The same rule applies to the compounds represented by other formulae.

A liquid crystal composition is prepared by mixing a plurality of liquid crystal compounds. The ratio (content) of the liquid crystal compound is expressed by a weight percentage (wt %) based on the weight of the liquid crystal composition. Additives such as a polymerizable compound, a polymerization initiator, a polymerization inhibitor, an optically active compound, an antioxidant, an ultraviolet absorbent, a light stabilizer, a heat stabilizer, a dye and a defoamer are added to the liquid crystal composition if necessary. Similarly to the liquid crystal compound, a ratio (amount added) of the additive is expressed by a weight percentage (wt %) based on the weight of the liquid crystal composition. Parts per million (ppm) may also be used. A ratio of the polymerization initiator or polymerization inhibitor is exceptionally expressed based on the weight of the polymerizable compound.

The maximum temperature of a nematic phase is sometimes simply referred to as "maximum temperature." The minimum temperature of a nematic phase is sometimes simply referred to as "minimum temperature." "Having large specific resistance" means that the composition has large specific resistance not only at room temperature but also at a temperature close to the maximum temperature of the nematic phase at an early stage, and that the composition has large specific resistance not only at room temperature but also at a temperature close to the maximum temperature of the nematic phase after a long-time use. "Having a large voltage holding ratio" means that the device has a large voltage holding ratio not only at room temperature but also at a temperature close to the maximum temperature of the nematic phase at an early stage, and the device has a large voltage holding ratio not only at room temperature but also at a temperature close to the maximum temperature of the nematic phase after a long-time use. The expression "increase the dielectric anisotropy" means that when the composition has positive dielectric anisotropy, the value of the dielectric anisotropy increases positively, and that when the composition has negative dielectric anisotropy, the value of the dielectric anisotropy increases negatively. "Stabilize the liquid crystal composition" means that to improve stability of the liquid crystal composition with respect to ultraviolet light or heat.

A symbol $R^1$ is used for a plurality of compounds in chemical formulae of component compounds. In arbitrary two of these compounds, groups to be selected by $R^1$ may be the same or different. For example, in one case, $R^1$ represents ethyl in both compounds (1-1-a) and (1-1-b). In another case, $R^1$ represents ethyl in the compound (1-1-a), and represents propyl in the compound (1-1-b). This rule also applies to symbols such as $R^2$, $R^{11}$, $Z^{11}$ and so on. In a compound (8), when i is 2, two rings $D^1$ are present. In this compound, the two groups represented by the two rings $D^1$ may be the same or different. When i is greater than 2, the same rule also applies to arbitrary two rings $D^1$. This rule also applies to symbols such as ring A, Z, $Z^{17}$ and so on. Symbols A, $B^1$, $C^1$ and so on that are surrounded by hexagons respectively correspond to ring A, ring B, ring C and so on. In the compound (1), a hexagon represents a six-membered ring such as benzene ring, or a fused ring such as naphthalene ring. In compounds (2) to (15), a hexagon represents a six-membered ring such as benzene ring.

The expression "at least one 'A'" means the number of 'A' is arbitrary. The expression "at least one 'A' is optionally replaced with 'B'" means that when the number of 'A' is one, the position of 'A' is arbitrary, and when the number of 'A' is two or more, the positions thereof can be selected without limitation. This rule also applies to the expression "at least one 'A' is replaced with 'B'." The expression "at least one A is optionally replaced with B, C or D" means that at least one A is replaced with B, at least one A is replaced with C or at least one A is replaced with D, and also means that a plurality of A's are replaced with at least two of B, C and D. For example, the scope of "alkyl in which at least one —$CH_2$— (or —$CH_2$—$CH_2$—) is optionally replaced with —O— (or —CH=CH—)" includes alkyl, alkenyl, alkoxy, alkoxyalkyl, alkoxyalkenyl and alkenyloxyalkyl. Moreover, it is undesirable that two successive —$CH_2$— be replaced with —O— to form —O—O—, and it is also undesirable that —$CH_2$— in a methyl moiety (—$CH_2$—H) in alkyl or the like be replaced with —O— to form —O—H.

Halogen includes fluorine, chlorine, bromine and iodine. The halogen is preferably fluorine or chlorine. The halogen is more preferably fluorine. Alkyl is straight or branched, and does not include cyclic alkyl. Generally, straight alkyl is preferred to branched alkyl. The same rules also apply to terminal groups such as alkoxy and alkenyl, etc. Generally, the stereo configuration of 1,4-cyclohexylene is preferably trans rather than cis. 2-fluoro-1,4-phenylene means the following two divalent groups. In a chemical formula, fluorine may be leftward (L) or rightward (R). This rule also applies to an asymmetrical divalent group derived by removing two hydrogens from a ring, such as tetrahydropyran-2,5-diyl.

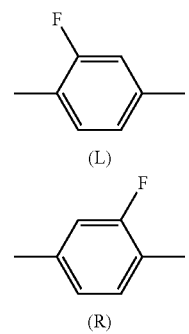

The invention includes the following items.
Item 1 is a compound represented by formula (1).

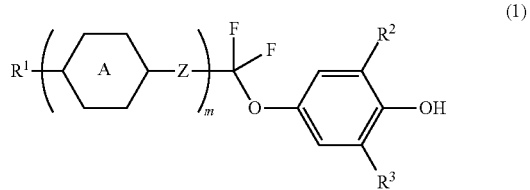

In formula (1), $R^1$ is hydrogen or alkyl having 1 to 20 carbons, wherein at least one —$CH_2$— in the alkyl is optionally replaced with —O—, —S—, —CO—, or —$SiH_2$—, and at least one —$CH_2CH_2$— in the alkyl is optionally replaced with —CH=CH— or —C≡C—; $R^2$ and $R^3$ are independently methyl, ethyl, isopropyl, or t-butyl; ring A is 1,4-cyclohexylene, 1,4-cyclohexenylene, decahydronaphthalene-2,6-diyl, 1,2,3,4-tetrahydronaphthalene-2,6-diyl, 1,4-phenylene, or naphthalene-2,6-diyl, wherein at least one —$CH_2$— in these groups is optionally replaced with —O—, —S—, —CO—, or —$SiH_2$—, at least one —$CH_2CH_2$— in these groups is optionally replaced with —CH=CH— or —CH=N—, and at least one hydrogen in these divalent groups is optionally replaced with fluorine, chlorine, —C≡N, —$CF_3$, —$CHF_2$, —$CH_2F$, —$OCF_3$, —$OCHF_2$, or —$OCH_2F$; Z is a single bond or alkylene having 1 to 6 carbons, wherein at least one —$CH_2$— in the alkylene is optionally replaced with —O—, —S—, —CO—, or —$SiH_2$—, one or two —$CH_2CH_2$— in the alkylene are optionally replaced with —CH=CH— or and at least one hydrogen in these divalent groups is optionally replaced with fluorine or chlorine; and m is 0, 1, or 2, wherein when m=2, two rings A may be the same or different, and two Z's may be the same or different.

Item 2 is the compound according to item 1, wherein in formula (1) described in item 1, $R^1$ is hydrogen or alkyl having 1 to 20 carbons, wherein at least one —$CH_2$— in the alkyl is optionally replaced with —O— or —S—; $R^2$ and $R^3$ are independently methyl, ethyl, isopropyl, or t-butyl; ring A is 1,4-cyclohexylene, 1,4-cyclohexenylene, tetrahydropyran-2,5-diyl, 1,4-phenylene, or 1,4-phenylene in which at least one hydrogen is replaced with fluorine or chlorine; Z is a single bond, —$CH_2CH_2$—, —CH=CH—, —C≡C—, —COO—, —OCO—, —$CH_2O$—, —$OCH_2$—, —CF=CF—, —$CF_2CF_2$—, —$CH_2CF_2$—, —$CH_2CHF$—, —$CH_2S$—, or —$SCH_2$—; and m is 0, 1, or 2, wherein when m=2, two rings A may be the same or different, and two Z's may be the same or different.

Item 3 is the compound according to item 1 or 2, wherein in formula (1) described in item 1, $R^1$ is alkyl having 2 to 20 carbons; $R^2$ and $R^3$ are independently methyl, ethyl, isopropyl, or t-butyl; ring A is 1,4-cyclohexylene, 1,4-phenylene, or 1,4-phenylene in which at least one hydrogen is replaced with fluorine; Z is a single bond, —$CH_2CH_2$—, —CH=CH—, —C≡C—, —COO—, —OCO—, —$CH_2O$—, or —$OCH_2$—; and m is 1 or 2, wherein when m=2, two rings A may be the same or different, and two Z's may be the same or different.

Item 4 is the compound according to any one of items 1 to 3, represented by formulae (1-1-a) to (1-1-e).

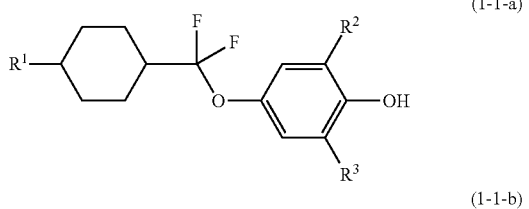
(1-1-a)

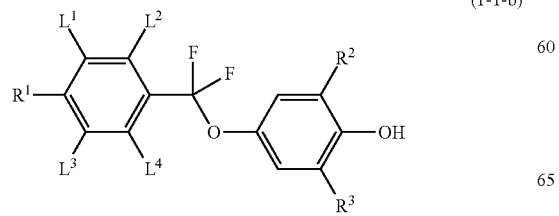
(1-1-b)

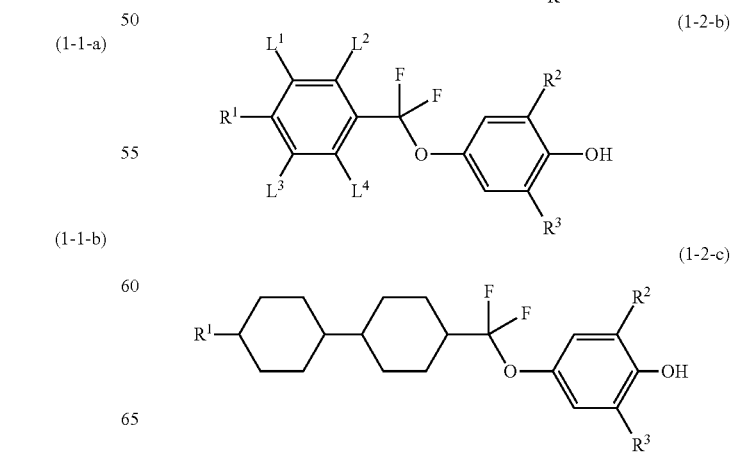
(1-1-c)

(1-1-d)

(1-1-e)

In formulae (1-1-a) to (1-1-e), $R^1$ is alkyl having 2 to 20 carbons; $R^2$ and $R^3$ are independently methyl, ethyl, isopropyl, or t-butyl; Z is a single bond, —$CH_2CH_2$—, —CH=CH—, —C≡C—, —COO—, —OCO—, —$CH_2O$—, or —$OCH_2$—; and $L^1$, $L^2$, $L^3$, $L^4$, $L^5$, $L^6$, $L^7$, and $L^8$ are independently hydrogen or fluorine.

Item 5 is the compound according to any one of items 1 to 4, represented by formulae (1-2-a) to (1-2-e).

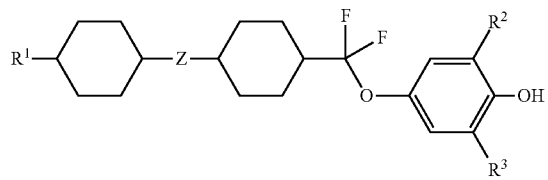
(1-2-a)

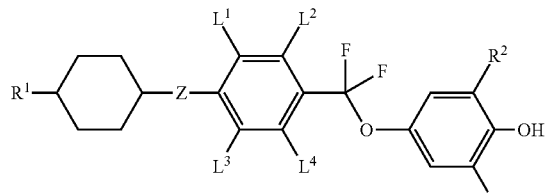
(1-2-b)

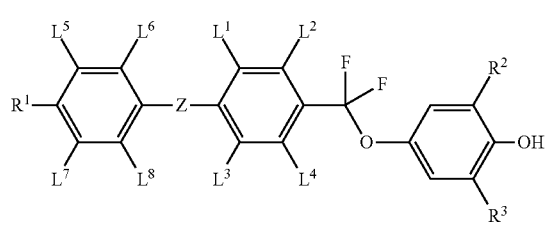
(1-2-c)

(1-2-d)

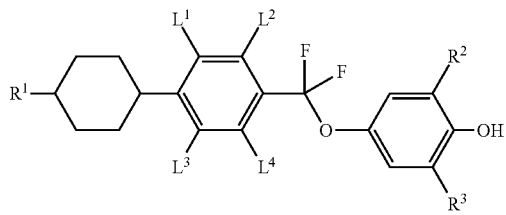

(1-2-e)

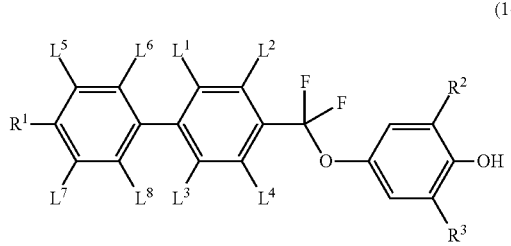

In formulae (1-2-a) to (1-2-e), $R^1$ is alkyl having 2 to 20 carbons; $R^2$ and $R^3$ are independently methyl, ethyl, isopropyl, or t-butyl; and $L^1$, $L^2$, $L^3$, $L^4$, $L^5$, $L^6$, $L^7$, and $L^8$ are independently hydrogen or fluorine.

Item 6 is the compound according to any one of items 1 to 5, wherein in formulae (1-2-a) to (1-2-e), $R^1$ is alkyl having 2 to 15 carbons; $R^2$ and $R^3$ are independently methyl or t-butyl; and $L^1$, $L^2$, $L^3$, $L^4$, $L^5$, $L^6$, $L^7$, and $L^8$ are independently hydrogen or fluorine, wherein a total amount of fluorine is an integer of 0 to 4.

(1-2-a)

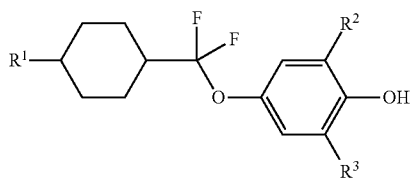

(1-2-b)

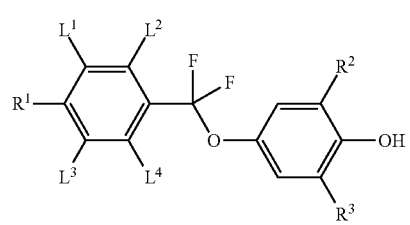

(1-2-c)

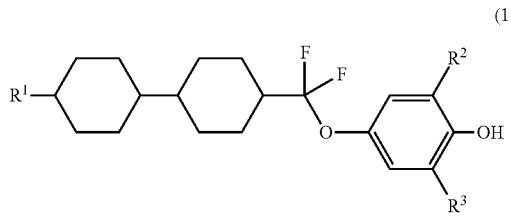

(1-2-d)

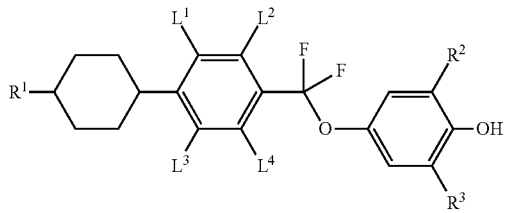

(1-2-e)

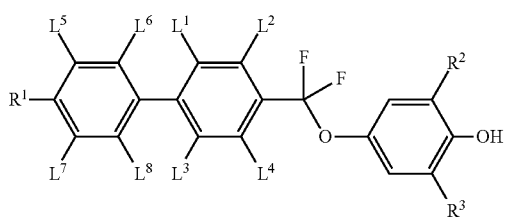

In formulae (1-2-a) to (1-2-e), $R^1$ is alkyl having 2 to 20 carbons; $R^2$ and $R^3$ are independently methyl, ethyl, isopropyl, or t-butyl; and $L^1$, $L^2$, $L^3$, $L^4$, $L^5$, $L^6$, $L^7$, and $L^8$ are independently hydrogen or fluorine.

Item 7 is the compound according to any one of items 1 to 6, represented by formulae (1-3-a) to (1-3-l).

(1-3-a)

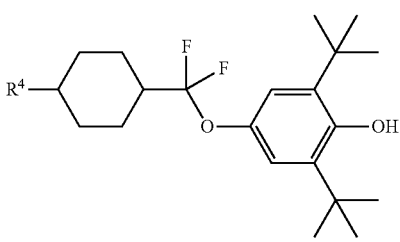

(1-3-b)

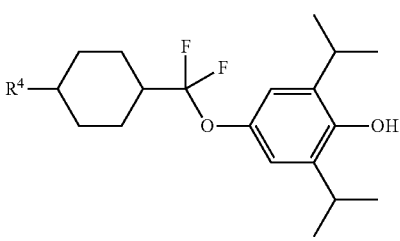

(1-3-c)

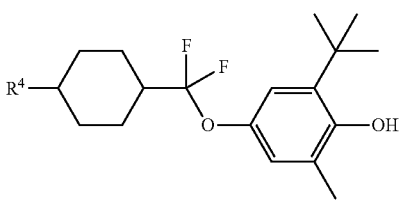

(1-3-d)

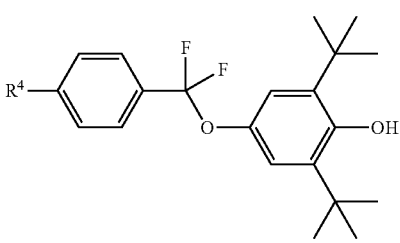

(1-3-e)
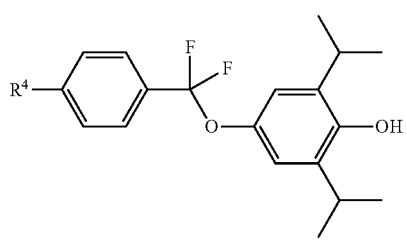

(1-3-f)
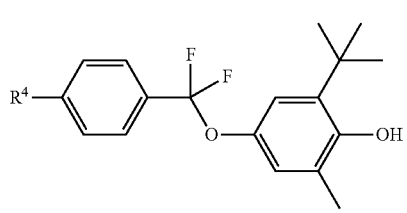

(1-3-g)
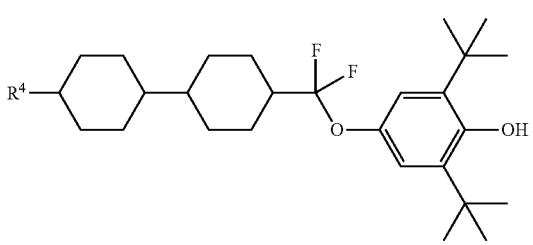

(1-3-h)
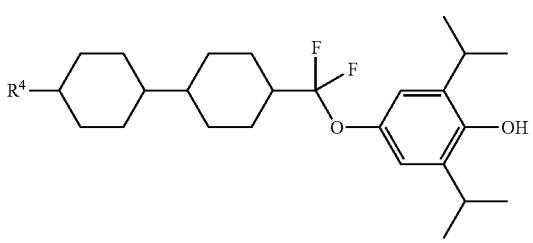

(1-3-i)
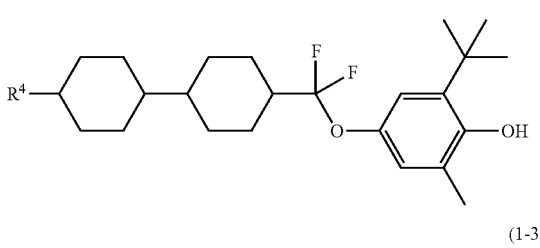

(1-3-j)
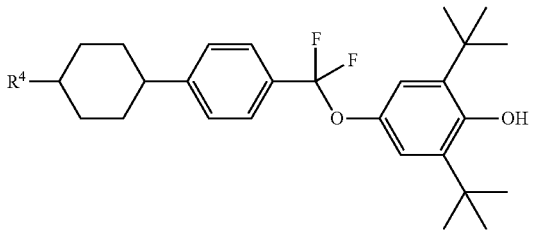

(1-3-k)
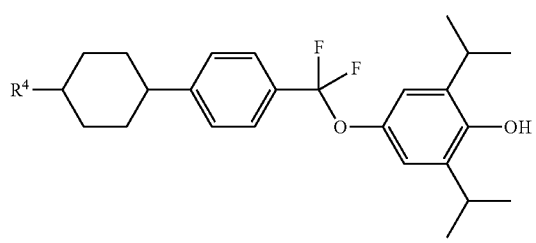

(1-3-l)
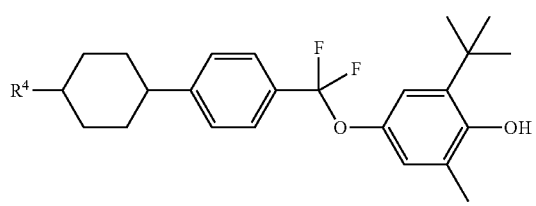

In formulae (1-3-a) to (1-3-l), $R^4$ is alkyl having 2 to 9 carbons.

Item 8 is a liquid crystal composition containing the compound according to any one of items 1 to 7.

Item 9 is the liquid crystal composition according to item 8, further containing at least one compound selected from the group consisting of compounds represented by formulae (2) to (4).

(2)
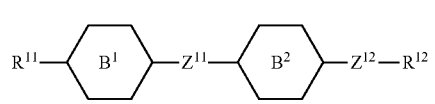

(3)
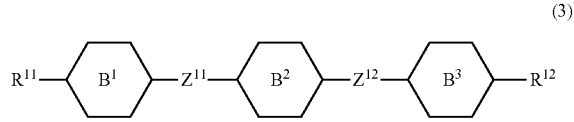

(4)
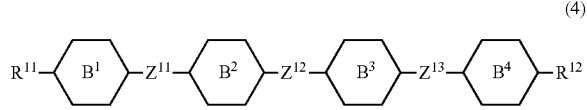

In formulae (2) to (4), $R^{11}$ and $R^{12}$ are independently alkyl having 1 to 10 carbons or alkenyl having 2 to 10 carbons, wherein at least one —CH$_2$— in the alkyl or alkenyl is optionally replaced with —O—, and at least one hydrogen in the alkyl or alkenyl is optionally replaced with fluorine;

ring $B^1$, ring $B^2$, ring $B^3$, and ring $B^4$ are independently 1,4-cyclohexylene, 1,4-phenylene, 2-fluoro-1,4-phenylene, 2,5-difluoro-1,4-phenylene, or pyrimidine-2,5-diyl; and $Z^{11}$, $Z^{12}$, and $Z^{13}$ are independently a single bond, —CH$_2$CH$_2$—, —CH=CH—, —C≡C—, or —COO—.

Item 10 is the liquid crystal composition according to item 8 or 9, further containing at least one compound selected from the group consisting of compounds represented by formulae (5) to (7).

(5)

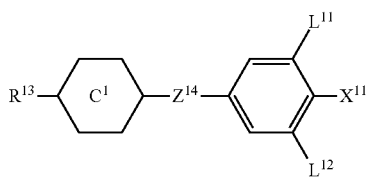

(6)

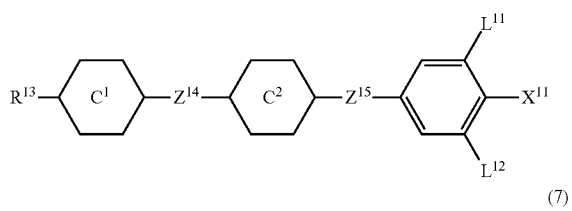

(7)

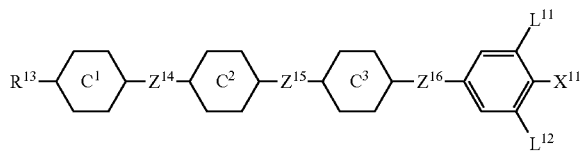

In formulae (5) to (7), $R^{13}$ is alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine;

$X^{11}$ is fluorine, chlorine, —$OCF_3$, —$OCHF_2$, —$CF_3$, —$CHF_2$, —$CH_2F$, —$OCF_2CHF_2$, or —$OCF_2CHFCF_3$;

ring $C^1$, ring $C^2$ and ring $C^3$ are independently 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl;

$Z^{14}$, $Z^{15}$, and $Z^{16}$ are independently a single bond, —$CH_2CH_2$—, —CH=CH—, —C≡C—, —COO—, —$CF_2O$—, —$OCF_2$—, —$CH_2O$—, or —$(CH_2)_4$—; and $L^{11}$ and $L^{12}$ are independently hydrogen or fluorine.

Item 11 is the liquid crystal composition according to any one of items 8 to 10, further containing at least one compound selected from the group consisting of compounds represented by formula (8).

(8)

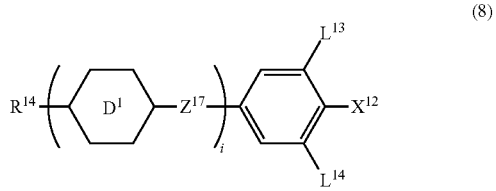

In formula (8), $R^{14}$ is alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine;

$X^{12}$ is —C≡N or —C≡C—C≡N;

ring $D^1$ is 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl;

$Z^{17}$ is a single bond, —$CH_2CH_2$—, —C≡C—, —COO—, —$CF_2O$—, —$OCF_2$—, or —$CH_2O$—;

$L^{13}$ and $L^{14}$ are independently hydrogen or fluorine; and i is 1, 2, 3, or 4.

Item 12 is the liquid crystal composition according to any one of items 8 to 11, further containing at least one compound selected from the group consisting of compounds represented by formulae (9) to (15).

(9)

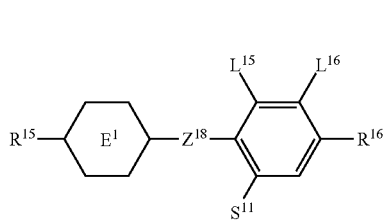

(10)

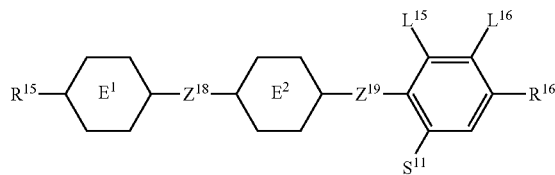

(11)

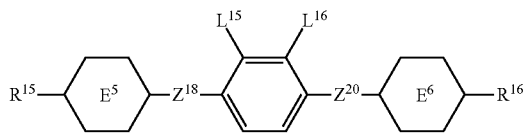

(12)

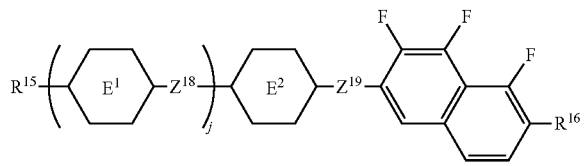

(13)

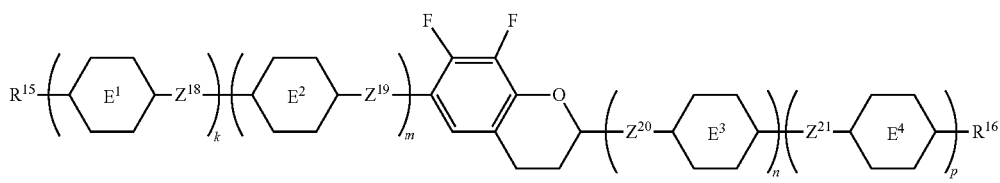

-continued

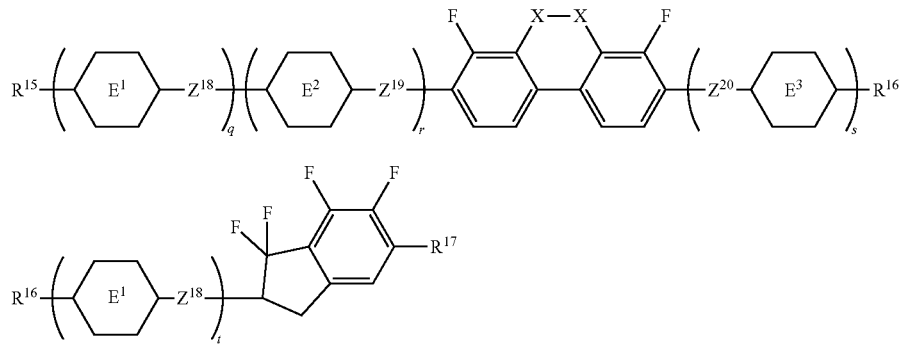

In formulae (9) to (15), $R^{15}$ and $R^{16}$ are independently alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine;

$R^{17}$ is hydrogen, fluorine, alkyl having 1 to 10 carbons, or alkenyl having 2 to 10 carbons, wherein at least one —$CH_2$— in the alkyl and alkenyl is optionally replaced with —O—, and at least one hydrogen in the alkyl and alkenyl is optionally replaced with fluorine;

ring $E^1$, ring $E^2$, ring $E^3$, and ring $E^4$ are independently 1,4-cyclohexylene, 1,4-cyclohexenylene, 1,4-phenylene in which at least one hydrogen is optionally replaced with fluorine, tetrahydropyran-2,5-diyl, or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl, or decahydronaphthalene-2,6-diyl;

$Z^{18}$, $Z^{19}$, $Z^{20}$, and $Z^{21}$ are independently a single bond, —$CH_2CH_2$—, —COO—, —$CH_2O$—, —$OCF_2$—, or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, the sum of k, m, n and p is 1 or 2, the sum of q, r and s is 0, 1, 2, or 3, and t is 1, 2, or 3.

Item 13 is a use of the compound according to any one of items 1 to 7 as an antioxidant.

Item 14 is a method for stabilizing a liquid crystal composition by adding the compound according to any one of items 1 to 7.

Item 15 is a liquid crystal display device containing the liquid crystal composition according to any one of items 8 to 12.

Item 16 is the liquid crystal display device according to item 15, wherein an operating mode of the liquid crystal display device includes a TN mode, an ECB mode, an OCB mode, a VA mode, an IPS mode, a PSA mode, an FFS mode, or an FPA mode, and a driving method for the liquid crystal display device includes an active matrix method.

Item 17 is a use of the liquid crystal composition according to any one of items 8 to 12 in a liquid crystal display device.

The invention also includes the following items: 1) the composition further containing at least one of a polymerizable compound, a polymerization initiator, a polymerization inhibitor, an optically active compound, an antioxidant, an ultraviolet absorbent, a light stabilizer, a heat stabilizer, a dye and a defoamer; 2) the composition further containing at least two of a polymerizable compound, a polymerization initiator, a polymerization inhibitor, an optically active compound, an antioxidant, an ultraviolet absorbent, a light stabilizer, a heat stabilizer, a dye and a defoamer; 3) an AM device containing the composition; 4) a device containing the composition and having a TN mode, an ECB mode, an OCB mode, a VA mode, an IPS mode, an FFS mode, a PSA mode or an FPA mode; 5) a transmissive-type device containing the composition; 6) a use of the composition as a composition having a nematic phase; and 7) a use of the composition as an optically active composition, achieved by adding an optically active compound to the composition.

Embodiments of the compound (1), synthesis of the compound (1), the liquid crystal composition and the liquid crystal display device will be described in sequence.

1. Embodiments of Compound (1)

The compound (1) of the invention is 2,6-dialkyl-4-substituted phenol having a difluoromethoxy group, and is thus useful as an antioxidant. The compound (1) has the difluoromethoxy group in the para position of the hydroxyl group. Thus, according to an electronic effect thereof, the ability of the compound (1) to capture radicals may be improved. In the compound (1), $R^2$ or $R^3$ is methyl, ethyl, isopropyl, or t-butyl. Accordingly, by selecting the groups represented by $R^2$ and $R^3$, the extent of steric hindrance of the hydroxyl group can be adjusted. When the steric hindrance is small, a reaction of supplementing radicals is sped up. When the steric hindrance is large, large stability is obtained after radicals are supplemented. Since the extent of steric hindrance of the hydroxyl group can be adjusted by a suitable combination of $R^2$ and $R^3$, an antioxidant that accords with the purpose can be obtained. By a combination of two (or three or more) compounds (1) different from each other in steric hindrance of the hydroxyl group, a synergistic effect can also be expected. The compound (1), particularly the compound in which m is 2, has a similar structure to that of a liquid crystal compound. Accordingly, when the compound (1) is added to a liquid crystal composition, good solubility is exhibited. The compound (1) has a large molecular weight and thus has low vapor pressure. Hence, when the compound (1) is added to a liquid crystal composition, the concentration will not be reduced by evaporation.

Preferred examples of the compound (1) are described. Preferred examples of a terminal group $R^1$, side chain groups $R^2$ and $R^3$, ring A, a linking group Z and a subscript m in the compound (1) are also applicable to sub-formulae of the compound (1). In the compound (1), by a suitable combination of the types of these groups, the characteristics can be arbitrarily adjusted. The compound (1) may contain an isotope such as $^2$H (deuterium) and $^{13}$C in an amount larger than the natural abundance since there is no large difference in characteristics of the compound.

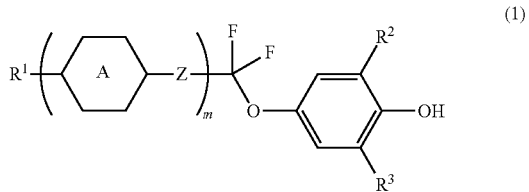

In formula (1), R$^1$ is hydrogen or alkyl having 1 to 20 carbons, wherein at least one —CH$_2$— in the alkyl is optionally replaced with —O—, —S—, —CO—, or —SiH$_2$—, and at least one —CH$_2$CH$_2$— in the alkyl is optionally replaced with —CH═CH— or —C≡C—.

R$^1$ is preferably alkyl, alkoxy, alkoxyalkyl, alkylthio, alkylthioalkyl, alkenyl, or alkynyl. R$^1$ is more preferably alkyl in which at least one —CH$_2$— is optionally replaced with —O— or —S—. R$^1$ is particularly preferably alkyl, alkoxy, or alkylthio. R$^1$ is most preferably alkyl.

In formula (1), R$^2$ and R$^3$ are independently methyl, ethyl, isopropyl, or t-butyl. R$^2$ or R$^3$ is preferably methyl, isopropyl, or t-butyl. Preferably, at least one of R$^2$ or R$^3$ is t-butyl. For R$^2$ and R$^3$, in view of steric hindrance of the hydroxyl group, a preferred combination is t-butyl and t-butyl. In view of fast reactivity of the hydroxyl group, a preferred combination is t-butyl and methyl.

In formula (1), ring A is 1,4-cyclohexylene, 1,4-cyclohexenylene, decahydronaphthalene-2,6-diyl, 1,2,3,4-tetrahydronaphthalene-2,6-diyl, 1,4-phenylene, or naphthalene-2,6-diyl, wherein at least one —CH$_2$— in these groups is optionally replaced with —O—, —S—, —CO—, or —SiH$_2$—, at least one —CH$_2$CH$_2$— in these groups is optionally replaced with —CH═CH— or —CH═N—, and at least one hydrogen in these divalent groups is optionally replaced with fluorine, chlorine, —C≡N, —CF$_3$, —CHF$_2$, —CH$_2$F, —OCF$_3$, —OCHF$_2$, or —OCH$_2$F. In formula (1), when m=2, two rings A may be the same or different.

Ring A is preferably 1,4-cyclohexylene, 1,4-cyclohexenylene, tetrahydropyran-2,5-diyl, 1,4-phenylene, or 1,4-phenylene in which at least one hydrogen is replaced with fluorine or chlorine. Ring A is more preferably 1,4-cyclohexylene, tetrahydropyran-2,5-diyl, 1,4-phenylene, 2-fluoro-1,4-phenylene, 2-chloro-1,4-phenylene, 2,3-difluoro-1,4-phenylene, 2,5-difluoro-1,4-phenylene, or 2,6-difluoro-1,4-phenylene. Ring A is particularly preferably 1,4-cyclohexylene, 1,4-phenylene, or 2-fluoro-1,4-phenylene.

In formula (1), Z is a single bond or alkylene having 1 to 6 carbons, wherein at least one —CH$_2$— in the alkylene is optionally replaced with —O—, —S—, —CO—, or —SiH$_2$—, one or two —CH$_2$CH$_2$— in the alkylene are optionally replaced with —CH═CH— or and at least one hydrogen in these divalent groups is optionally replaced with fluorine or chlorine. In formula (1), when m=2, two Z's may be the same or different.

Z is preferably a single bond, —CH$_2$CH$_2$—, —CH═CH—, —C≡C—, —COO—, —OCO—, —CH$_2$O—, —OCH$_2$—, —CF═CF—, —CF$_2$CF$_2$—, —CH$_2$CF$_2$—, —CH$_2$CHF—, —CH$_2$S—, or —SCH$_2$—. Z is more preferably a single bond, —CH$_2$CH$_2$—, —CH═CH—, —C≡C—, —COO—, —OCO—, —CH$_2$O—, or —OCH$_2$—. Z is particularly preferably a single bond or —CH$_2$CH$_2$—. Z is most preferably a single bond.

In formula (1), m is 0, 1, or 2. M is preferably 0 in view of easy synthesis. In this case, R$^1$ is preferably long-chain in view of high solubility. M is preferably 1 or 2. M is more preferably 1 in view of high solubility, and is more preferably 2 in view of low vapor pressure. M is particularly preferably 2. When R$^1$ is long-chain, m is particularly preferably 1.

With reference to the above preferred examples, by suitably selecting a combination of the terminal group R$^1$, the side chain groups R$^2$ and R$^3$, ring A, the linking group Z and the subscript m, the compound (1) having intended characteristics can be obtained. Examples of the compound (1) include the compound described in item 4. More specific examples of the compound (1) include the compound described in item 5. Even more specific examples of the compound (1) include the compound described in item 7.

2. Synthesis of Compound (1)

A synthesis method of the compound (1) of the invention is described. The compound (1) can be synthesized by a suitable combination of methods in organic synthetic chemistry. The methods for introducing target terminal groups, rings or linking groups into starting materials are described in books such as Houben-Weyl, Methoden der Organische Chemie (Georg-Thieme Verlag, Stuttgart), Organic Syntheses (John Wiley & Sons, Inc.), Organic Reactions (John Wiley & Sons, Inc.), Comprehensive Organic Synthesis (Pergamon Press), and New Experimental Chemistry Course (Shin Jikken Kagaku Koza, in Japanese) (Maruzen Co., Ltd.), etc.

2-1. Synthesis Route (A)

In the following compound (5), the ring adjacent to the difluoromethoxy group is 1,4-cyclohexylene. Such a compound can be synthesized following a synthesis route (A) as follows.

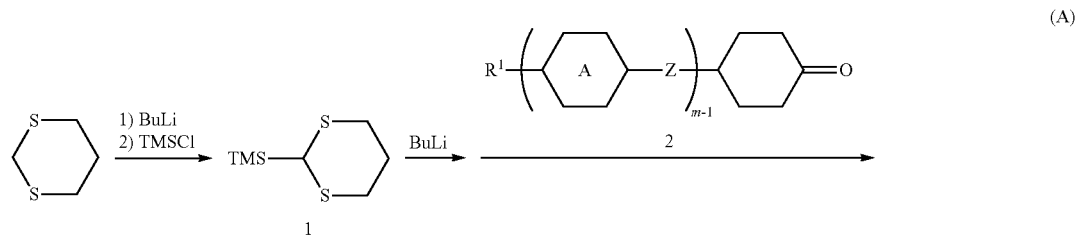

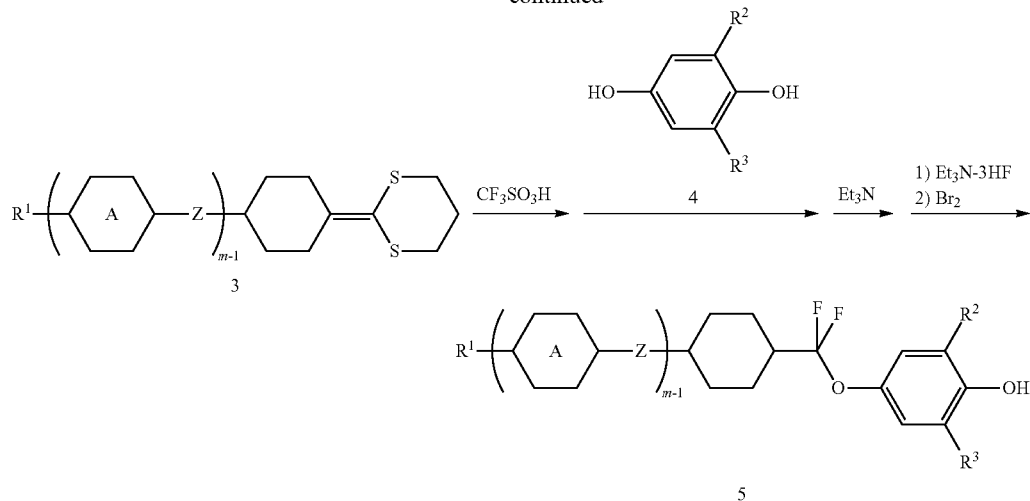

2-2. Synthesis Route (B)

In the following compound (4), the ring adjacent to the difluoromethoxy group is 1,4-phenylene. Such a compound can be synthesized following a synthesis route (B) as follows.

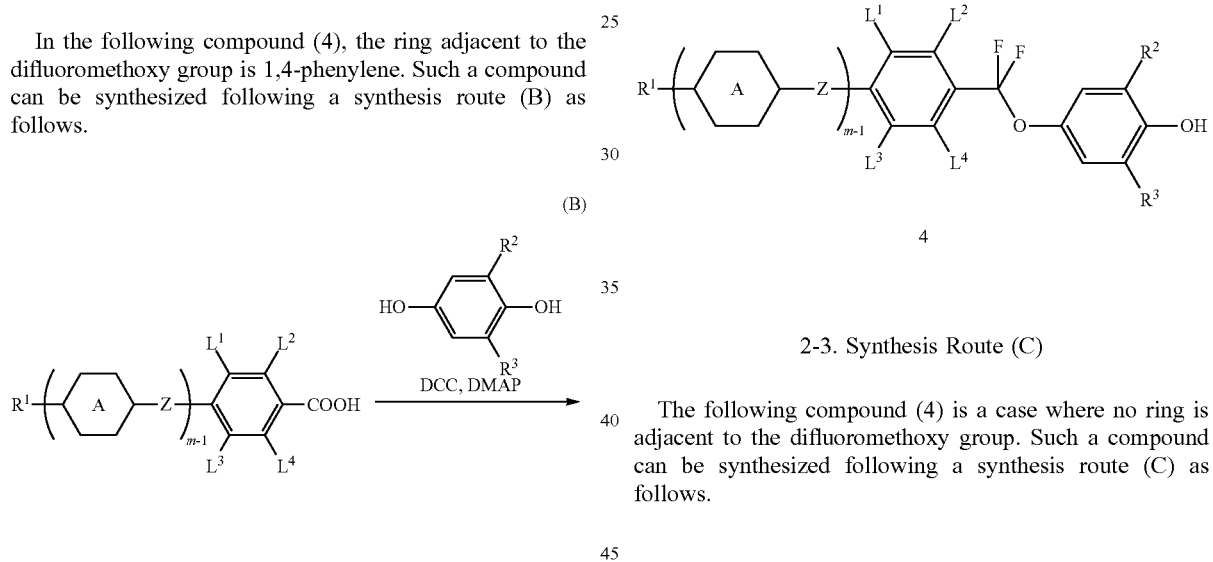

2-3. Synthesis Route (C)

The following compound (4) is a case where no ring is adjacent to the difluoromethoxy group. Such a compound can be synthesized following a synthesis route (C) as follows.

-continued

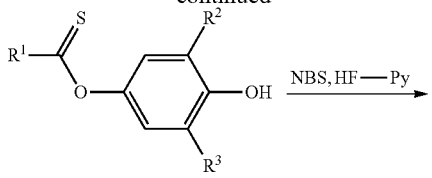

3

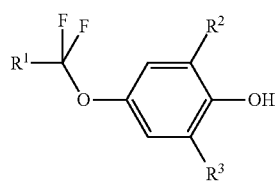

4

3. Liquid Crystal Composition

The liquid crystal composition of the invention contains the compound (1) as a component A. The compound (1) is suitable for preventing the liquid crystal composition from being decomposed by light or heat. Preferably, this composition contains the compound (1) as the component A, and further contains a liquid crystal compound selected from components B, C, D and E shown below. The component B includes compounds (2) to (4). The component C includes compounds (5) to (7). The component D includes a compound (8). The component E includes compounds (9) to (15). This composition may contain other liquid crystal compounds different from the compounds (2) to (15). In preparing this composition, it is preferred to select the components B, C, D and E by taking positive or negative dielectric anisotropy and the magnitude of dielectric anisotropy, etc. into consideration. The composition in which the components are suitably selected has high maximum temperature, low minimum temperature, small viscosity, suitable (large or small) optical anisotropy, large positive or negative dielectric anisotropy and a suitable (large or small) elastic constant.

A preferred ratio of the compound (1) based on the weight of the liquid crystal composition is about 0.001 wt % or more in order to maintain high stability to ultraviolet light, and is about 5 wt % or less in order to enable the compound (1) to dissolve in the liquid crystal composition. The ratio is more preferably about 0.005 to 2 wt %, particularly preferably about 0.01 to 1 wt %, and most preferably about 0.01 to 0.5 wt %.

The component B is a compound in which two terminal groups are alkyl or the like. Preferred examples of the component B include compounds (2-1) to (2-11), compounds (3-1) to (3-19) and compounds (4-1) to (4-7). In the compounds as the component B, $R^{11}$ and $R^{12}$ are independently alkyl having 1 to 10 carbons or alkenyl having 2 to 10 carbons, wherein at least one —$CH_2$— in the alkyl or alkenyl is optionally replaced with —O—, and at least one hydrogen in the alkyl or alkenyl is optionally replaced with fluorine.

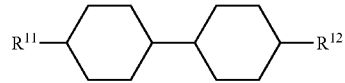

(2-1)

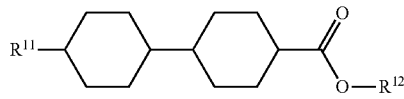

(2-2)

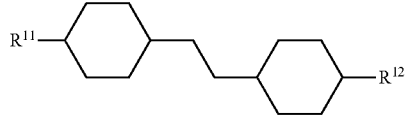

(2-3)

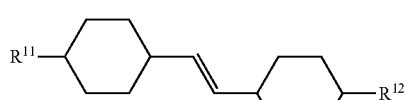

(2-4)

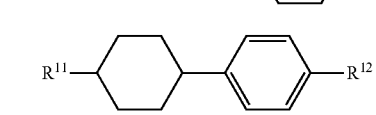

(2-5)

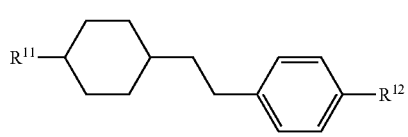

(2-6)

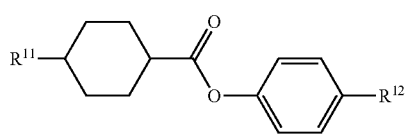

(2-7)

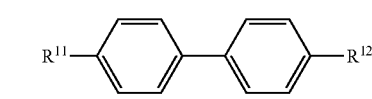

(2-8)

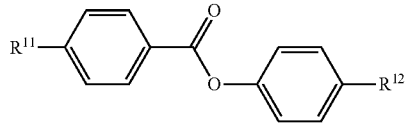

(2-9)

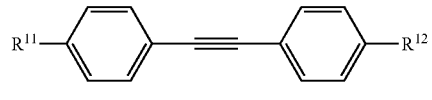

(2-10)

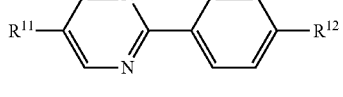

(2-11)

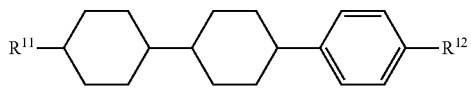

(3-1)

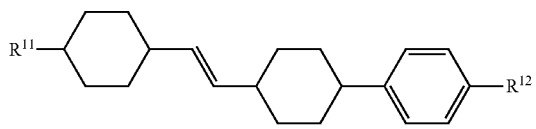

(3-2)

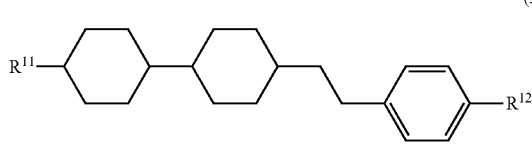

(3-3)

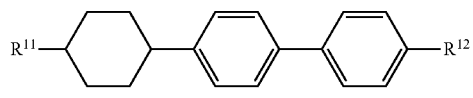 (3-4)
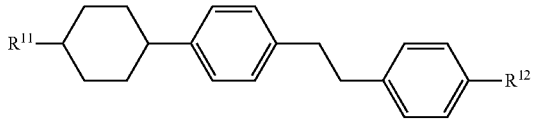 (3-5)
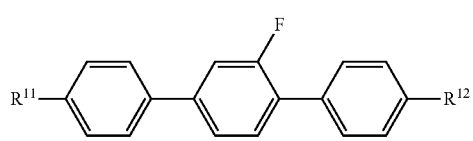 (3-6)
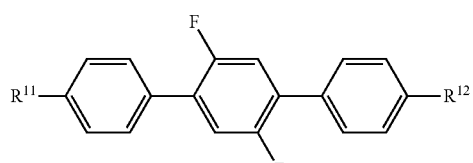 (3-7)
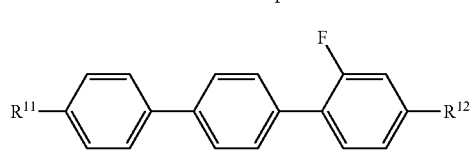 (3-8)
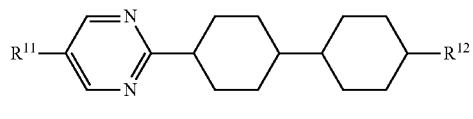 (3-9)
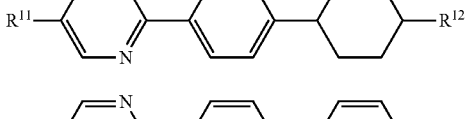 (3-10)
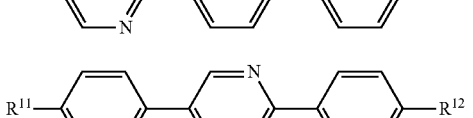 (3-11)
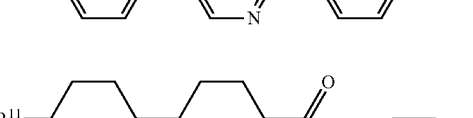 (3-12)
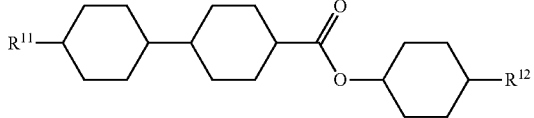 (3-13)
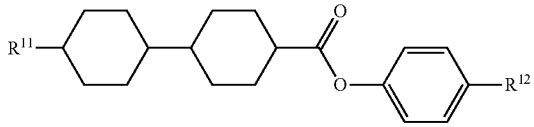 (3-14)
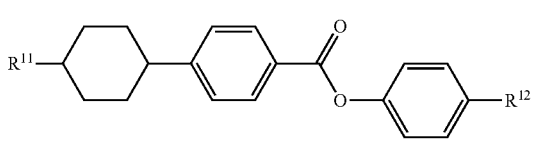 (3-15)
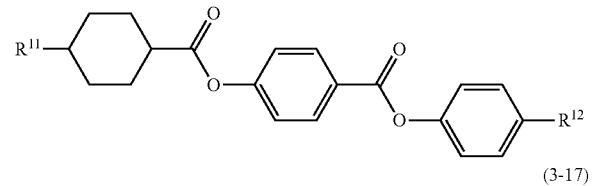 (3-16)
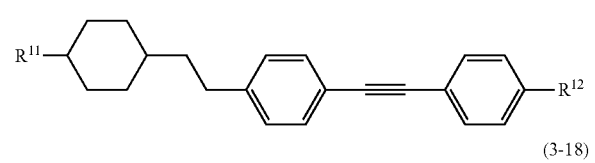 (3-17)
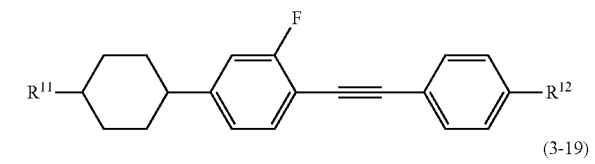 (3-18)
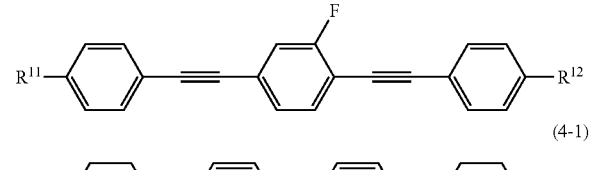 (3-19)
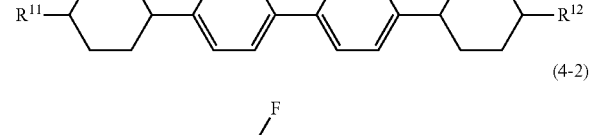 (4-1)
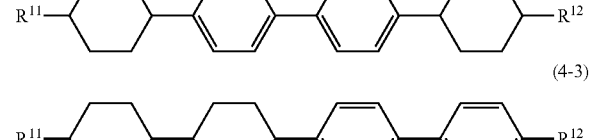 (4-2)
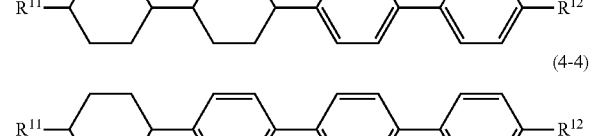 (4-3)
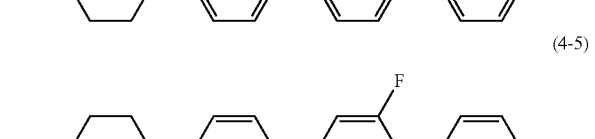 (4-4)
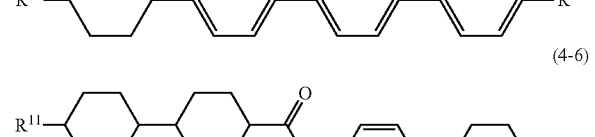 (4-5)
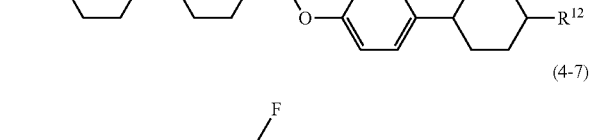 (4-6)
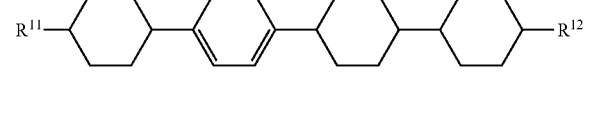 (4-7)

The component B has a small absolute value of dielectric anisotropy, and is thus nearly neutral. The compound (2) mainly has an effect of reducing viscosity or adjusting optical anisotropy. The compounds (3) and (4) have an effect of broadening the temperature range of a nematic phase by increasing the maximum temperature, or of adjusting optical anisotropy.

As the content of the component B is increased, the dielectric anisotropy of the composition is reduced and the viscosity is reduced. Therefore, the content is preferably as high as possible as long as a required value of threshold voltage of the device is satisfied. In preparing the composition for use in modes such as IPS and VA, etc., the content of the component B is preferably 30 wt % or more, more preferably 40 wt % or more, based on the weight of the liquid crystal composition.

The component C is a compound having halogen or a fluorine-containing group in the right terminal. Preferred examples of the component C include compounds (5-1) to (5-16), compounds (6-1) to (6-113) and compounds (7-1) to (7-57). In the compounds as the component C, $R^{13}$ is alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine; $X^{11}$ is fluorine, chlorine, —$OCF_3$, —$OCHF_2$, —$CF_3$, —$CHF_2$, —$CH_2F$, —$OCF_2CHF_2$, or —$OCF_2CHFCF_3$.

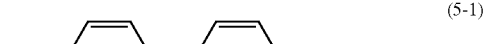
(5-1)

(5-2)

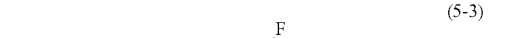
(5-3)

(5-4)

(5-5)

(5-6)

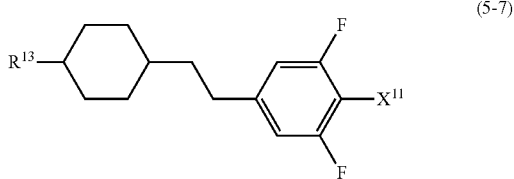
(5-7)

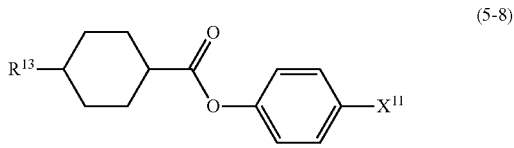
(5-8)

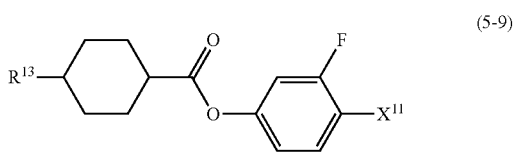
(5-9)

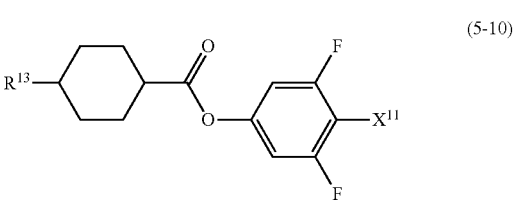
(5-10)

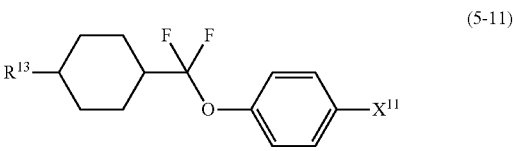
(5-11)

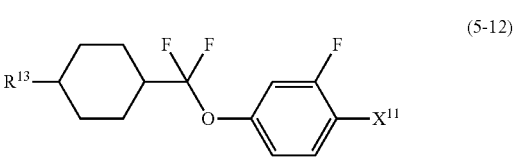
(5-12)

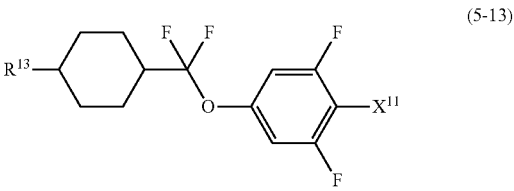
(5-13)

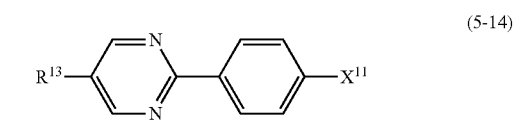
(5-14)

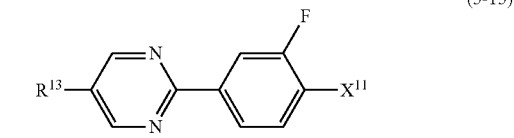
(5-15)

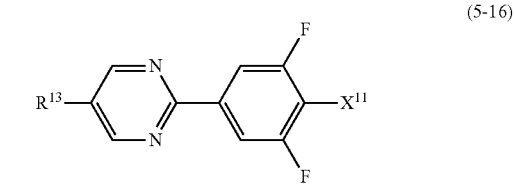
(5-16)

(6-1) 
(6-2) 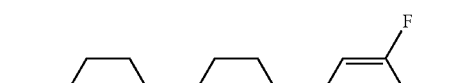
(6-3) 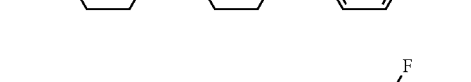
(6-4) 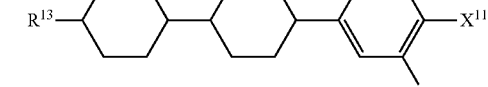
(6-5) 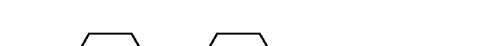
(6-6) 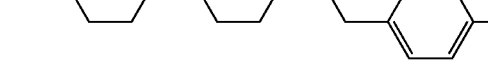
(6-7) 
(6-8) 
(6-9) 
(6-10) 
(6-11) 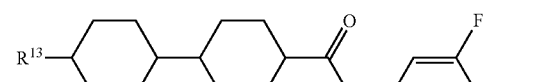
(6-12) 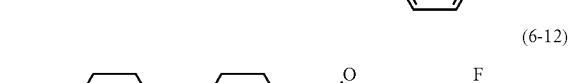
(6-13) 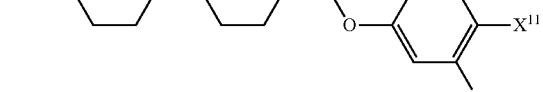
(6-14) 
(6-15) 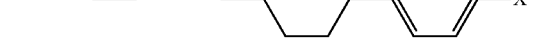
(6-16) 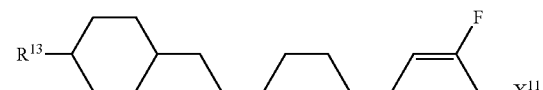
(6-17) 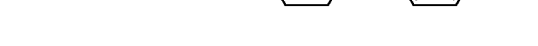
(6-18) 
(6-19) 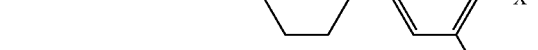

-continued
(6-20)
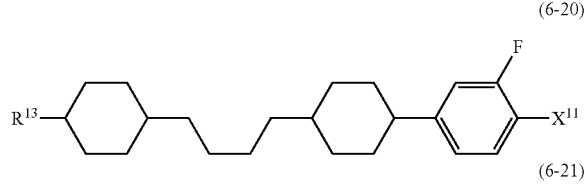
(6-21)
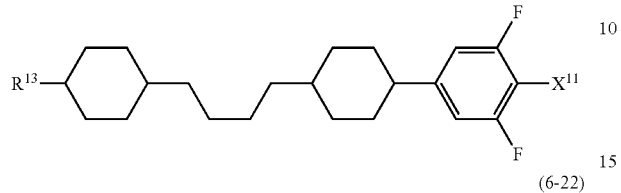
(6-22)
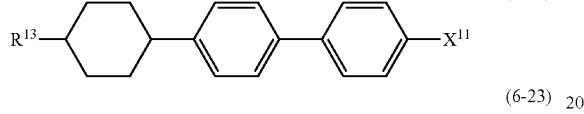
(6-23)
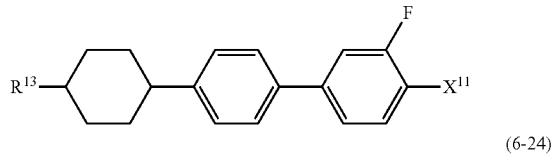
(6-24)
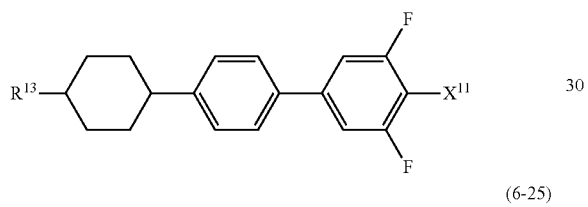
(6-25)
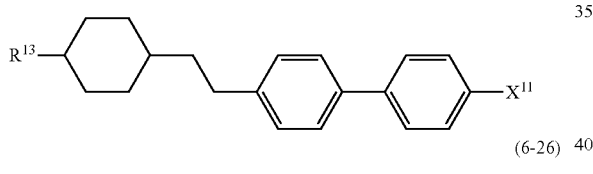
(6-26)
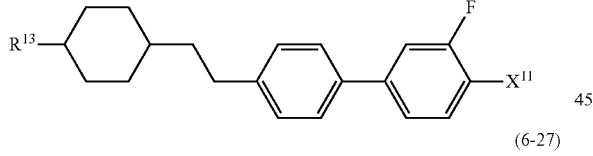
(6-27)
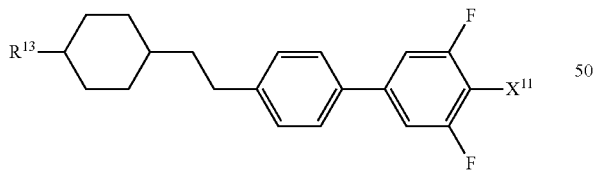
(6-28)
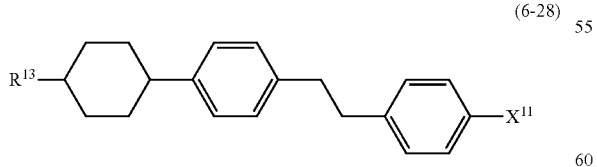
(6-29)
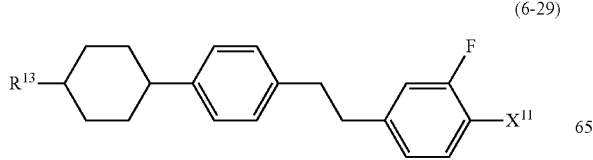
-continued
(6-30)
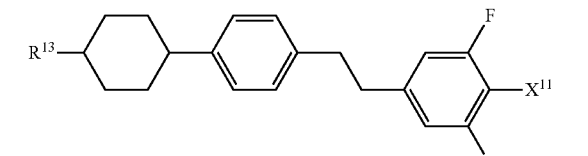
(6-31)
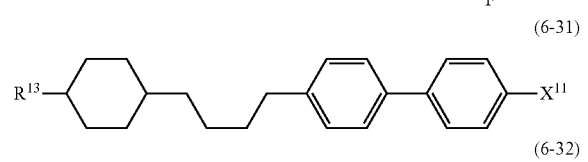
(6-32)
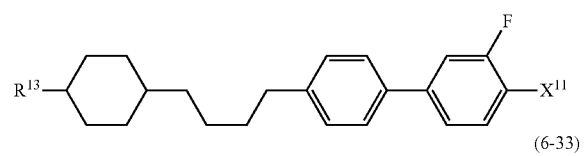
(6-33)
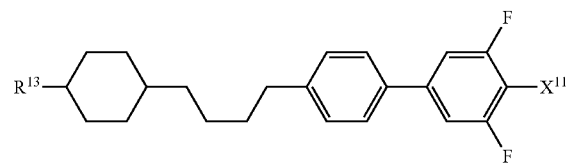
(6-34)
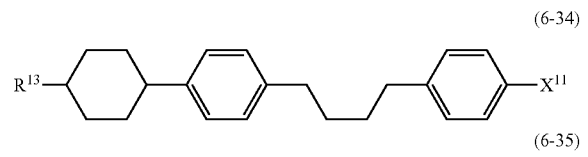
(6-35)
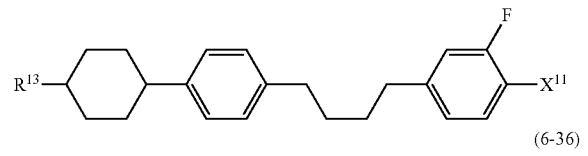
(6-36)
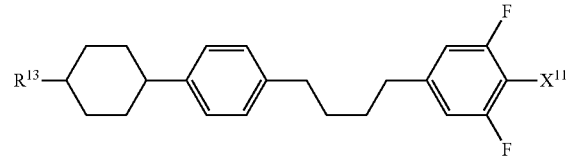
(6-37)
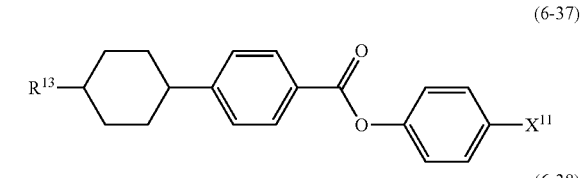
(6-38)
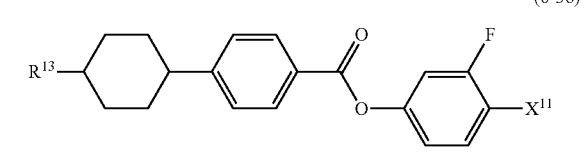
(6-39)
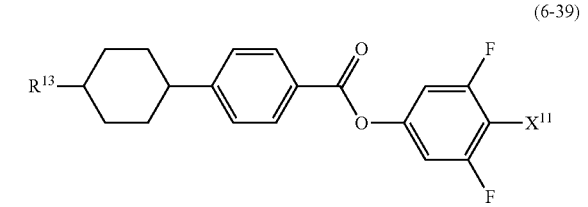

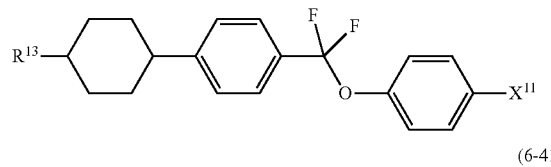 (6-40)
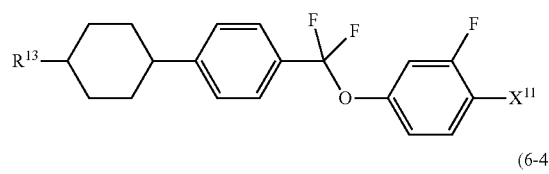 (6-41)
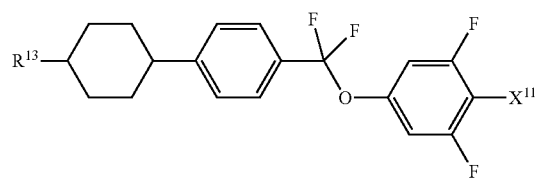 (6-42)
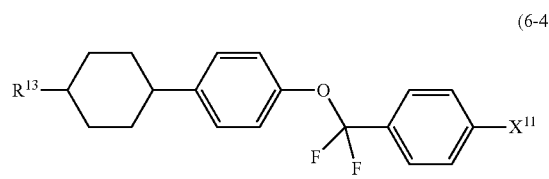 (6-43)
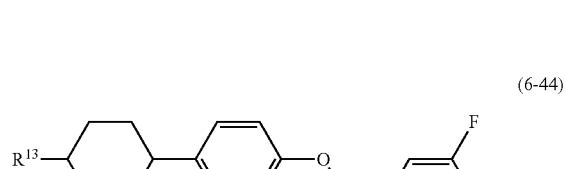 (6-44)
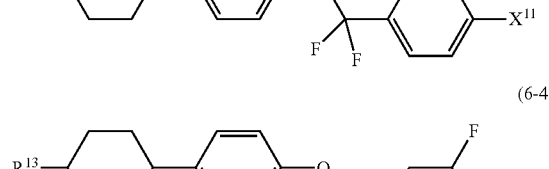 (6-45)
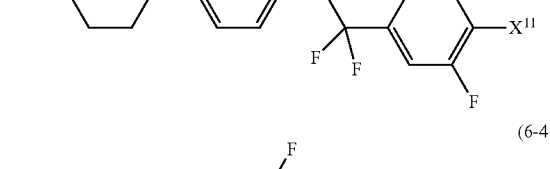 (6-46)
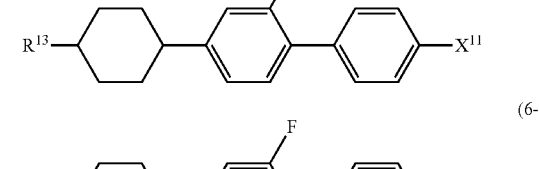 (6-47)
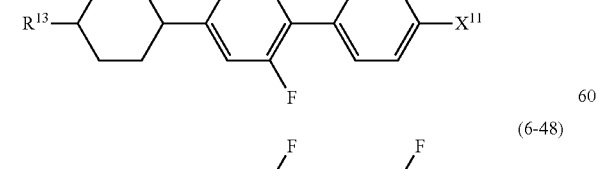 (6-48)
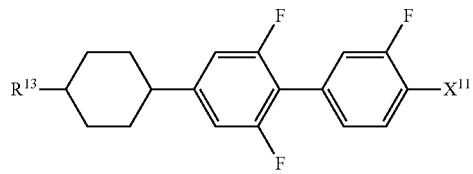 (6-49)
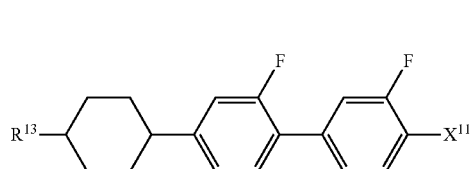 (6-50)
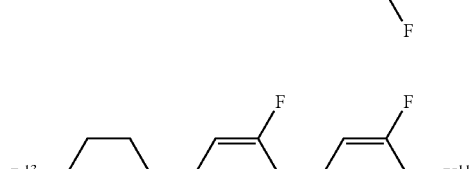 (6-51)
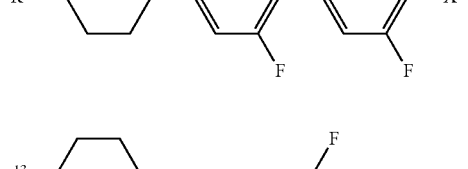 (6-52)
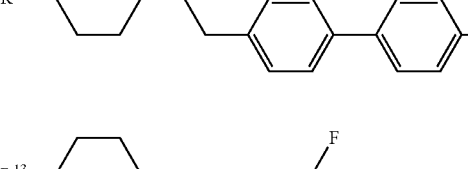 (6-53)
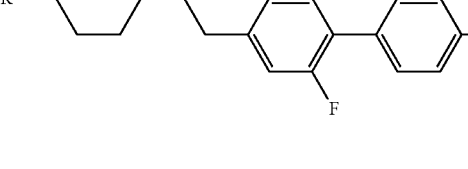 (6-54)
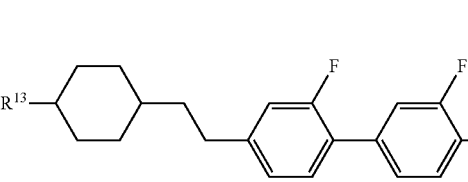 (6-55)
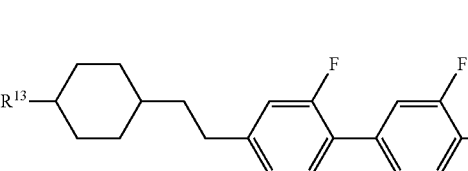 (6-56)

(6-57) 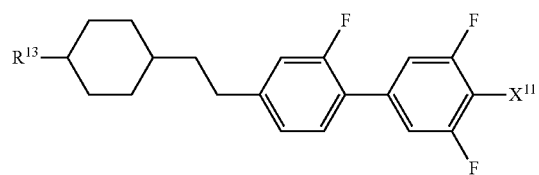
(6-58) 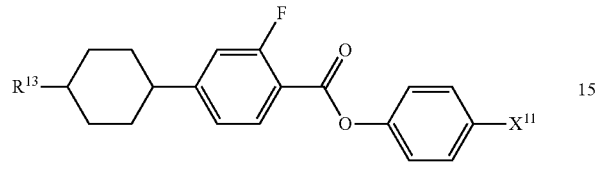
(6-59) 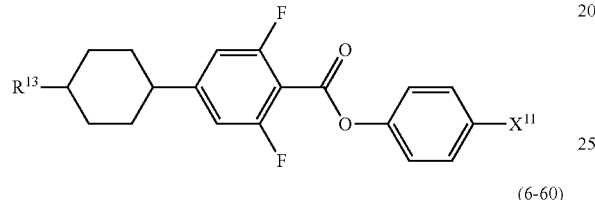
(6-60) 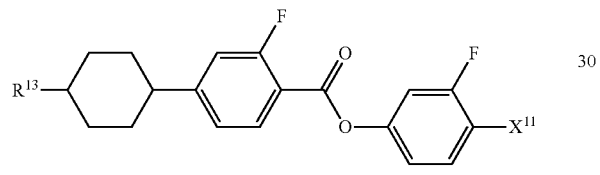
(6-61) 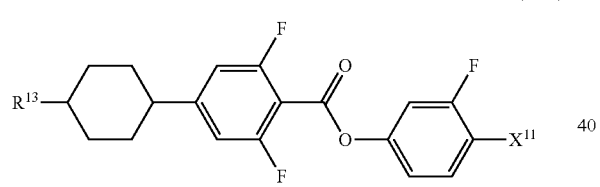
(6-62) 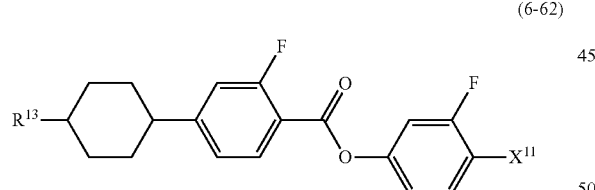
(6-63) 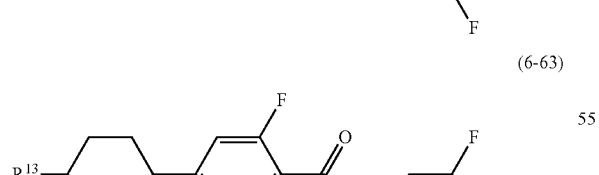
(6-64) 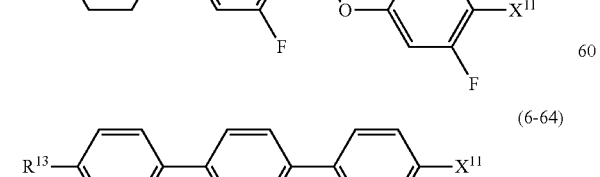
(6-65) 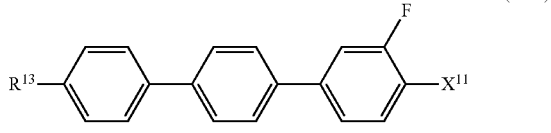
(6-66) 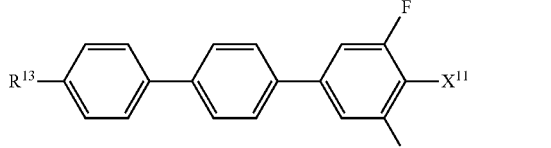
(6-67) 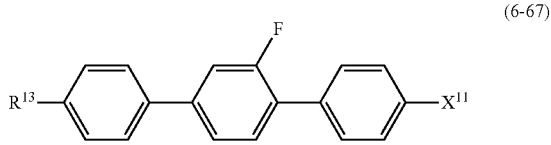
(6-68) 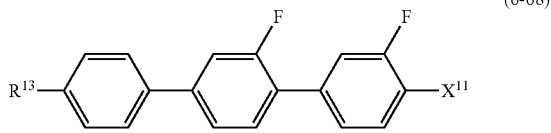
(6-69) 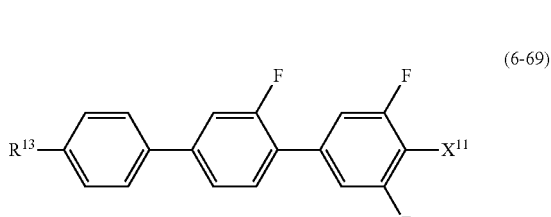
(6-70) 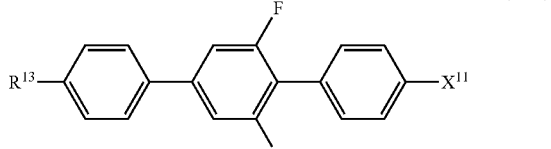
(6-71) 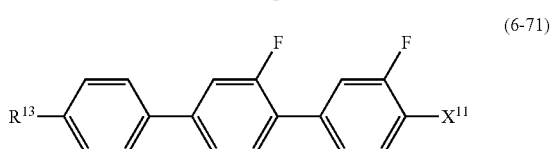
(6-72) 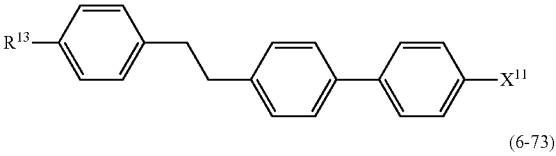
(6-73) 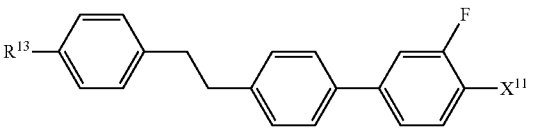

(6-74)
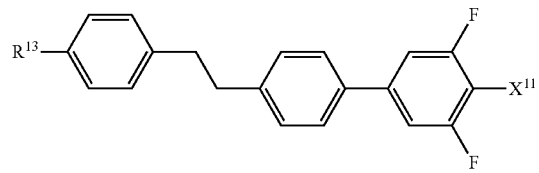
(6-75)
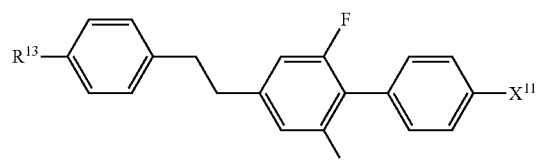
(6-76)
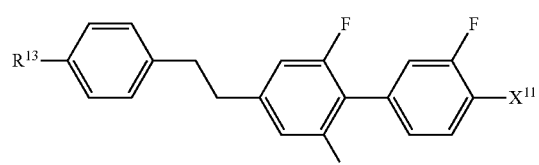
(6-77)
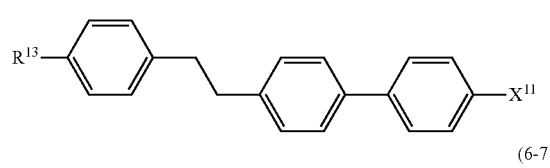
(6-78)
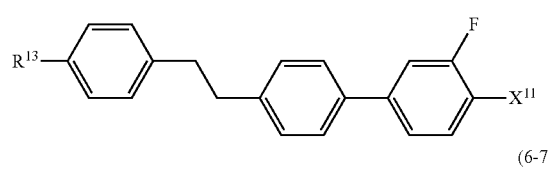
(6-79)
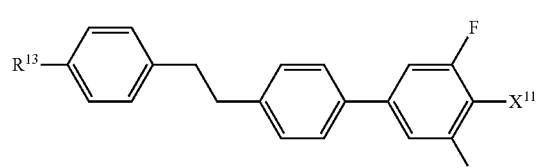
(6-80)
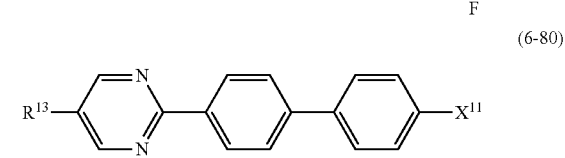
(6-81)
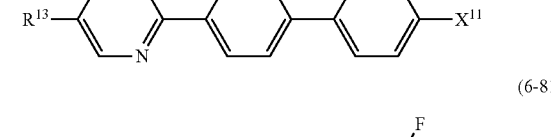
(6-82)
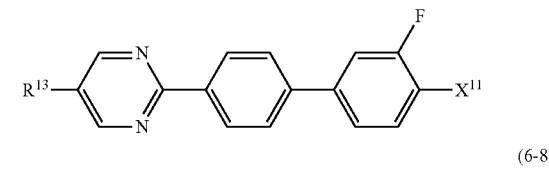
(6-83)
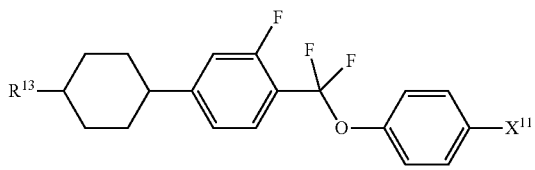
(6-84)
(6-85)
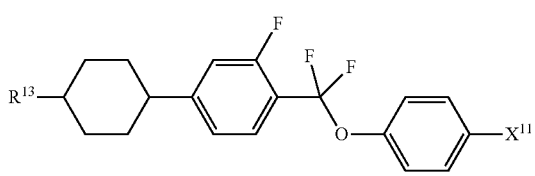
(6-86)
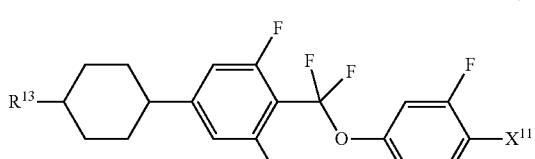
(6-87)
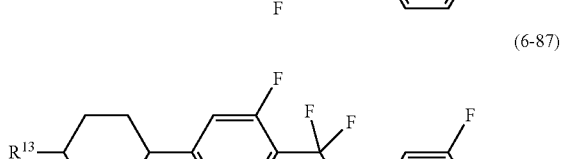
(6-88)
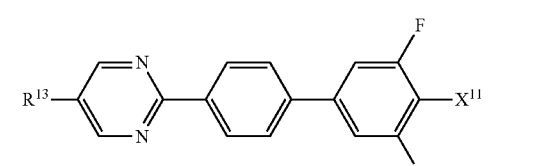
(6-89)
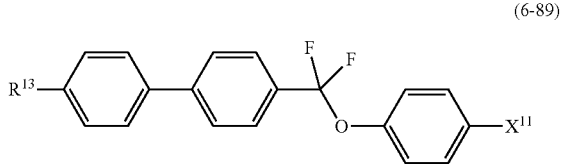
(6-90)
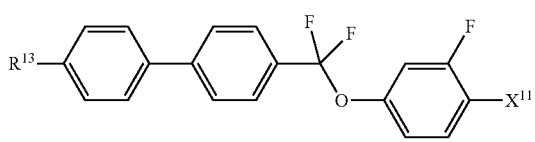

(6-91) 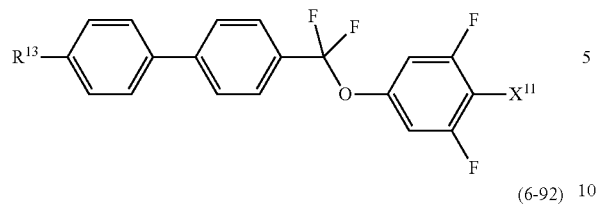
(6-92) 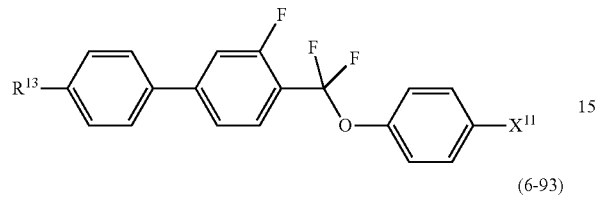
(6-93) 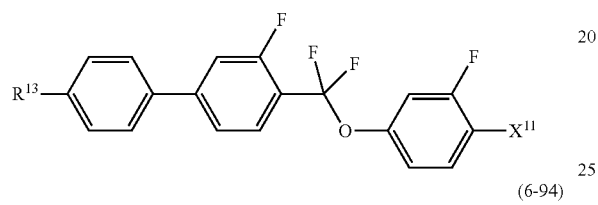
(6-94) 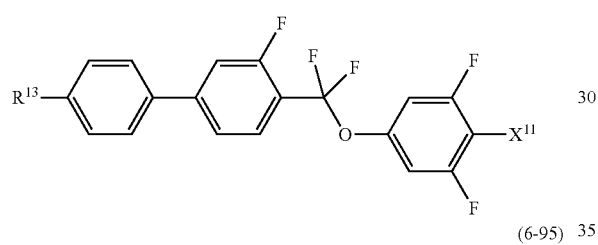
(6-95) 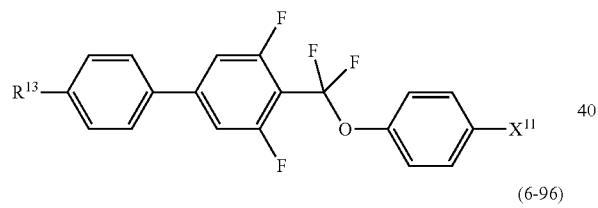
(6-96) 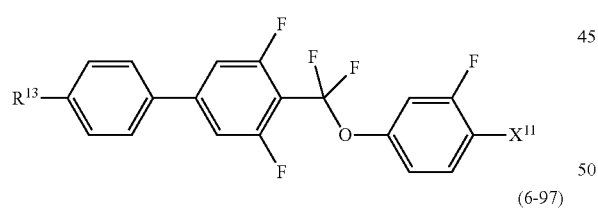
(6-97) 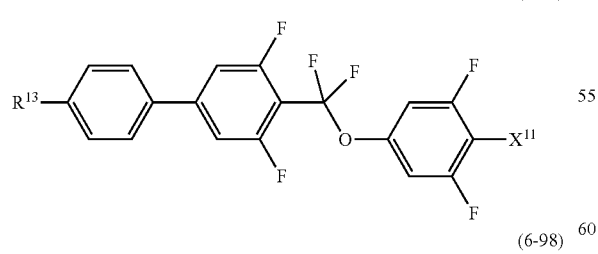
(6-98) 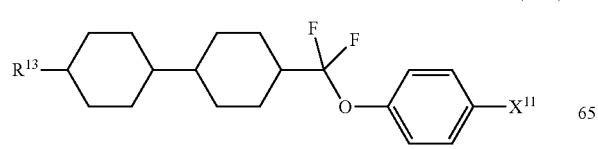
(6-99) 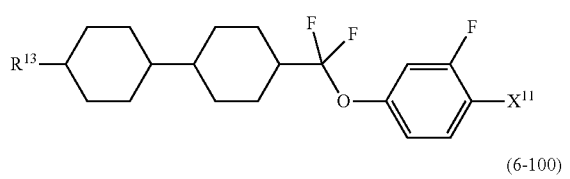
(6-100) 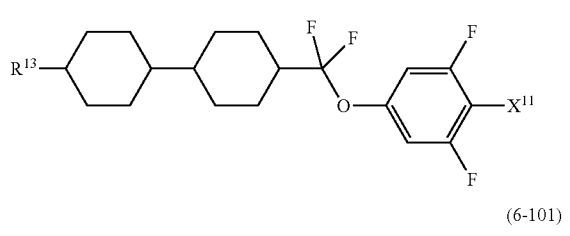
(6-101) 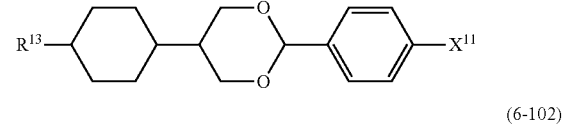
(6-102) 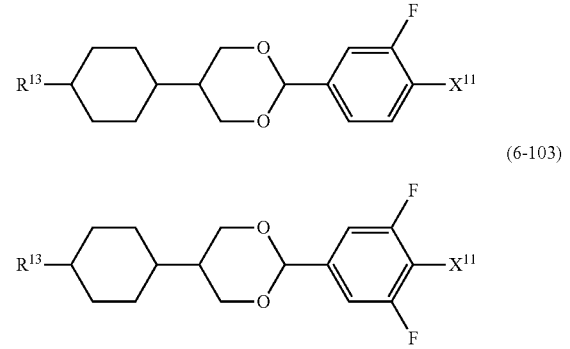
(6-103) 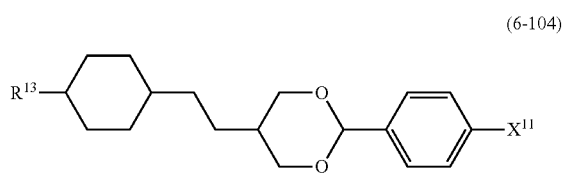
(6-104) 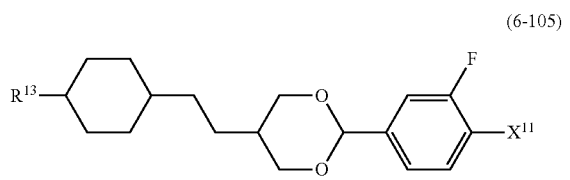
(6-105) 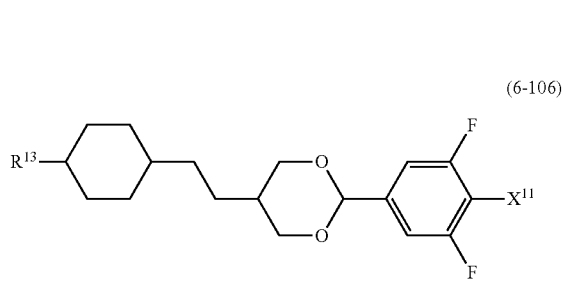
(6-106) 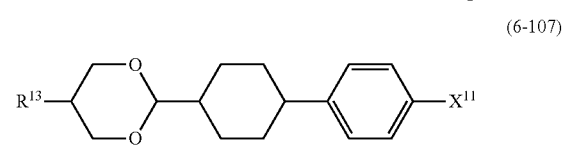
(6-107)

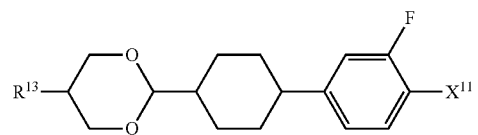
(6-108)
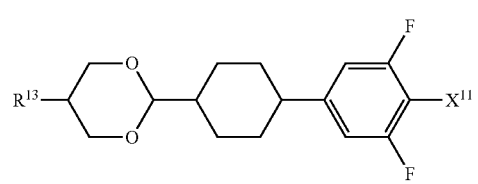
(6-109)
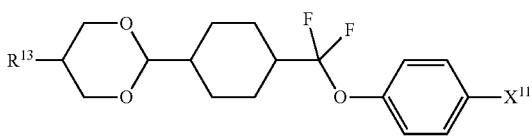
(6-110)
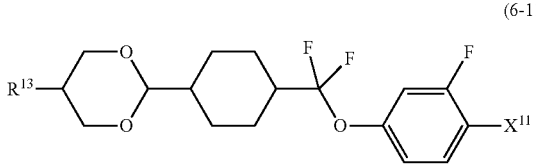
(6-111)
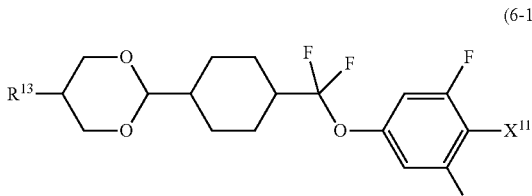
(6-112)
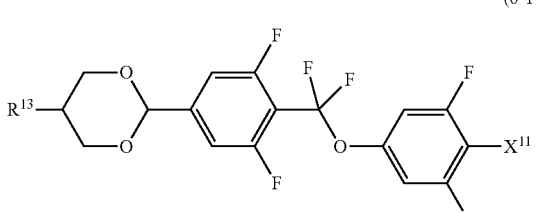
(6-113)
(7-1)
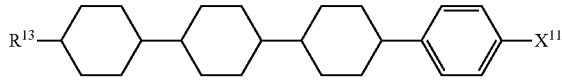
(7-2)
(7-3)
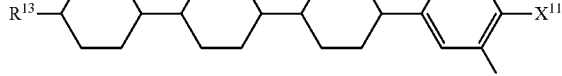
(7-4)
(7-5)
(7-6)
(7-7)
(7-8)
(7-9)
(7-10)
(7-11)
(7-12)

(7-32) 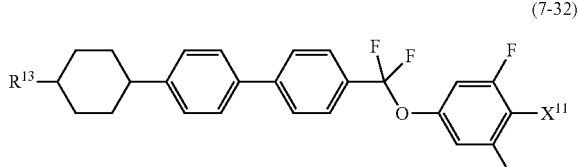
(7-33) 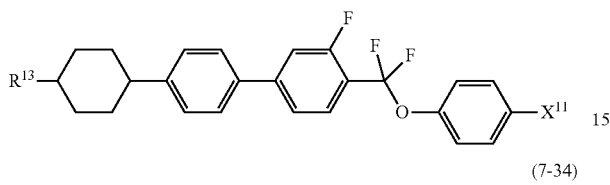
(7-34) 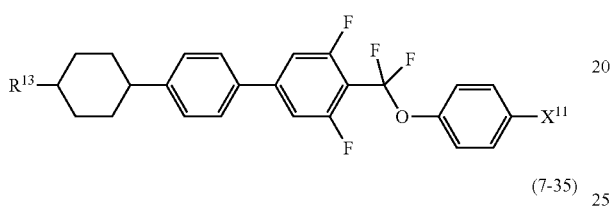
(7-35) 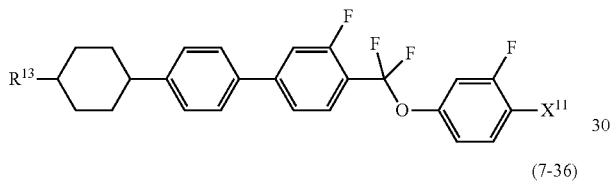
(7-36) 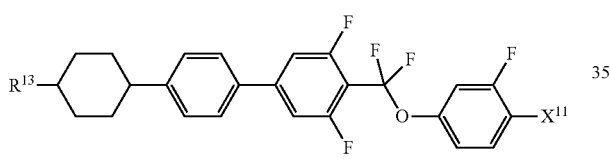
(7-37) 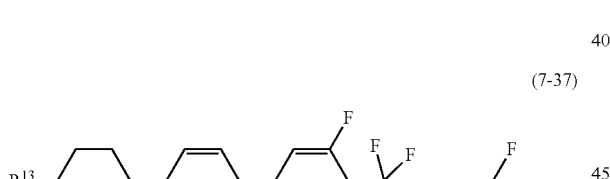
(7-38) 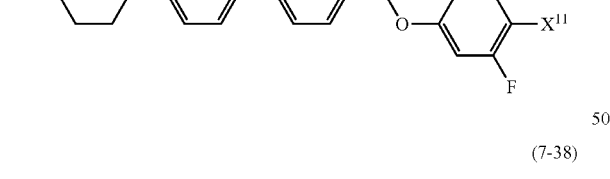
(7-39) 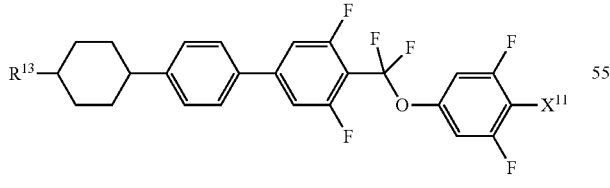
(7-40) 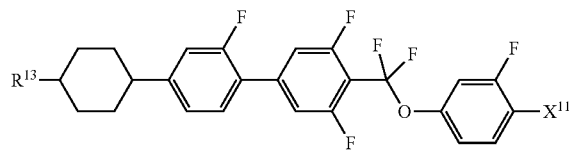
(7-41) 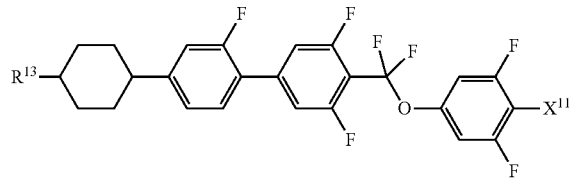
(7-42) 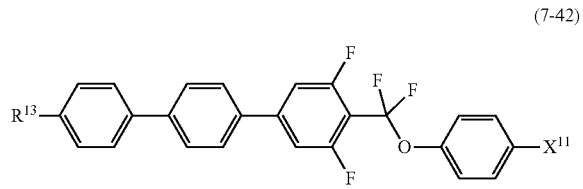
(7-43) 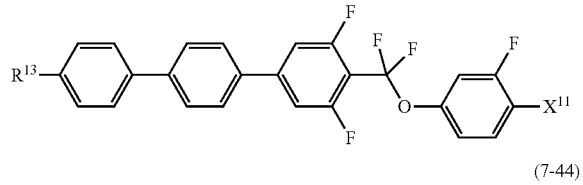
(7-44) 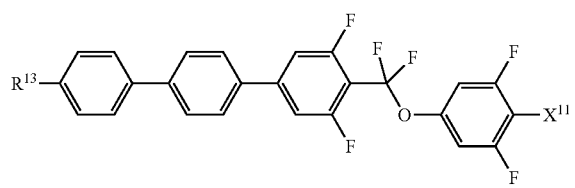
(7-45) 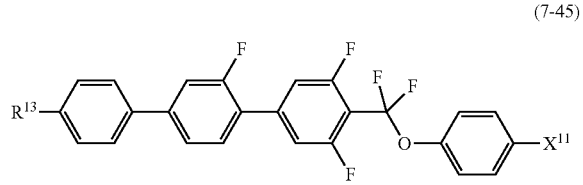
(7-46) 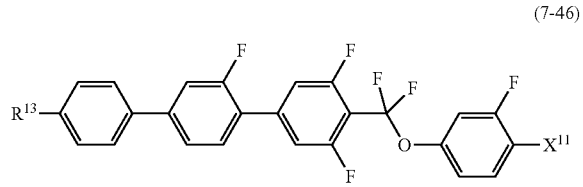
(7-47) 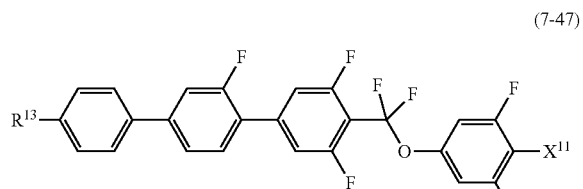

(7-48)
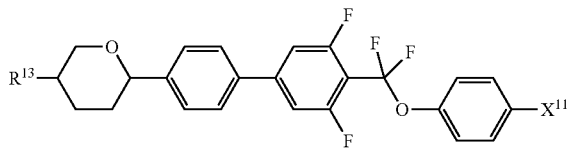

(7-49)
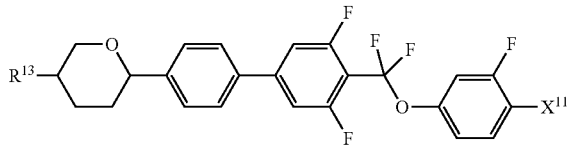

(7-50)
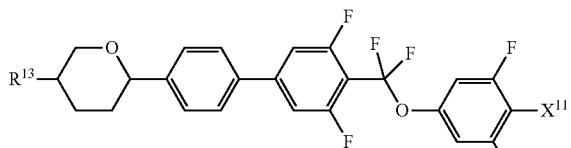

(7-51)
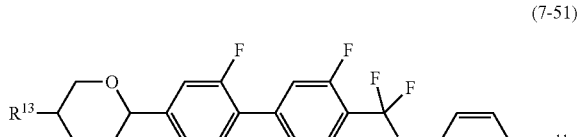

(7-52)
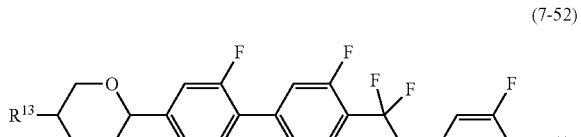

(7-53)

(7-54)
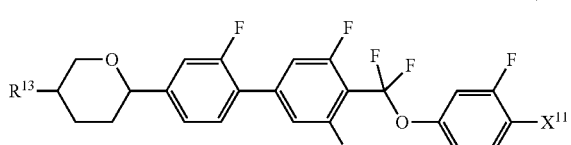

(7-55)
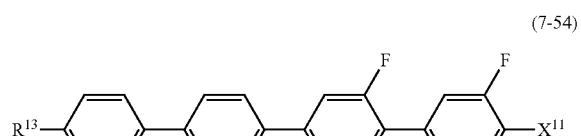

(7-56)
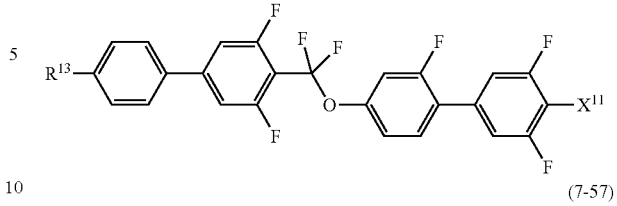

(7-57)
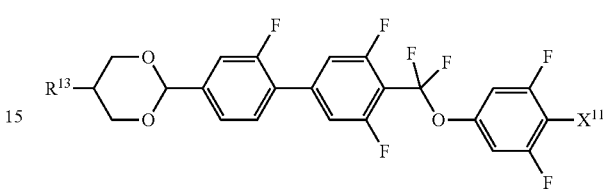

The component C has positive dielectric anisotropy and very excellent stability to heat and light, etc., and can thus be used for preparing the composition for use in modes such as IPS, FFS, and OCB, etc. The content of the component C is suitably 1 to 99 wt %, preferably 10 to 97 wt %, and more preferably 40 to 95 wt %, based on the weight of the liquid crystal composition. When the component C is added to a composition having negative dielectric anisotropy, the content of the component C is preferably 30 wt % or less based on the weight of the liquid crystal composition. By addition of the component C, the elastic constant of the composition can be adjusted, and a voltage-transmittance curve of the device can be adjusted.

The component D is the compound (8) in which the right terminal group is —C≡N or —C≡C—C≡N. Preferred examples of the component D include compounds (8-1) to (8-64). In the compounds as the component D, $R^{14}$ is alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine; and $X^{12}$ is —C≡N or —C≡C—C≡N.

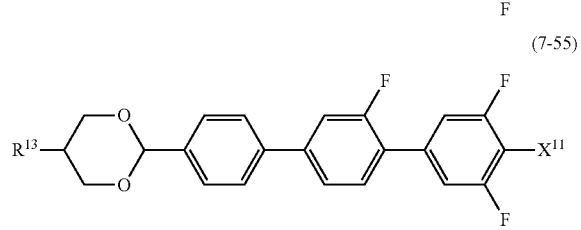

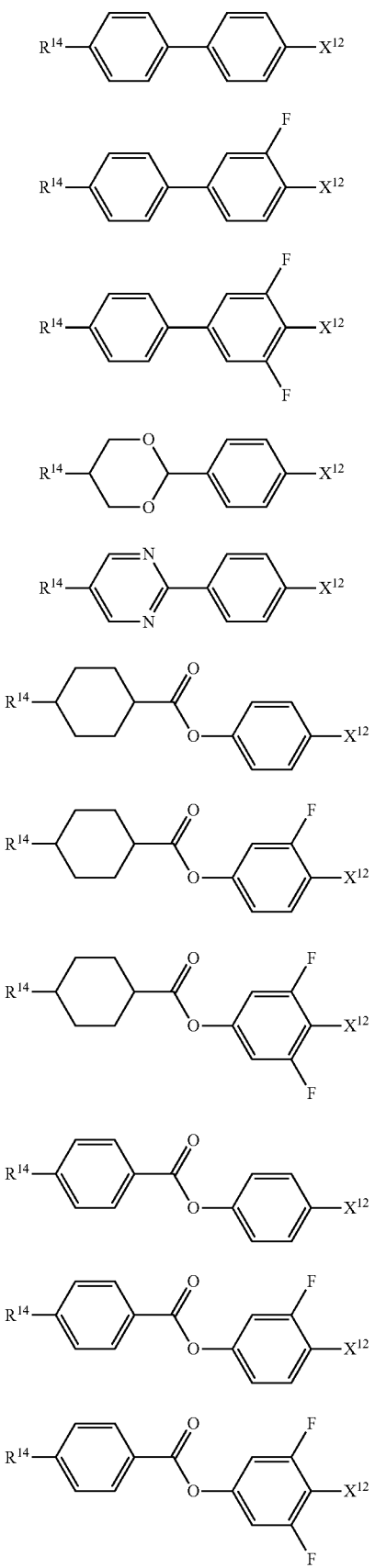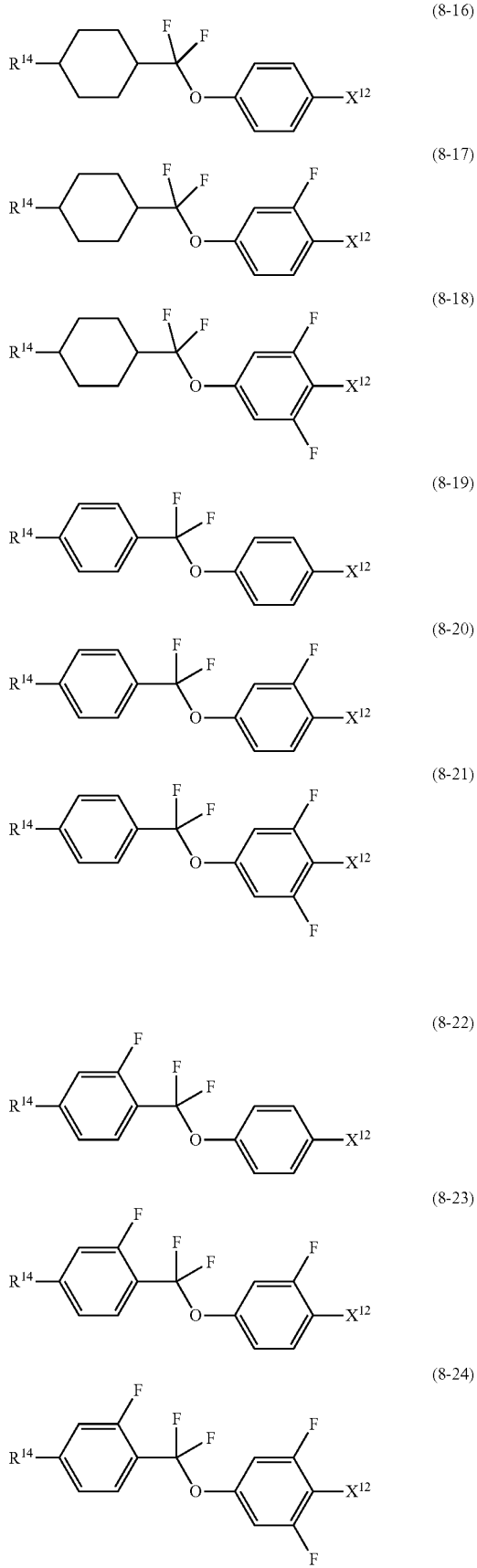

(8-25) through (8-44): chemical structure formulas.

(8-45)
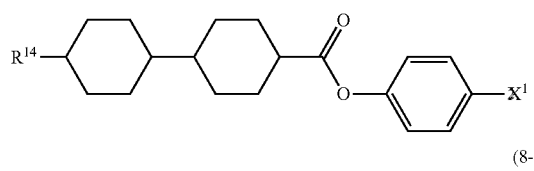
(8-46)
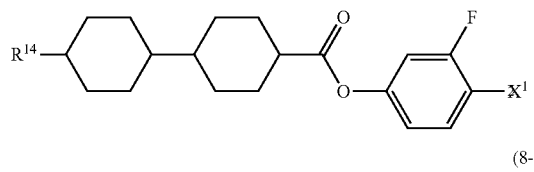
(8-47)
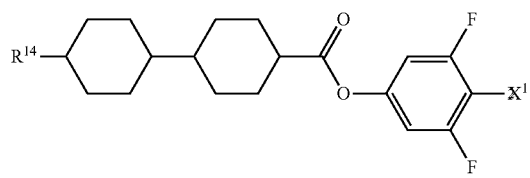
(8-48)
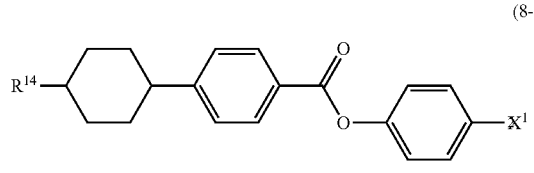
(8-49)
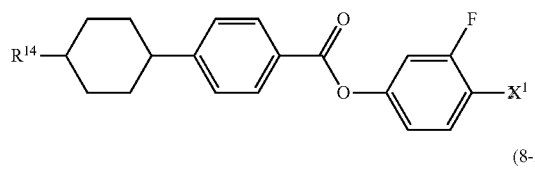
(8-50)
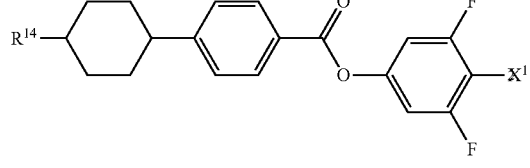
(8-51)
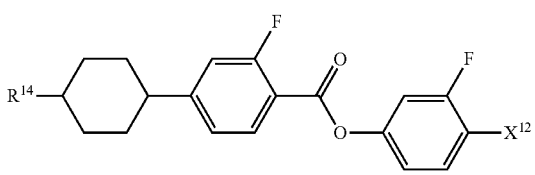
(8-52)
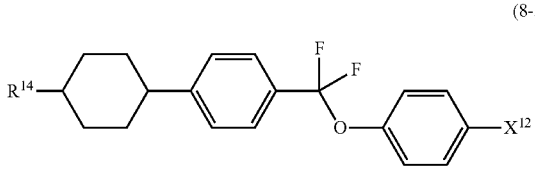
(8-53)
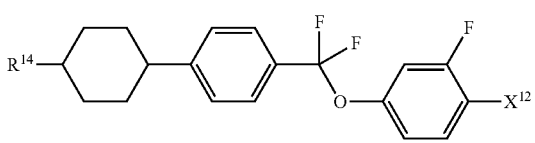
(8-54)
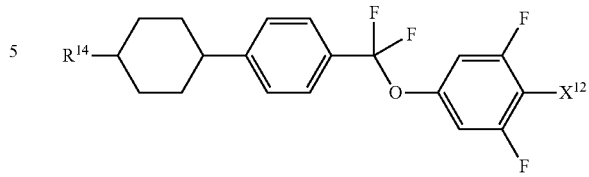
(8-55)
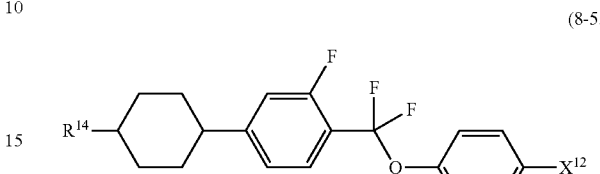
(8-56)
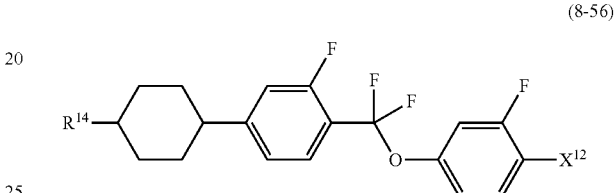
(8-57)
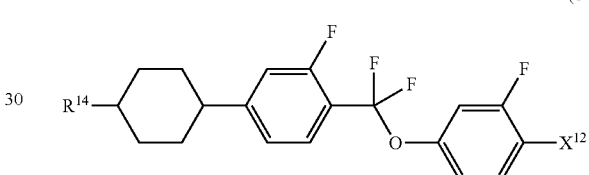
(8-58)
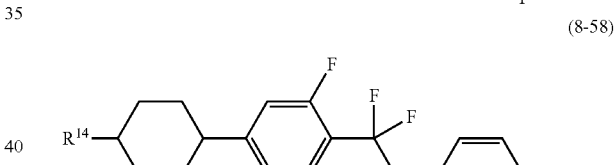
(8-59)
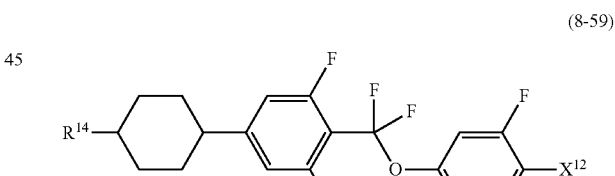
(8-60)
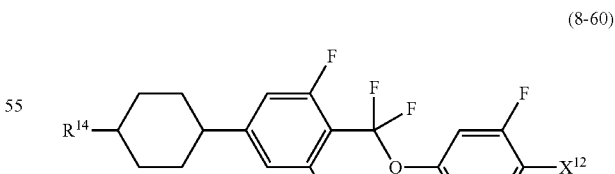
(8-61)
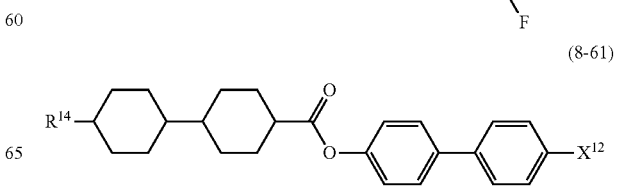

-continued

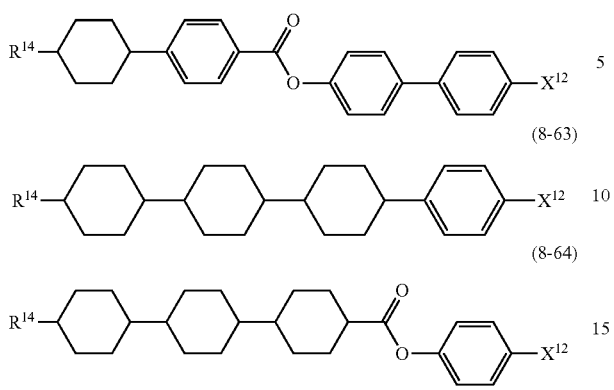

(8-62)
(8-63)
(8-64)

The component D has large positive dielectric anisotropy, and can thus be primarily used for preparing the composition for use in modes such as TN or the like. By addition of the component D, the dielectric anisotropy of the composition can be increased. The component D has an effect of broadening a temperature range of a liquid crystal phase, adjusting viscosity, or adjusting optical anisotropy. The component D is also useful for adjusting the voltage-transmittance curve of the device.

In preparing the composition for use in modes such as TN or the like, the content of the component D is suitably 1 to 99 wt %, preferably 10 to 97 wt %, and more preferably 40 to 95 wt %, based on the weight of the liquid crystal composition. When the component D is added to a composition having negative dielectric anisotropy, the content of the component D is preferably 30 wt % or less based on the weight of the liquid crystal composition. By addition of the component D, the elastic constant of the composition can be adjusted, and the voltage-transmittance curve of the device can be adjusted.

The component E has phenylene in which lateral positions are replaced with two halogens, such as 2,3-difluoro-1,4-phenylene. Preferred examples of these compounds include compounds (9-1) to (9-8), compounds (10-1) to (10-17), compound (11-1), compounds (12-1) to (12-3), compounds (13-1) to (13-11), compounds (14-1) to (14-3), and compounds (15-1) to (15-3). In these compounds, $R^{15}$ and $R^{16}$ are independently alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine; $R^{17}$ is hydrogen, fluorine, alkyl having 1 to 10 carbons, or alkenyl having 2 to 10 carbons, wherein at least one —$CH_2$— in the alkyl and alkenyl is optionally replaced with —O—, and at least one hydrogen in the alkyl and alkenyl is optionally replaced with fluorine.

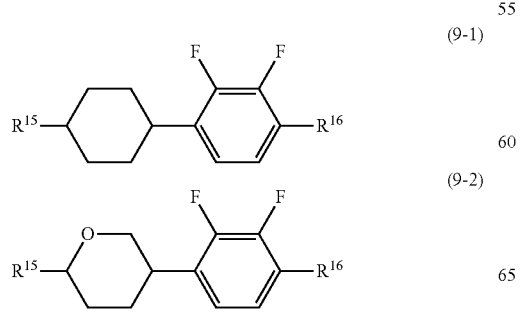

(9-1)
(9-2)

-continued

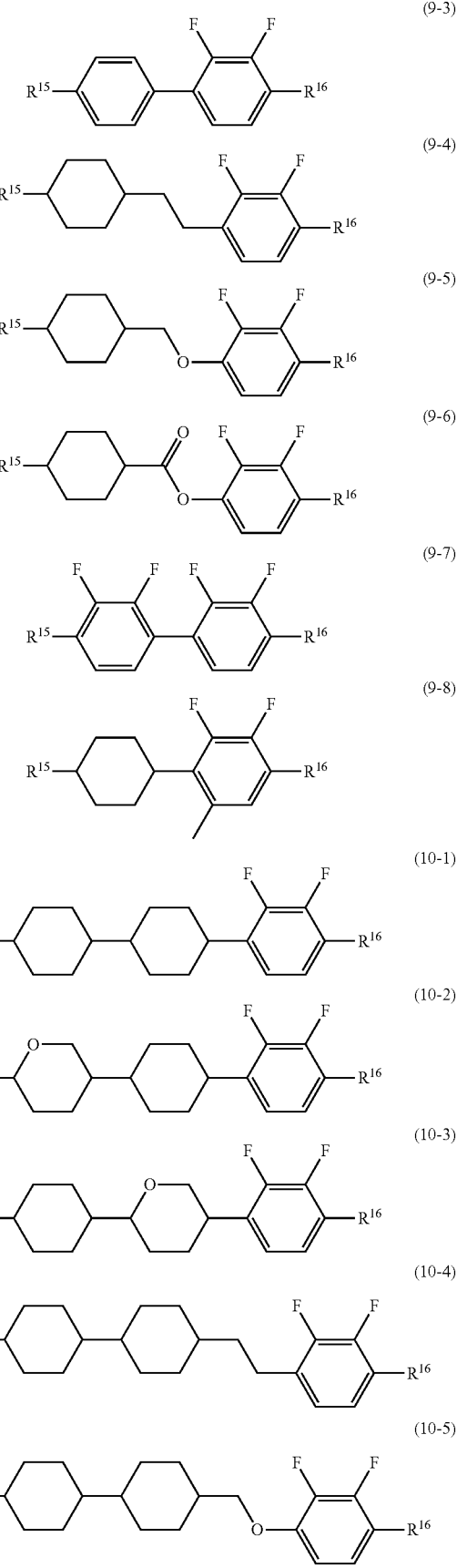

(9-3)
(9-4)
(9-5)
(9-6)
(9-7)
(9-8)
(10-1)
(10-2)
(10-3)
(10-4)
(10-5)

(10-6) 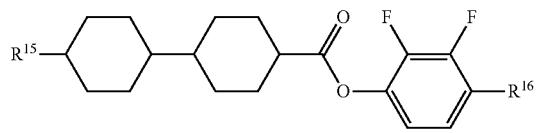
(10-7) 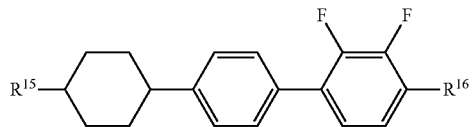
(10-8) 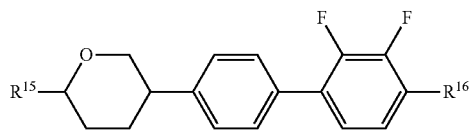
(10-9) 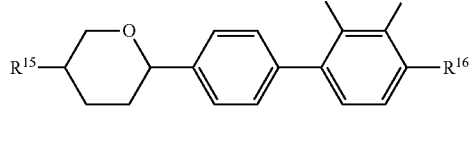
(10-10) 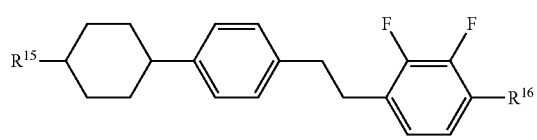
(10-11) 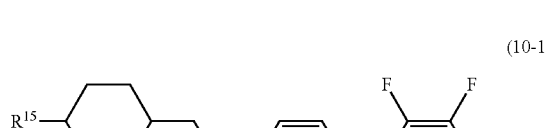
(10-12) 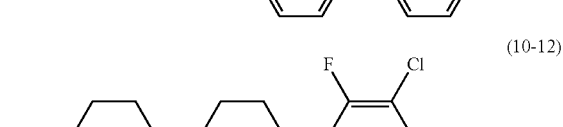
(10-13) 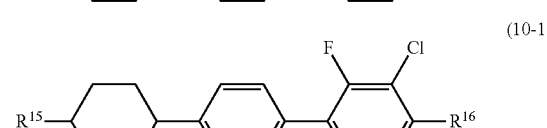
(10-14)
(10-15) 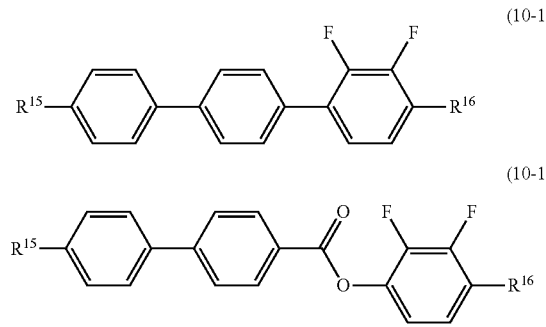
(10-16) 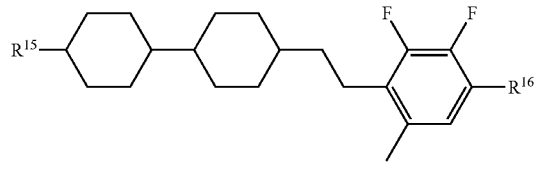
(10-17) 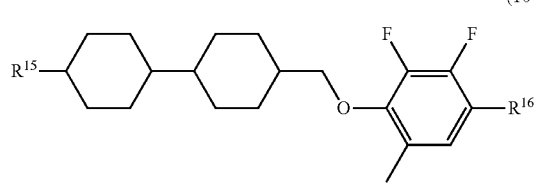
(11-1) 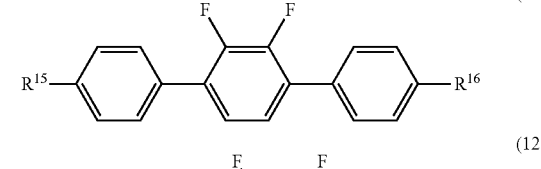
(12-1) 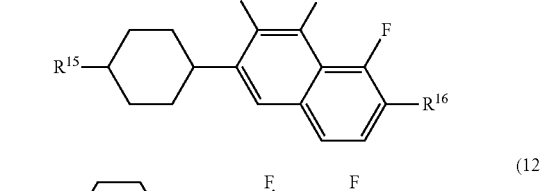
(12-2) 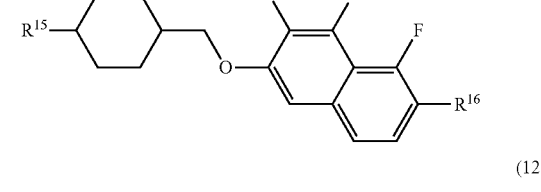
(12-3) 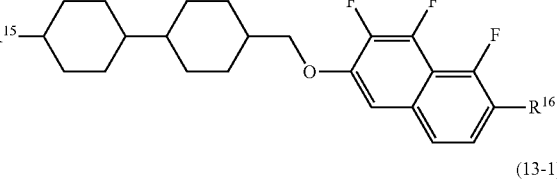
(13-1) 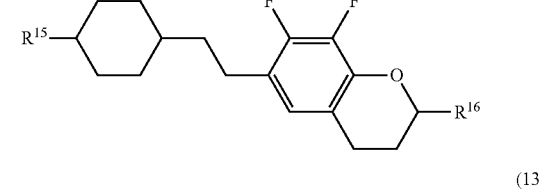
(13-2) 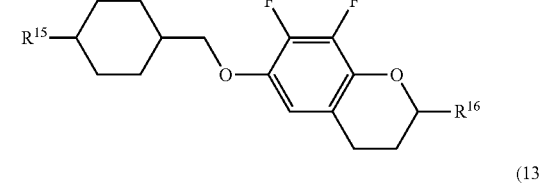
(13-3) 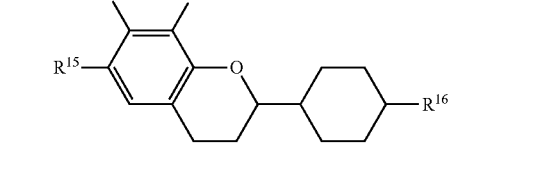

(13-4)
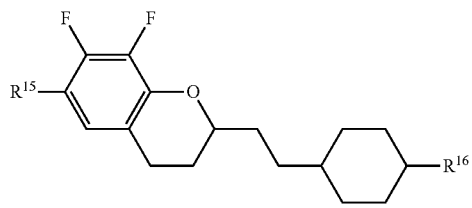

(13-5)
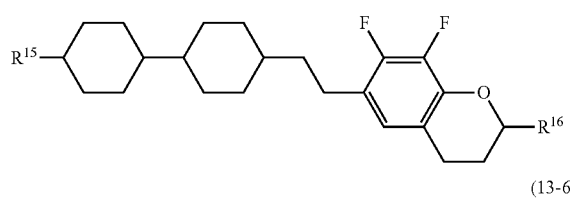

(13-6)
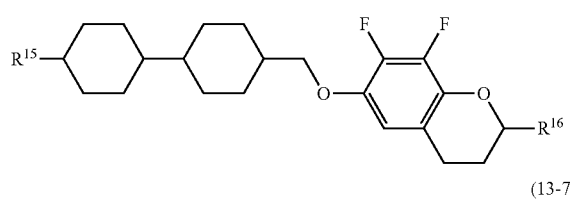

(13-7)
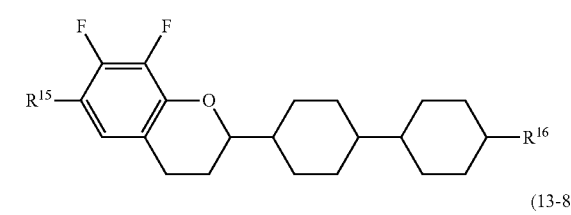

(13-8)
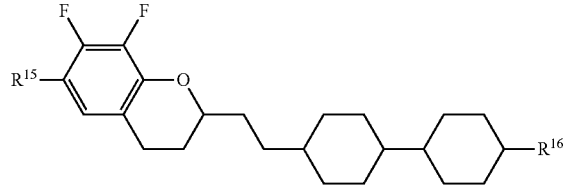

(13-9)
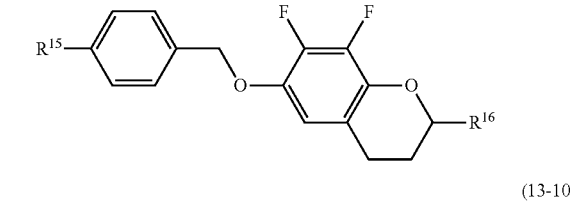

(13-10)
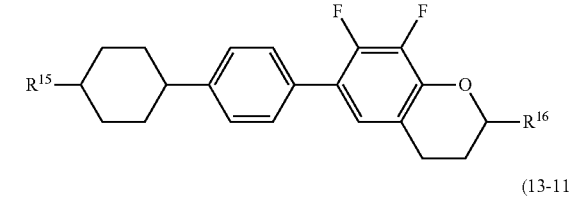

(13-11)
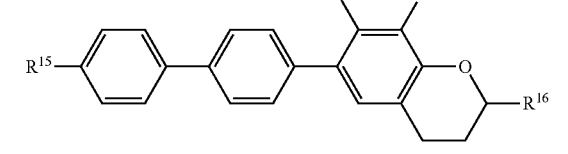

(14-1)
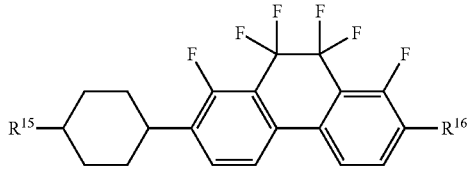

(14-2)
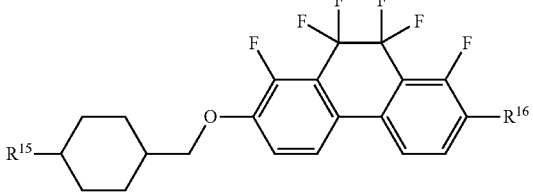

(14-3)
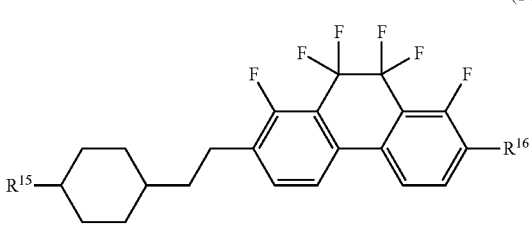

(15-1)
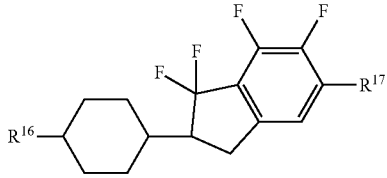

(15-2)
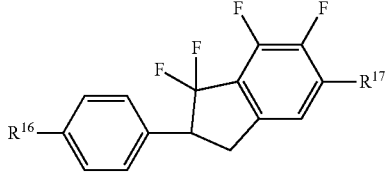

(15-3)
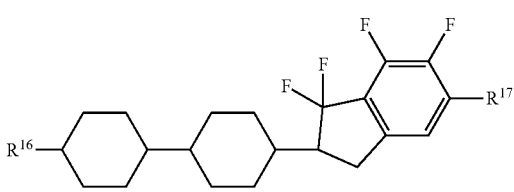

The component E has large negative dielectric anisotropy. These compounds can be used for preparing the composition for use in modes such as IPS, VA, and PSA, etc. As the content of these compounds is increased, the dielectric anisotropy of the composition is increased negatively but the viscosity is increased. Therefore, the content is preferably as low as possible as long as a required value of threshold voltage of the device is satisfied. When considering that the dielectric anisotropy is about −5, the content is preferably 40 wt % or more to perform sufficient voltage driving.

Among these compounds, the compound (9) is a bicyclic compound, and thus mainly has an effect of reducing viscosity, adjusting optical anisotropy or increasing dielectric anisotropy. The compounds (10) and (11) are tricyclic compounds, and thus mainly have an effect of increasing the maximum temperature, increasing optical anisotropy or increasing dielectric anisotropy. The compounds (12) to (15) have an effect of increasing dielectric anisotropy.

In preparing the composition for use in modes such as IPS, VA, and PSA, etc., the content of the compounds (9) to (15) is preferably 40 wt % or more, more preferably 50 to 95 wt %, based on the weight of the liquid crystal composition. When the compounds (9) to (15) are added to a composition having positive dielectric anisotropy, the content of the compounds is preferably 30 wt % or less based on the weight of the liquid crystal composition. By addition of the compounds, the elastic constant of the composition can be adjusted, and the voltage-transmittance curve of the device can be adjusted.

By a suitable combination of the aforementioned components B, C, D and E, a liquid crystal composition that satisfies at least one of characteristics such as high maximum temperature, low minimum temperature, small viscosity, suitable optical anisotropy, large dielectric anisotropy, a suitable elastic constant, and large specific resistance, etc. can be prepared. A liquid crystal compound different from the components B, C, D and E may also be added if necessary.

Preparation of the liquid crystal composition is carried out according to methods such as dissolving necessary component compounds at higher temperatures than room temperature. An additive may be added to the composition according to the use. Examples of the additive include a polymerizable compound, a polymerization initiator, a polymerization inhibitor, an optically active compound, an antioxidant, an ultraviolet absorbent, a light stabilizer, a heat stabilizer, a dye, and a defoamer, etc. Such additives are well-known to persons skilled in the art and have been described in literatures.

In a liquid crystal display device having a polymer sustained alignment (PSA) mode, the composition contains a polymer. The polymerizable compound is added for producing the polymer in the composition. The polymer is produced in the composition by irradiation with ultraviolet light to polymerize the polymerizable compound while a voltage is applied between electrodes. By this method, a suitable pretilt can be obtained, and a liquid crystal display device having shortened response time and improved image burn-in can thus be obtained.

Preferred examples of the polymerizable compound include an acrylate, a methacrylate, a vinyl compound, a vinyloxy compound, propenyl ether, an epoxy compound (oxirane, oxetane), and vinyl ketone. More preferred examples include a compound having at least one acryloyloxy and a compound having at least one methacryloyloxy. More preferred examples also include a compound having both acryloyloxy and methacryloyloxy.

More preferred examples include compounds (M-1) to (M-16). In these compounds, $R^{25}$, $R^{26}$, $R^{27}$ and $R^{28}$ are independently hydrogen or methyl; s, v and x are independently 0 or 1; and t and u are independently an integer of 1 to 10. $L^{21}$, $L^{22}$, $L^{23}$, $L^{24}$, $L^{25}$ and $L^{26}$ are independently hydrogen or fluorine.

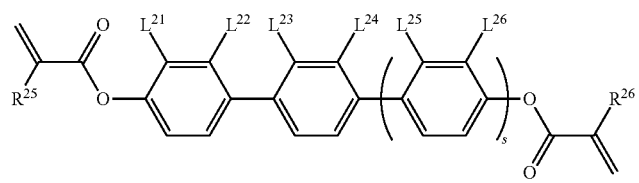

(M-1)

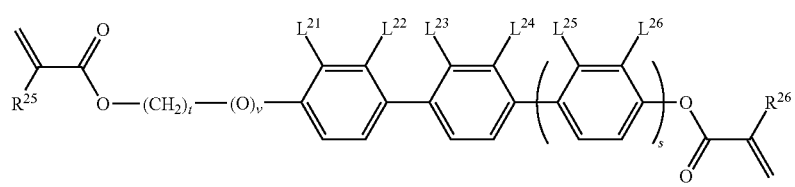

(M-2)

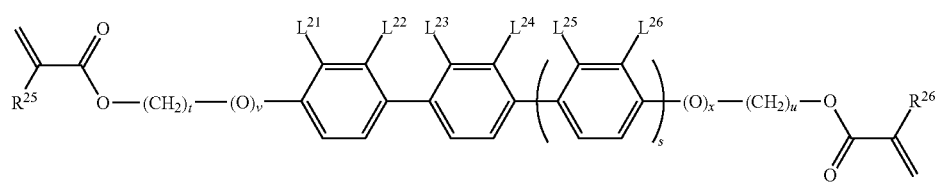

(M-3)

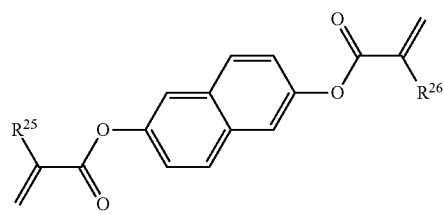

(M-4)

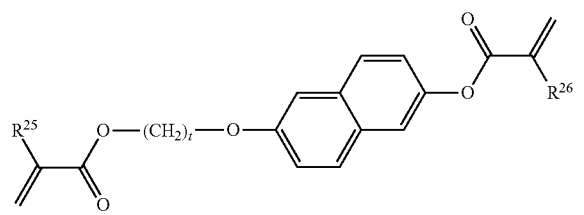

(M-5)

-continued
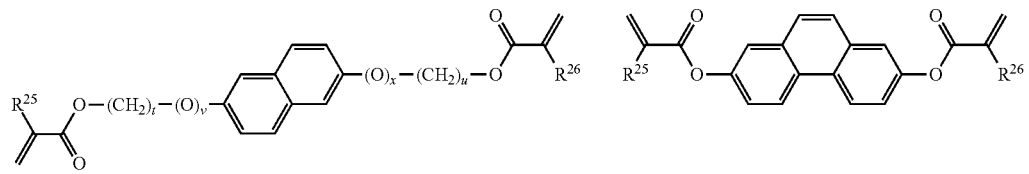
(M-6)
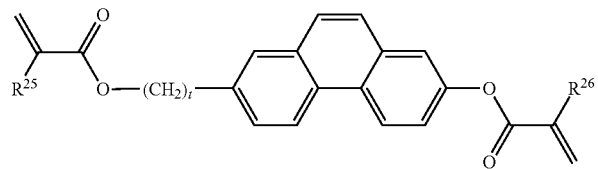
(M-7)
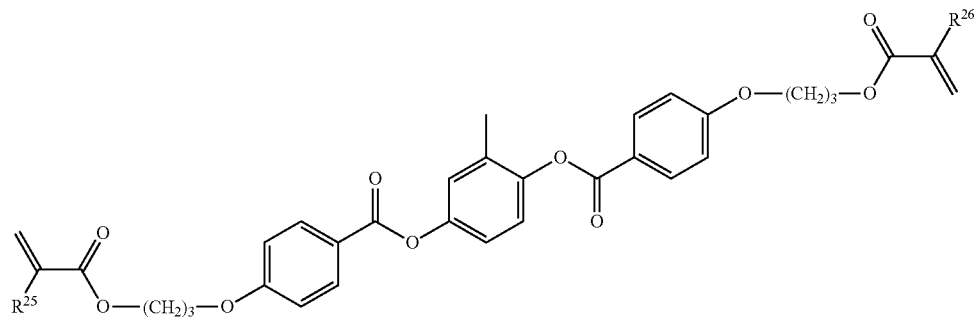
(M-8)
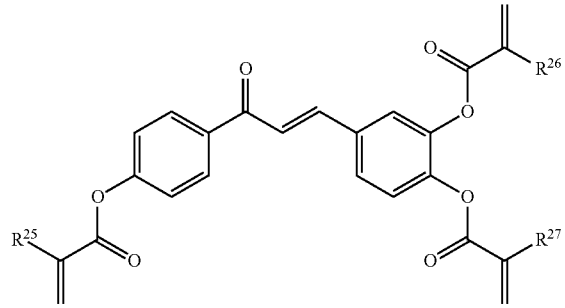
(M-9)
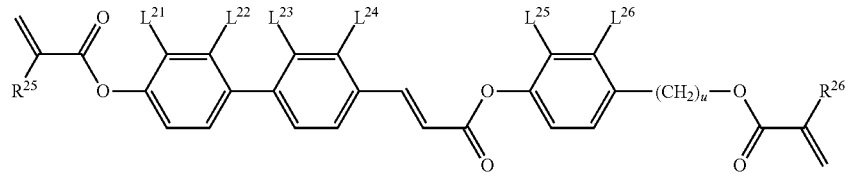
(M-10)
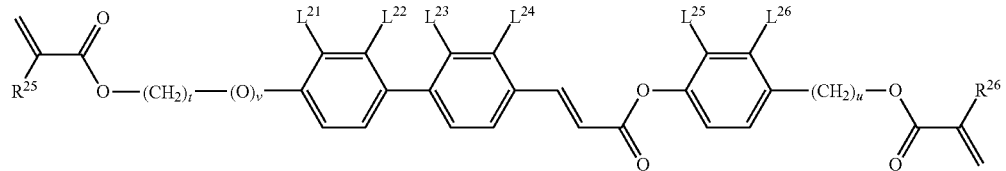
(M-11)
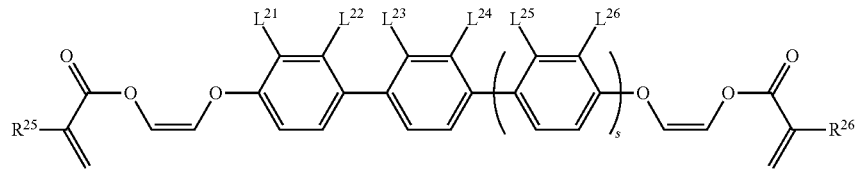
(M-12)
(M-13)

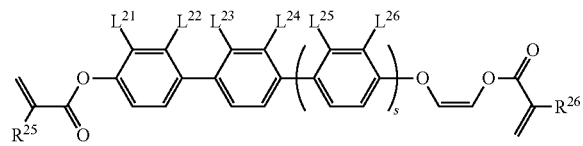
(M-14)

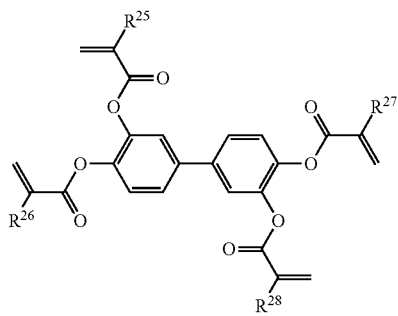
(M-15)

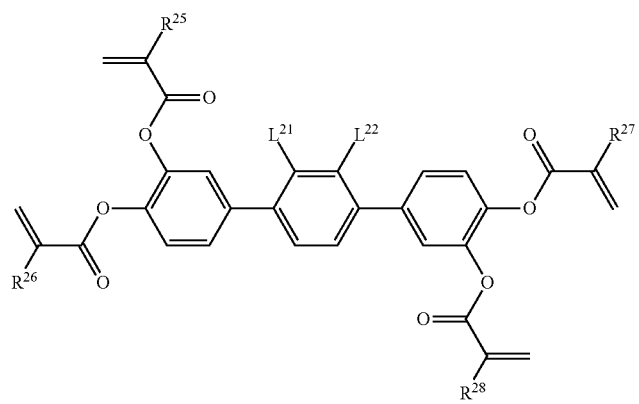
(M-16)

The polymerizable compound can be promptly polymerized by addition of a polymerization initiator. By optimization of a reaction temperature, the amount of remaining polymerizable compound can be reduced. Examples of a photo-radical polymerization initiator include TPO, 1173 and 4265 from Darocur series, and 184, 369, 500, 651, 784, 819, 907, 1300, 1700, 1800, 1850, and 2959 from Irgacure series, all made by BASF.

Additional examples of the photo-radical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone/Michler's ketone mixture, a hexaarylbiimidazole/ mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a 2,4-diethylxanthone/methyl p-dimethylaminobenzoate mixture, and a benzophenone/methyltriethanolamine mixture.

After the photo-radical polymerization initiator is added to the liquid crystal composition, polymerization can be carried out by irradiation with ultraviolet light while an electric field is applied. However, an unreacted polymerization initiator or a decomposition product of the polymerization initiator might cause display defects of the device, such as image burn-in. In order to prevent this, the photopolymerization may also be carried out without addition of the polymerization initiator. The irradiated light preferably has a wavelength of 150 to 500 nm, more preferably 250 to 450 nm, and most preferably 300 to 400 nm.

During storage of the polymerizable compound, a polymerization inhibitor may be added in order to prevent polymerization. The polymerizable compound is usually added to the composition without removing the polymerization inhibitor. Examples of the polymerization inhibitor include hydroquinone, a hydroquinone derivative such as methylhydroquinone, 4-t-butylcatechol, 4-methoxyphenol, and phenothiazine, etc.

The optically active compound has an effect of inducing a helical structure in liquid crystal molecules to give a necessary torsion angle so as to prevent reverse torsion. By addition of the optically active compound, a helical pitch can be adjusted. Two or more optically active compounds may be added for adjusting temperature dependence of the helical pitch. Preferred examples of the optically active compound include the following compounds (Op-1) to (Op-18). In the compound (Op-18), ring J is 1,4-cyclohexylene or 1,4-phenylene, and $R^{28}$ is alkyl having 1 to 10 carbons.

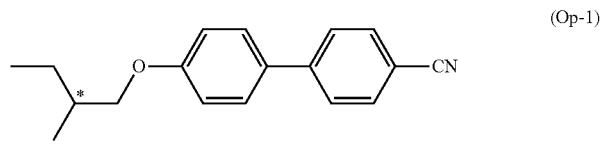
(Op-1)

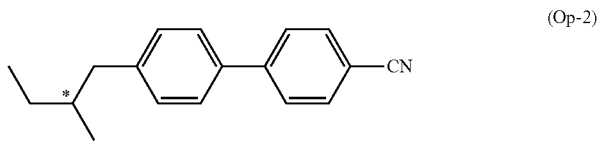
(Op-2)

-continued
(Op-3)
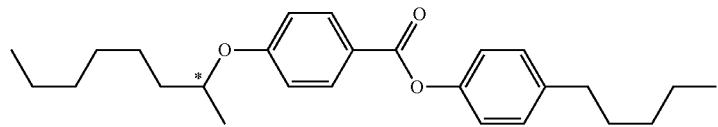
(Op-4)
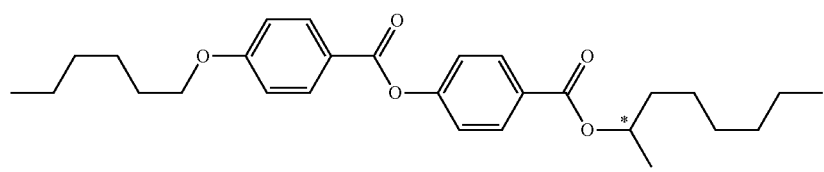
(Op-5)
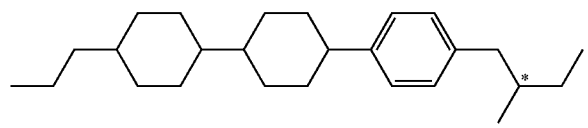
(Op-6)
(Op-7)
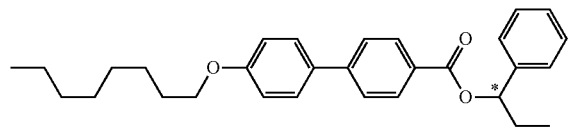
(Op-8)
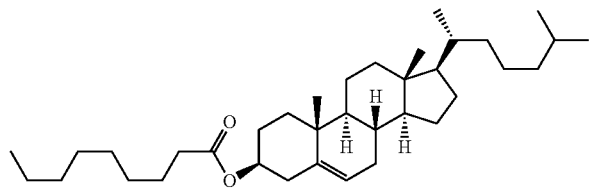
(Op-9)
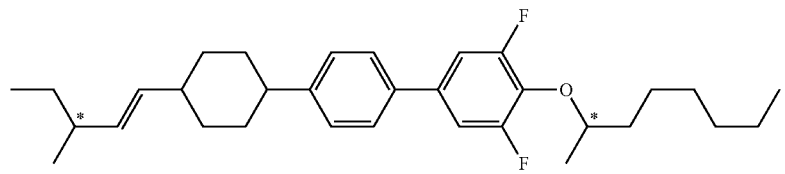
(Op-10)
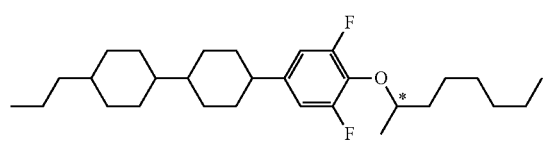
(Op-11)
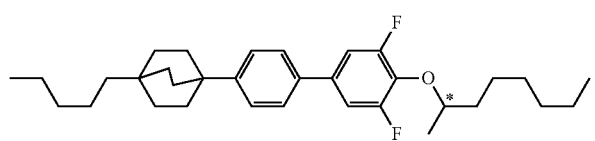
(Op-12)
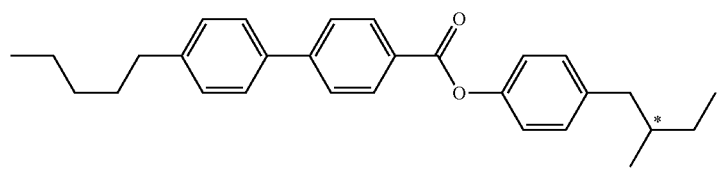
(Op-13)
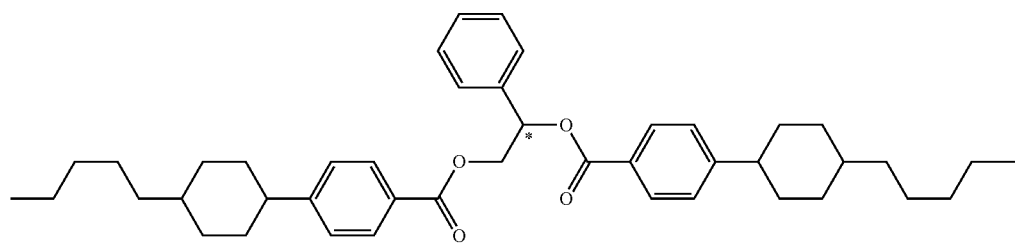

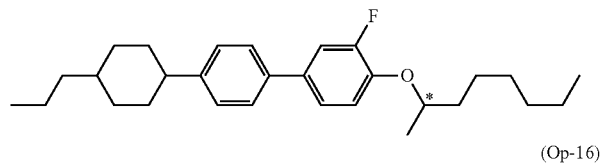 (Op-14)

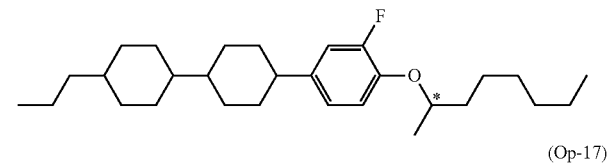 (Op-15)

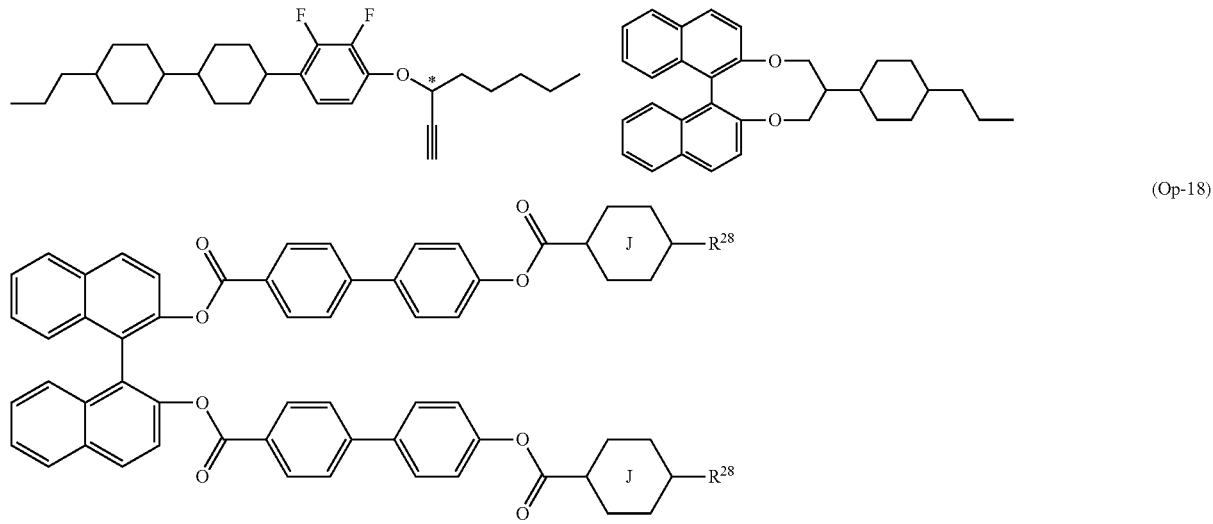

(Op-16)

(Op-17)

(Op-18)

The antioxidant is effective for maintaining a large voltage holding ratio. Preferred examples of the antioxidant include the following compounds (AO-1) and (AO-2), IRGANOX 415, IRGANOX 565, IRGANOX 1010, IRGANOX 1035, IRGANOX 3114, and IRGANOX 1098 (trade name, made by BASF). The ultraviolet absorbent is effective for preventing reduction in the maximum temperature. Preferred examples of the ultraviolet absorbent include a benzophenone derivative, a benzoate derivative, and a triazole derivative, etc. Specific examples thereof include the following compounds (AO-3) and (AO-4), TINUVIN 329, TINUVIN P, TINUVIN 326, TINUVIN 234, TINUVIN 213, TINUVIN 400, TINUVIN 328, and TINUVIN 99-2 (trade name, made by BASF), and 1,4-diazabicyclo[2.2.2]octane (DABCO).

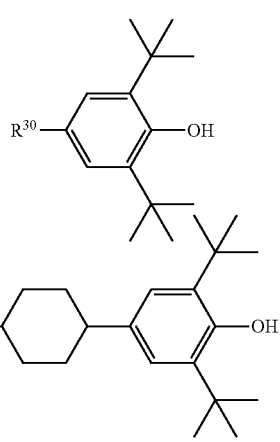

(AO-1)

(AO-2)

-continued

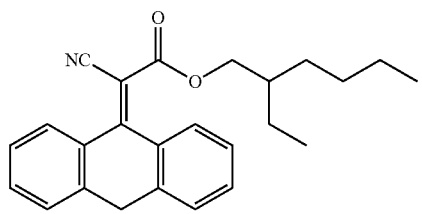 (AO-3)

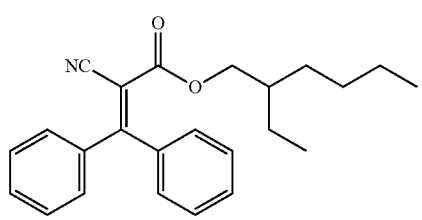 (AO-4)

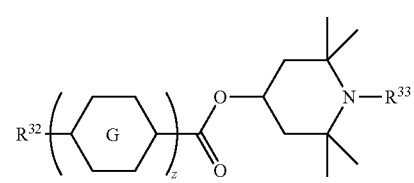

(AO-5)

(AO-6)

In the compound (AO-1), $R^{30}$ is alkyl having 1 to 20 carbons, alkoxy having 1 to 20 carbons, $-COOR^{31}$ or —$CH_2CH_2COOR^{31}$, and $R^{31}$ herein is alkyl having 1 to 20 carbons. In the compound (AO-2), $R^{32}$ is alkyl having 1 to 20 carbons. In the compound (AO-5), $R^{32}$ is alkyl having 1 to 20 carbons; $R^{33}$ is hydrogen, methyl or O. (oxygen radical); ring G is 1,4-cyclohexylene or 1,4-phenylene; and Z is 1, 2, or 3.

The light stabilizer such as an amine having steric hindrance is preferred for maintaining a large voltage holding ratio. Preferred examples of the light stabilizer include the above compounds (AO-5) and (AO-6), TINUVIN 144, TINUVIN 765 and TINUVIN 770DF (trade name, made by BASF). The heat stabilizer is also effective for maintaining a large voltage holding ratio, and preferred examples thereof include IRGAFOS 168 (trade name, made by BASF). A dichroic dye such as an azo dye, an anthraquinone dye or the like is added to the composition in order to suit a device in a guest host (GH) mode. The defoamer is effective for preventing foaming. Preferred examples of the defoamer include dimethyl silicone oil and methyl phenyl silicone oil, etc.

4. Liquid Crystal Display Device

The liquid crystal composition can be used in a liquid crystal display device having an operating mode such as PC, TN, STN, OCB, or PSA, etc. and driven by an active matrix (AM) method. The composition can also be used in a liquid crystal display device having an operating mode such as PC, TN, STN, OCB, VA, or IPS, etc. and driven by a passive matrix (PM) method. These devices using the AM and PM methods may be of any of a reflective type, a transmissive type and a transflective type.

The composition is also applicable to a nematic curvilinear aligned phase (NCAP) device in which the composition is microencapsulated. The composition can also be used in a polymer dispersed liquid crystal display (PDLCD) device or a polymer network liquid crystal display (PNLCD) device. In these compositions, a large amount of liquid crystal compounds are added. On the other hand, when the polymerizable compound is added in an amount of about 10 wt % or less based on the weight of the liquid crystal composition, a liquid crystal display device in the PSA mode is produced. A preferred ratio is about 0.1 to 2 wt %, and a more preferred ratio is about 0.2 to 1.0 wt %. The device in the PSA mode can be driven by methods such as an active matrix (AM) method and a passive matrix (PM) method. Such a device may be of any of a reflective type, a transmissive type and a transflective type.

EXAMPLES

The invention is further described in details according to examples (including use examples). The invention includes a mixture of a composition of Use Example 1 and a composition of Use Example 2. The invention also includes a composition prepared by mixing at least two compositions of the use examples. The invention is not limited to these examples.

1. Examples of Compound (1)

The compound (1) was synthesized by procedures shown in synthesis examples. Unless otherwise specified, the reactions were performed under a nitrogen atmosphere. The synthesized compound was identified by methods such as NMR analysis, etc. Characteristics of the compound were measured by methods described below.

NMR Analysis

DRX-500 made by Bruker BioSpin K.K. was used for the measurement. In the measurement of $^1$H-NMR, a sample was dissolved in a deuterated solvent such as $CDCl_3$, and measured at 500 MHz at room temperature in 16 times of accumulation. Tetramethylsilane was used as the internal standard. The measurement of $^{19}$F-NMR was carried out using $CFCl_3$ as the internal standard in 24 times of accumulation. In the description of the nuclear magnetic resonance spectrum, "s" denotes singlet, "d" denotes doublet, "t" denotes triplet, "q" denotes quartet, "quin" denotes quintet, "sex" denotes sextet, "m" denotes multiplet, and "br" denotes broad.

GC Analysis

GC-2010 Gas Chromatograph made by Shimadzu Corporation was used for the measurement. The capillary column DB-1 (length=60 m, inner diameter=0.25 mm, film thickness=0.25 μm) made by Agilent Technologies Inc. was used as the column. The carrier gas was helium, and its flow rate was adjusted to 1 ml/min. The sample evaporation chamber was set at 300° C., and the detector (flame ionization detector, FID) was set at 300° C. The sample was dissolved in acetone so as to prepare a solution of 1 wt %, and then 1 μl of the obtained solution was poured into the sample evaporation chamber. The GCsolution system made by Shimadzu Corporation or the like was used as the recorder.

HPLC Analysis

Prominence (LC-20AD; SPD-20A) made by Shimadzu Corporation was used for the measurement. YMC-Pack ODS-A (length=150 mm, inner diameter=4.6 mm, particle diameter=5 μm) made by YMC Co., Ltd. was used as the column. A mixture obtained by properly mixing acetonitrile and water was used as the eluent. A UV detector, an RI detector, or a Corona detector or the like was properly used as the detector. When the UV detector was used, the detection wavelength was 254 nm. The sample was dissolved in acetonitrile so as to prepare a solution of 0.1 wt %, and 1 μL of the solution was introduced to the sample chamber. C-R7Aplus made by Shimadzu Corporation was used as the recorder.

Ultraviolet-Visible Spectroscopic Analysis

PharmaSpec UV-1700 made by Shimadzu Corporation was used for the measurement. The detection wavelength was 190 nm to 700 nm. The sample was dissolved in acetonitrile so as to prepare a 0.01 mmol/L solution, and the solution was placed in a quartz cell (optical path length=1 cm) and then measured.

Measurement Sample

A compound itself was used as a sample when the phase structure and the transition temperature (clearing point, melting point, polymerization start temperature, etc.) were measured. A mixture of a compound and a mother liquid crystal was used as a sample when characteristics such as the maximum temperature of a nematic phase, viscosity, optical anisotropy, and dielectric anisotropy, etc. were measured.

Measurement Method

The characteristics were measured by the following methods. Most of these methods were those described in the JEITA Standards (JEITA•ED-2521B) deliberated and established by the Japan Electronics and Information Technology Industries Association (JEITA), or modifications of the same. No thin-film transistor (TFT) was attached to a TN device used for the measurement.

(1) Phase Structure (1) The sample was placed on a hot plate (FP52 Hot Stage made by Mettler Toledo International Inc.) of a melting point apparatus equipped with a polarizing microscope, and a state of phase and a change thereof were observed with the polarizing microscope while the sample was heated at a rate of 3° C./min, and a phase type was specified.

(2) Transition Temperature (° C.)

A scanning calorimeter, Diamond DSC System made by PerkinElmer, Inc., or a high sensitivity differential scanning calorimeter, X-DSC7000 made by SII NanoTechnology Inc., was used for the measurement. The sample was heated and then cooled at a rate of 3° C./min. A starting point of an endothermic peak or an exothermic peak caused by a phase change of the sample was calculated by extrapolation, and the phase transition temperature was determined. A melting point and a polymerization start temperature of a compound were also measured using this apparatus. The temperature at which a compound changes from solid to a liquid crystal phase such as smectic phase or nematic phase is sometimes simply referred to as "minimum temperature of a liquid crystal phase." The temperature at which a compound changes from a liquid crystal phase to liquid is sometimes simply referred to as "clearing point."

Crystals were expressed as C. When types of the crystals were distinguishable, the crystals were expressed as $C_1$ or $C_2$. The smectic phase was expressed as S and the nematic phase as N. When a smectic A phase, a smectic B phase, a smectic C phase or a smectic F phase was distinguishable in the smectic phases, it was expressed as $S_A$, $S_B$, $S_C$ or $S_F$. A liquid (isotropic) was expressed as I. A transition temperature was expressed as, e.g., "C 50.0 N 100.0 I." This means that the transition temperature from crystal to a nematic phase is 50.0° C., and the transition temperature from a nematic phase to liquid is 100.0° C.

(3) Maximum Temperature of Nematic Phase ($T_{NI}$ or NI; ° C.)

The sample was placed on a hot plate of a melting point apparatus equipped with a polarizing microscope and was heated at a rate of 1° C./min. The temperature at which a part of the sample changed from a nematic phase to an isotropic liquid was measured. The maximum temperature of the nematic phase is sometimes simply referred to as "maximum temperature." When the sample was a mixture of the compound (1) and a mother liquid crystal, the maximum temperature was expressed by the symbol $T_{NI}$. When the sample was a mixture of the compound (1) and a compound such as the component B, C or D, the maximum temperature was expressed by the symbol NI.

(4) Minimum Temperature of Nematic Phase ($T_C$; ° C.)

The sample having a nematic phase was kept in a freezer at 0° C., −10° C., −20° C., −30° C., and −40° C. for 10 days, and then observed for the liquid crystal phase. For example, when the sample maintained a nematic phase at −20° C. and changed to crystal or a smectic phase at −30° C., the $T_C$ was recorded as "20° C." The minimum temperature of the nematic phase is sometimes simply referred to as "minimum temperature."

(5) Viscosity (Bulk Viscosity; η; Measured at 20° C.; mPa·s)

An E-type rotational viscometer made by Tokyo Keiki Inc. was used for the measurement.

(6) Optical Anisotropy (Refractive Index Anisotropy; Measured at 25° C.; Δn)

The measurement was carried out using light of 589 nm with an Abbe refractometer having a polarizing plate mounted on ocular lens. The surface of the main prism was rubbed in a direction, and then the sample was dripped onto the main prism. The refractive index (n//) was measured when the direction of polarized light was parallel to that of the rubbing, and the refractive index (n⊥) was measured when the direction of polarized light was perpendicular to that of the rubbing. The value of optical anisotropy (Δn) was calculated from an equation of "Δn=n//−n⊥."

(7) Specific Resistance (ρ; Measured at 25° C.; Ω Cm)

1.0 mL of the sample was poured into a vessel equipped with electrodes. DC voltage (10 V) was applied to the vessel, and the DC current after 10 seconds was measured. The specific resistance was calculated from the following equation: (specific resistance)=[(voltage)×(electric capacity of vessel)]/[(DC current)×(dielectric constant in vacuum)].

(8) Voltage Holding Ratio (VHR-1; Measured at 25° C.; %)

The TN device used for the measurement had a polyimide alignment film, and had a distance (cell gap) of 5 μm between two glass substrates. The sample was placed into the device, and then the device was sealed with an adhesive curable on irradiation with ultraviolet light. The device was charged by applying a pulse voltage (60 microseconds at 5 V). A decaying voltage was measured for 16.7 milliseconds with a high-speed voltmeter, and an area A between a voltage curve and a horizontal axis per unit cycle was calculated. An area B was an area without decay. A voltage holding ratio was expressed by a percentage of the area A relative to the area B.

(9) Voltage Holding Ratio (VHR-2; Measured at 80° C.; %)

A voltage holding ratio was measured by the same procedures as above except that the measurement was carried out at 80° C. instead of 25° C. The results obtained were expressed by the symbol VHR-2.

(10) Voltage holding ratio (VHR-3; measured at 25° C.; %): A voltage holding ratio was measured after irradiation with ultraviolet light, and stability to ultraviolet light was evaluated. The TN device used for the measurement had a polyimide alignment film, and had a cell gap of 5 μm. The sample was poured into the device, and the device was irradiated with light for 20 minutes. The light source was an extra-high pressure mercury lamp, USH-500D (made by Ushio Inc.), and a distance between the device and the light source was 20 cm. In the measurement of VHR-3, a decaying voltage was measured for 16.7 milliseconds. A composition having a large VHR-3 has great stability to ultraviolet light. The VHR-3 is preferably 90% or more, more preferably 95% or more.

(11) Voltage holding ratio (VHR-4; measured at 25° C.; %): A TN device into which the sample was poured was heated in a constant-temperature bath at 80° C. for 500 hours, and then stability to heat was evaluated by measuring a voltage holding ratio. In the measurement of VHR-4, a decaying voltage was measured for 16.7 milliseconds. A composition having a large VHR-4 has great stability to heat.

Methods for measuring the characteristics may differ between with a sample having positive dielectric anisotropy and with a sample having negative dielectric anisotropy. The measurement methods for the case with positive dielectric anisotropy are described in items (12a) to (16a). Items (12b) to (16b) describe the case with negative dielectric anisotropy.

(12a) Viscosity (Rotational Viscosity; Yl; Measured at 25° C.; mPa·s):

Positive dielectric anisotropy: the measurement was carried out following the method described in M. Imai et al., Molecular Crystals and Liquid Crystals, Vol. 259, 37 (1995). The sample was placed into a TN device with a twist angle of 0 degree and a distance (cell gap) of 5 μm between two glass substrates. The device was applied with a voltage in a range of 16 to 19.5 V, stepwise by 0.5 V. After a period of 0.2 second with no application of voltage, a voltage application was repeated with a rectangular wave (rectangular pulse of 0.2 second) followed by a period of 2 seconds of no voltage. Peak current and peak time of a transient current resulting from the application of the voltage were measured. The value of rotational viscosity was obtained according to these measured values and Equation (8) on page 40 of the paper of M. Imai et al. The value of dielectric anisotropy required for this calculation was obtained by the method described below using the device by which the rotation viscosity was measured.

(12b) Viscosity (Rotational Viscosity; Yl; Measured at 25° C.; mPa·s):

Negative dielectric anisotropy: the measurement was carried out following the method described in M. Imai et al., Molecular Crystals and Liquid Crystals, Vol. 259, 37 (1995). The sample was placed into a VA device with a distance (cell gap) of 20 μm between two glass substrates. The device was applied with a voltage in a range of 39 to 50 V, stepwise by 1 V. After a period of 0.2 second with no application of voltage, a voltage application was repeated with a rectangular wave (rectangular pulse of 0.2 second) followed by a period of 2 seconds of no voltage. The peak current and the peak time of a transient current resulting from the application of the voltage were measured. The value of rotational viscosity was obtained according to these measured values and Equation (8) on page 40 of the paper of M. Imai et al. The dielectric anisotropy value required for this calculation was measured as described in the following section of "Dielectric anisotropy."

(13a) Dielectric Anisotropy (Δ∈; Measured at 25° C.):

Positive dielectric anisotropy: the sample was placed into a TN device with a distance (cell gap) of 9 μm between two glass substrates and a twist angle of 80 degrees. The device was applied with a sine wave (10 V, 1 kHz), and the dielectric constant (∈//) in the major-axis direction of the liquid crystal molecule was measured after 2 seconds. The device was applied with a sine wave (0.5 V, 1 kHz), and the dielectric constant (∈⊥) in the minor-axis direction of the liquid crystal molecule was measured after 2 seconds. The value of dielectric anisotropy was calculated from an equation of "Δ∈=∈//−∈⊥."

(13b) Dielectric Anisotropy (as; Measured at 25° C.):

Negative dielectric anisotropy: the value of dielectric anisotropy was calculated from the equation of "Δ∈=∈//−⊥." The dielectric constant (∈// and ∈⊥) was measured as follows.

1) Measurement of dielectric constant (∈//): an ethanol (20 mL) solution of octadecyltriethoxysilane (0.16 mL) was coated on a sufficiently washed glass substrate. The glass substrate was rotated by a spinner, and then heated at 150° C. for 1 hour. The sample was placed into a VA device with a distance (cell gap) of 4 μm between two glass substrates, and the device was sealed with an adhesive curable on irradiation with ultraviolet light. The device was applied with a sine wave (0.5 V, 1 kHz), and the dielectric constant (∈//) in the major-axis direction of the liquid crystal molecule was measured after 2 seconds.

2) Measurement of dielectric constant (∈⊥): a polyimide solution was coated on a sufficiently washed glass substrate. The glass substrate was burned, and then the resulting alignment film was subjected to rubbing. The sample was placed into a TN device with a distance (cell gap) of 9 μm between two glass substrates and a twist angle of 80 degrees. The device was applied with a sine wave (0.5 V, 1 kHz), and the dielectric constant (∈⊥) in the minor-axis direction of the liquid crystal molecule was measured after 2 seconds.

(14a) Elastic Constant (K; Measured at 25° C.; pN)

Positive dielectric anisotropy: an LCR meter, HP 4284A made by Yokogawa-Hewlett-Packard, Ltd., was used for the measurement. The sample was placed into a horizontal alignment element with a distance (cell gap) of 20 μm between two glass substrates. The device was applied with an electric charge of 0 to 20 V, and electrostatic capacity and applied voltage were measured. The measured values of electrostatic capacity (C) and applied voltage (V) were fitted to Equation (2.98) and Equation (2.101) on page 75 of the "Liquid Crystal Device Handbook" (Nikkan Kogyo Shimbun, Ltd.), and values of $K_{11}$ and $K_{33}$ were obtained from Equation (2.99). Next, $K_{22}$ was calculated from Equation (3.18) on page 171 using the previously obtained values of $K_{11}$ and $K_{33}$. The elastic constant K was an average value of $K_{11}$, $K_{22}$ and $K_{33}$ thus obtained.

(14b) Elastic Constant ($K_{11}$ and $K_{33}$; Measured at 25° C.; pN)

Negative dielectric anisotropy: an elastic constant measurement system, Model EC-1 made by Toyo Corporation, was used for the measurement. The sample was placed into a vertical alignment element with a distance (cell gap) of 20 μm between two glass substrates. The device was applied with an electric charge of 20 to 0 V, and electrostatic capacity and applied voltage were measured. The values of electrostatic capacity (C) and applied voltage (V) were fitted to Equation (2.98) and Equation (2.101) on page 75 of the "Liquid Crystal Device Handbook" (Nikkan Kogyo Shimbun, Ltd.), and the value of elastic constant was obtained from Equation (2.100).

(15a) Threshold Voltage (Vth; Measured at 25° C.; V)

Positive dielectric anisotropy: a luminance meter, Model LCD5100 made by Otsuka Electronics Co., Ltd., was used for the measurement. The light source was a halogen lamp. The sample was placed into a TN device in a normally white mode with a distance (cell gap) of 0.45/Δn (μm) between two glass substrates and a twist angle of 80 degrees. A voltage (32 Hz, rectangular wave) applied to the device was increased stepwise from 0 V to 10 V at an increment of 0.02 V. On this occasion, the device was irradiated with light in the vertical direction, and the amount of light passing through the device was measured. A voltage-transmittance curve was plotted in a manner that the transmittance was 100% when the amount of light became the maximum and the transmittance was 0% when the amount of light became the minimum. The threshold voltage was the voltage corresponding to the transmittance of 90%.

(15b) Threshold Voltage (Vth; Measured at 25° C.; V)

Negative dielectric anisotropy: a luminance meter, Model LCD5100 made by Otsuka Electronics Co., Ltd., was used for the measurement. The light source was a halogen lamp. The sample was placed into a VA device in a normally black mode with a distance (cell gap) of 4 μm between two glass substrates and an antiparallel rubbing direction, and the device was sealed with an adhesive curable on irradiation with ultraviolet light. A voltage (60 Hz, rectangular wave) applied to the device was increased stepwise from 0 V to 20 V at an increment of 0.02 V. On this occasion, the device was irradiated with light in the vertical direction, and the amount of light passing through the device was measured. A voltage-transmittance curve was plotted in a manner that the transmittance was 100% when the amount of light became the maximum and the transmittance was 0% when the amount of light became the minimum. The threshold voltage was the voltage corresponding to the transmittance of 10%.

(16a) Response Time (r; Measured at 25° C.; Ms)

Positive dielectric anisotropy: a luminance meter, Model LCD5100 made by Otsuka Electronics Co., Ltd., was used for the measurement. The light source was a halogen lamp. The low-pass filter was set at 5 kHz. The sample was placed into a TN device in a normally white mode with a distance (cell gap) of 5.0 μm between two glass substrates and a twist angle of 80 degrees. A rectangular wave (60 Hz, 5 V, 0.5 second) was applied to the device. On this occasion, the device was irradiated with light in the vertical direction, and the amount of light passing through the device was measured. The transmittance was regarded as 100% when the amount of light became the maximum and the transmittance was regarded as 0% when the amount of light became the minimum. Rise time (ir; millisecond) was the time required for a change in transmittance from 90% to 10%. Fall time (if; millisecond) was the time required for a change in transmittance from 10% to 90%. The response time was the sum of the rise time and the fall time thus obtained.

(16b) Response Time (τ; Measured at 25° C.; ms)

Negative dielectric anisotropy: a luminance meter, Model LCD5100 made by Otsuka Electronics Co., Ltd., was used for the measurement. The light source was a halogen lamp. The low-pass filter was set at 5 kHz. The sample was placed into a PVA device in a normally black mode with a distance (cell gap) of 3.2 μm between two glass substrates and an antiparallel rubbing direction. The device was sealed with an adhesive curable on irradiation with ultraviolet light. A voltage that was a little higher than the threshold voltage was applied to the device for 1 minute, and then, the device was irradiated with ultraviolet light of 23.5 mW/cm² for 8 minutes while a voltage of 5.6 V was applied. A rectangular wave (60 Hz, 10 V, 0.5 second) was applied to the device. On this occasion, the device was irradiated with light in the vertical direction, and the amount of light passing through the device was measured. The transmittance was regarded as 100% when the amount of light became the maximum and the transmittance was regarded as 0% when the amount of light became the minimum. The response time was the time required for a change in transmittance from 90% to 10% (fall time; millisecond).

Synthesis Example 1

A compound (1-2-1) was synthesized according to the following synthesis scheme.

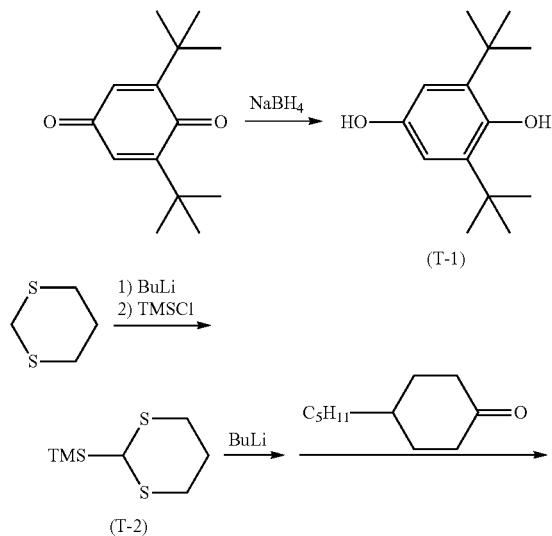

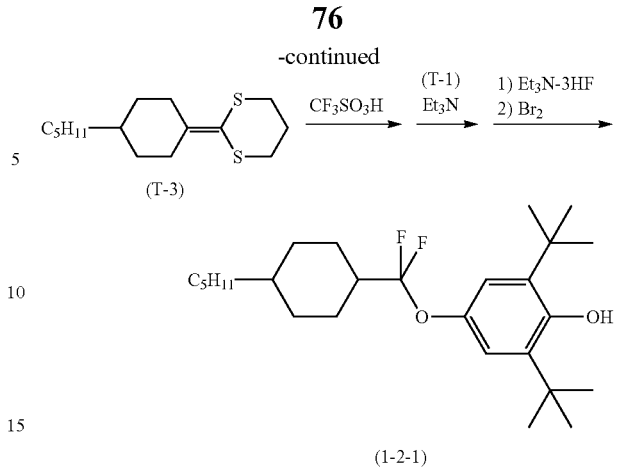

First Process: Synthesis of Compound (T-1)

Sodium borohydride (6.5 g, 172 mmol) was suspended in tetrahydrofuran (250 mL). A tetrahydrofuran (250 mL) solution of 2,6-t-butylcyclohexa-2,5-diene-1,4-dione (50 g, 227 mmol) was dripped in at 25° C., and the resultant was further stirred for 1 hour. After the reaction was completed, the reaction mixture was poured into a mixture of acetone (100 mL) and water (500 mL), and methyl t-butyl ether (500 mL) was added. The resultant was subjected to separation, and the water layer was extracted with methyl t-butyl ether (500 mL, twice). The combined organic layers were washed with a saturated sodium chloride aqueous solution (500 mL) and water (500 mL), then dried with anhydrous sodium sulfate, and then concentrated under reduced pressure, thereby obtaining a compound (T-1) in the form of a pale yellow oily substance (46 g, 207 mmol).

Second Process: Synthesis of Compound (T-2)

1,3-dithiane (61 g, 507 mmol) was dissolved in tetrahydrofuran (420 mL), and the resultant was cooled at −30° C. under a nitrogen atmosphere. N-butyllithium (1.6 mol/L hexane solution, 350 mL, 560 mmol) was dripped in while its temperature was maintained at −30° C., and then the resultant was stirred at −30° C. for 1 hour. While the temperature of this mixture was maintained at −30° C., chlorotrimethylsilane (66 g, 608 mmol) was dripped in. The resultant was stirred at −30° C. for 1 hour and then heated to 25° C. 10% hydrochloric acid (500 mL) was added to the reaction mixture and extracted with hexane (500 mL, three times). The combined organic layers were washed with water (200 mL, twice), then dried with anhydrous sodium sulfate, and then concentrated under reduced pressure, thereby obtaining a compound (T-2) in the form of a pale yellow oily substance (90 g, 468 mmol).

Third Process: Synthesis of Compound (T-3)

The compound (T-2) (90 g, 468 mmol) obtained by the above operation was dissolved in tetrahydrofuran (500 mL), and the resultant was cooled at −10° C. under a nitrogen atmosphere. N-butyllithium (1.6 mol/L hexane solution, 327 mL, 523 mmol) was dripped in while its temperature was maintained at −10° C., and the resultant was further stirred at −10° C. for 1 hour. While the temperature of this mixture was maintained at −10° C., a tetrahydrofuran (100 mL) solution of 4-pentylcyclohexa-1-one (73 g, 434 mmol) was dripped in. Then, the resultant was stirred at 25° C. for 1 hour. 10% hydrochloric acid (400 mL) was added to the reaction mixture and extracted with hexane (500 mL, three times). The combined organic layers were washed with water (200 mL, twice), then dried with anhydrous sodium sulfate, and then concentrated under reduced pressure. The resultant was purified by recrystallization (ethanol), and a compound (T-3) was obtained in the Ruin of a pale yellow solid (106 g, 392 mmol).

Fourth Process: Synthesis of Compound (1-2-1)

The compound (T-3) (35 g, 129 mmol) obtained by the above operation was dissolved in methylene chloride (150 mL), and the resultant was cooled at 0° C. under a nitrogen atmosphere. While the temperature of this solution was maintained at 0° C., trifluoromethanesulfonic acid (20 g, 133 mmol) was dripped in, and the resultant was further stirred at 25° C. for 1 hour. This mixture was cooled at −70° C. While the temperature of the mixture was maintained at −70° C., a methylene chloride (60 mL) solution of the compound (T-1) (32 g, 144 mmol) and triethylamine (19 g, 188 mmol) was dripped in. The resultant was stirred at −70° C. for 2 hours. Then, while the temperature of the resultant was maintained at −70° C., triethylamine trihydrofluoride (69 g, 428 mmol) was dripped in, and the resultant was further stirred for 20 minutes. While the temperature of the resultant was maintained at −70° C., bromine (69 g, 432 mmol) was dripped in, and the resultant was stirred at −70° C. for 40 minutes and further at 25° C. for 1 hour. A saturated sodium sulfite aqueous solution (300 mL) was added to the reaction mixture and subjected to separation. Then, the organic layer was washed with a sodium hydrogen carbonate aqueous solution (300 mL) and water (300 mL). This solution was dried with anhydrous sodium sulfate, and concentrated under reduced pressure. The resultant was purified by column chromatography (hexane) and recrystallization (ethanol/ethyl acetate, twice), and a compound (1-2-1) was obtained in the form of colorless needle crystals (8 g, 19 mmol).

$^1$H-NMR (δppm; CDCl$_3$): 6.94 (s, 2H), 5.05 (s, 1H), 2.06-1.94 (m, 3H), 1.86 (d, J=12.1 Hz, 2H), 1.42 (s, 18H), 1.40-1.18 (m, 11H), 0.96-0.86 (m, 5H).

$^{19}$F-NMR (δppm; CDCl$_3$): 78.43 (d, J=8.0 Hz, 2F).

Synthesis Example 2

A compound (1-3-1) was synthesized in the same manner by the method shown in Synthesis Example 1. When 96 g of 4'-propyl-[1,1'-bi(cyclohexa)]-4-non) was used as a starting raw material, the compound was obtained in the form of colorless needle crystals (14 g).

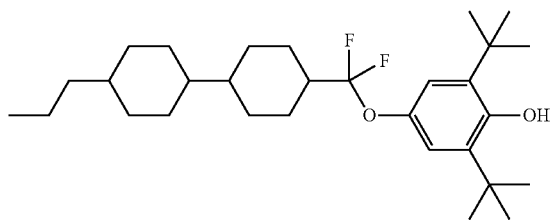 [SMILES: CCCC1CCC(C2CCC(C(F)(F)Oc3cc(C(C)(C)C)c(O)c(C(C)(C)C)c3)CC2)CC1]

(1-3-1)

$^1$H-NMR (δppm; CDCl$_3$): 6.94 (s, 2H), 5.05 (s, 1H), 2.05 (d, J=11.0 Hz, 2H), 2.01-1.94 (m, 1H), 1.84 (d, J=11.0 Hz, 2H), 1.74 (t, J=15.8 Hz, 4H), 1.42 (s, 18H), 1.37 (d, J=12.0 Hz, 2H), 1.33-1.28 (m, 2H), 1.14 (t, J=6.0 Hz, 3H), 1.06-0.97 (m, 6H), 0.89-0.84 (m, 5H).

$^{19}$F-NMR (δppm; CDCl$_3$): 78.47 (d, J=8.5 Hz, 2F).

Synthesis Example 3

A compound (1-2-15) was synthesized according to the following synthesis scheme.

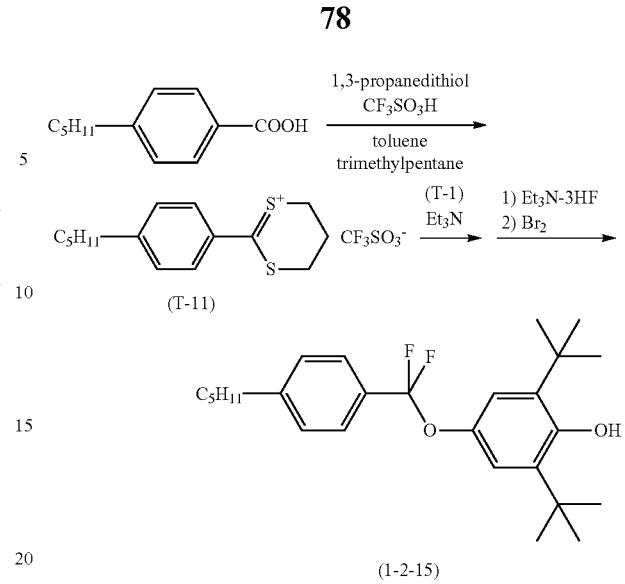

First Process: Synthesis of Compound (T-11)

Under a nitrogen atmosphere 4-pentylbenzoic acid (8.06 g, 41.9 mmol), toluene (40 ml) and 2,2,4-trimethylpentane (40 ml) were placed in a reactor and heated at 60° C. Propanedithiol (5.0 g, 45.8 mmol) was added thereto, and the resultant was stirred for 1 hour. Then, trifluoromethanesulfonic acid (13.9 g, 92.3 mmol) was gradually added, and the resultant was stirred for 1 hour. Subsequently, the resultant was heated under reflux for 2 hours while the distilled water was removed. The reaction mixture was cooled to room temperature, and then concentrated under reduced pressure. The residue was purified by recrystallization from t-butyl methyl ether so as to obtain a compound (T-11) (7.2 g, 17.4 mmol; 41%).

Second Process: Synthesis of Compound (1-2-15)

Under a nitrogen atmosphere, the compound (T-1) (5.0 g, 22.7 mmol), triethylamine (2.3 g, 23.0 mmol) and dichloromethane (30 ml) were placed in a reactor, and cooled at −70° C. A dichloromethane (80 ml) solution of the compound (T-11) (7.2 g, 17.4 mmol) was gradually added thereto, and the resultant was stirred for 1 hour. Next, a hydrogen fluoride-triethylamine complex (8.8 g, 54.5 mmol) was gradually added, and the resultant was stirred for 30 minutes. Subsequently, bromine (14.2 g, 88.8 mmol) was gradually added, and the resultant was further stirred for 1 hour. The reaction mixture was poured into ice water, and the resultant was neutralized using sodium hydrogen carbonate. Then, the water layer was extracted with dichloromethane. The combined organic layers were washed with water and dried with anhydrous magnesium sulfate. This solution was concentrated under reduced pressure, and the residue was purified by silica gel chromatography (heptane), so as to obtain a compound (1-2-15) (0.7 g, 1.7 mmol; 10%).

$^1$H-NMR (δppm; CDCl$_3$): 7.62 (d, J=8.0 Hz, 2H), 7.26 (d, J=8.0 Hz, 2H), 7.26 (s, 2H), 5.09 (s, 1H), 2.65 (t, J=7.5 Hz, 2H), 1.66-1.59 (m, 2H), 1.42 (s, 18H), 1.36-1.29 (m, 4H), 0.90 (t, J=7.0 Hz, 3H).

$^{19}$F-NMR (δppm; CFCl$_3$): −65.57 (s, 2F).

Synthesis Example 4

A compound (1-3-34) was synthesized in the same manner by the method shown in Synthesis Example 3. When 2-fluoro-4-(4-propylcyclohexyl)benzoic acid was used as a starting raw material, the compound was obtained in the form of colorless needle crystals (1.8 g).
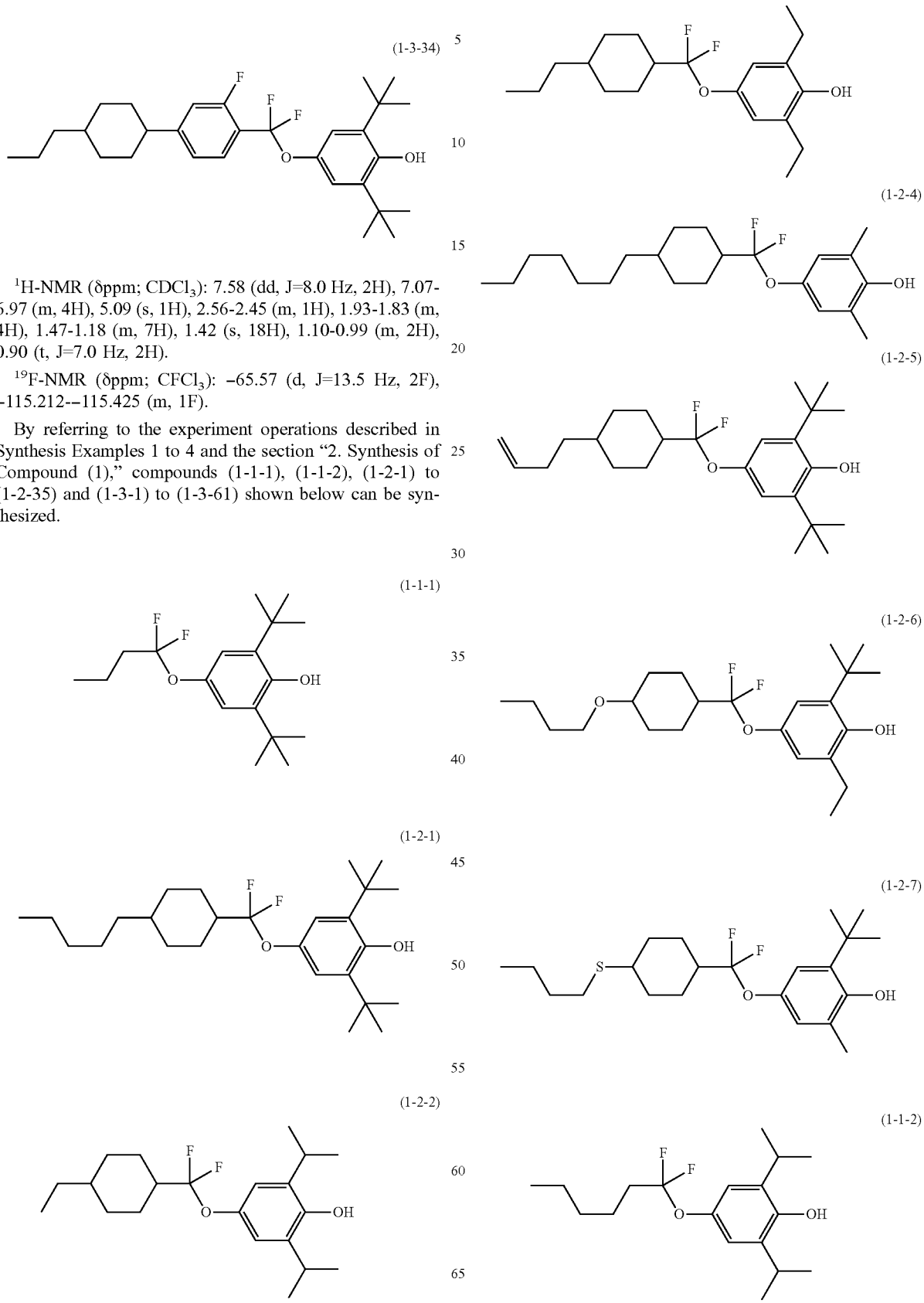
¹H-NMR (δppm; CDCl₃): 7.58 (dd, J=8.0 Hz, 2H), 7.07-6.97 (m, 4H), 5.09 (s, 1H), 2.56-2.45 (m, 1H), 1.93-1.83 (m, 4H), 1.47-1.18 (m, 7H), 1.42 (s, 18H), 1.10-0.99 (m, 2H), 0.90 (t, J=7.0 Hz, 2H).
¹⁹F-NMR (δppm; CFCl₃): −65.57 (d, J=13.5 Hz, 2F), −115.212−−115.425 (m, 1F).
By referring to the experiment operations described in Synthesis Examples 1 to 4 and the section "2. Synthesis of Compound (1)," compounds (1-1-1), (1-1-2), (1-2-1) to (1-2-35) and (1-3-1) to (1-3-61) shown below can be synthesized.

(1-2-8)
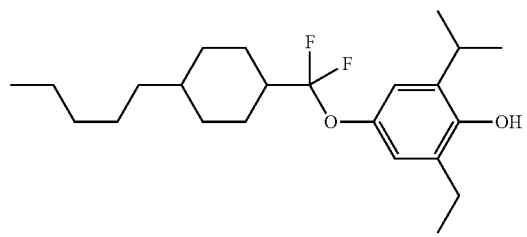
(1-2-9)
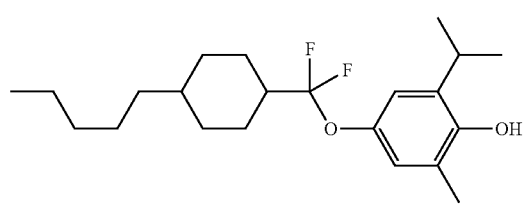
(1-2-10)
(1-2-11)
(1-2-12)
(1-2-13)
(1-2-14)
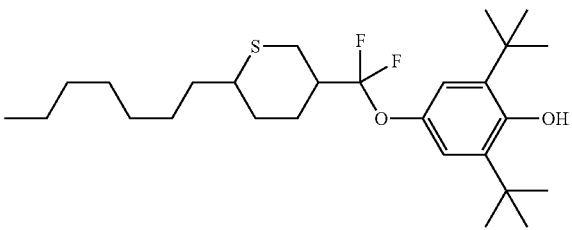
(1-2-15)
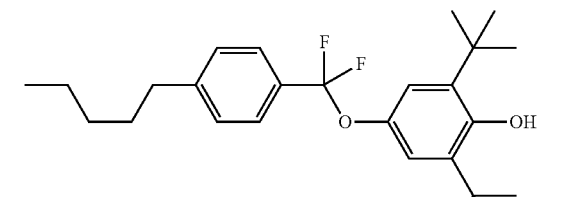
(1-2-16)
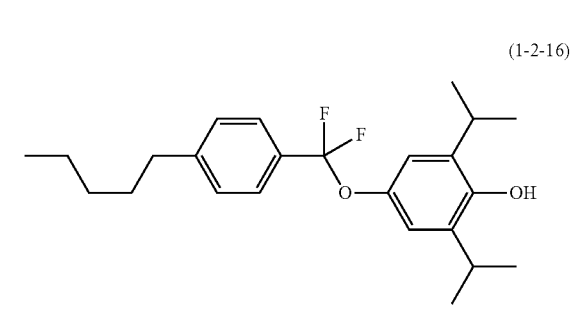
(1-2-17)
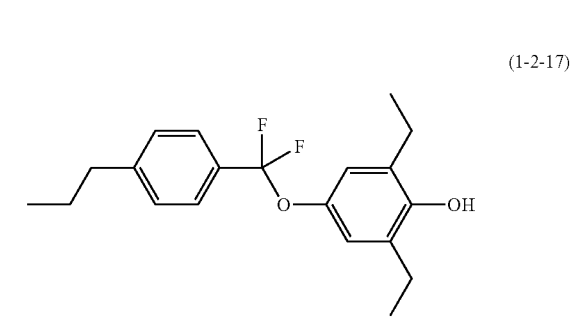
(1-2-18)
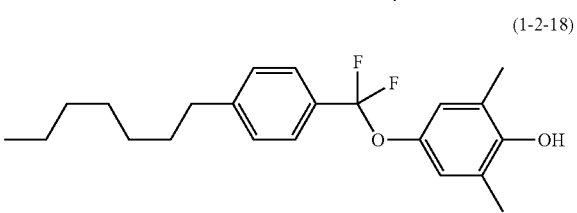
(1-2-19)
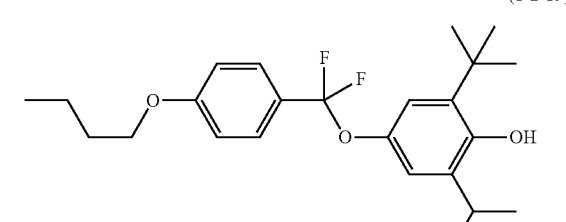

(1-2-20)
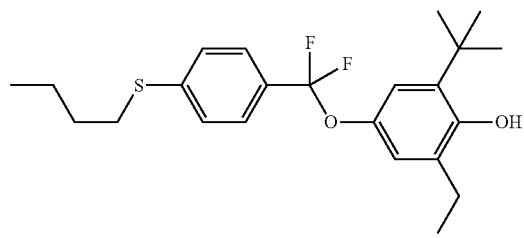
(1-2-21)
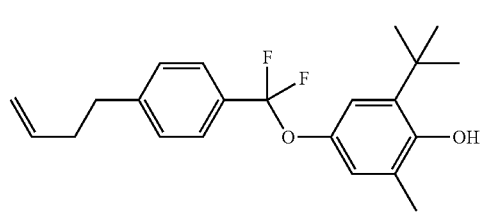
(1-2-22)
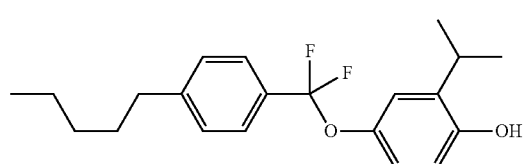
(1-2-23)
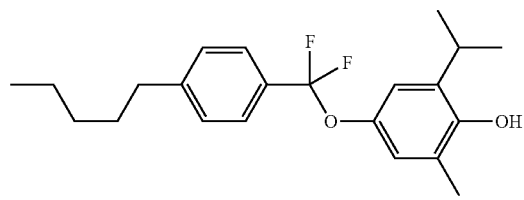
(1-2-24)
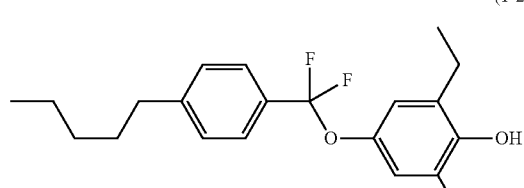
(1-2-25)
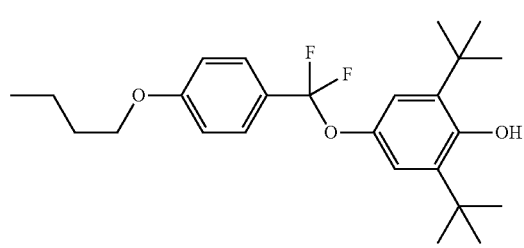
(1-2-26)
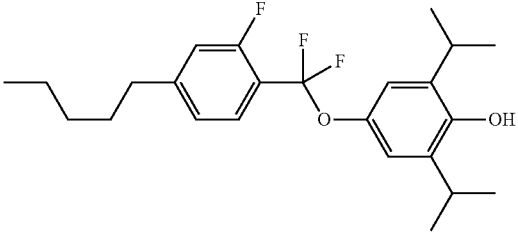
(1-2-27)
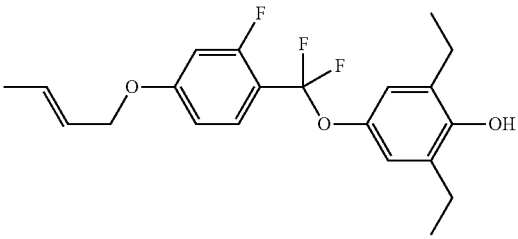
(1-2-28)
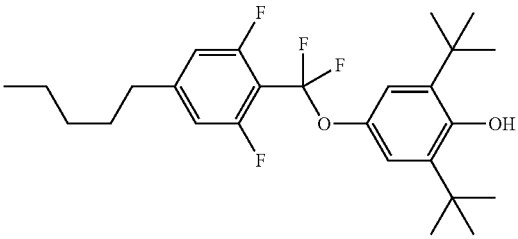
(1-2-29)
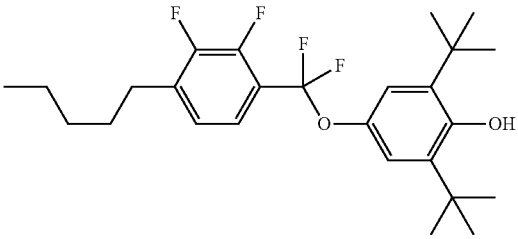
(1-2-30)
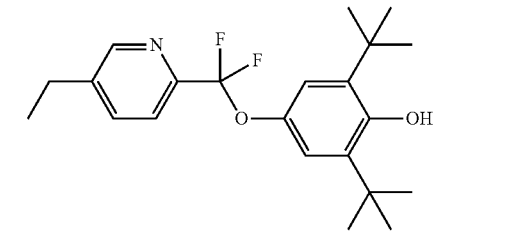
(1-2-31)
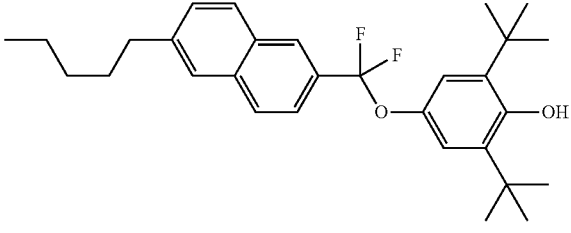

(1-2-32)
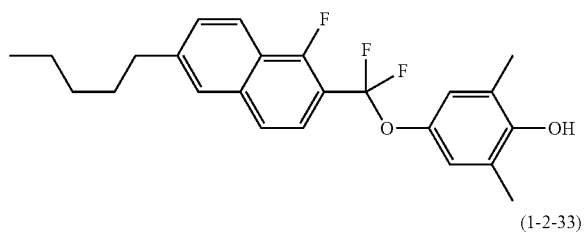
(1-2-33)
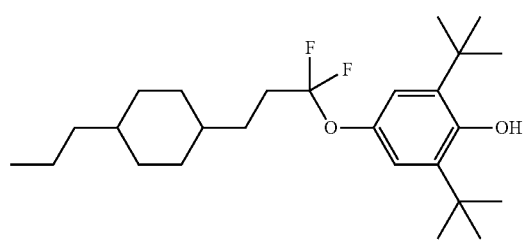
(1-2-34)
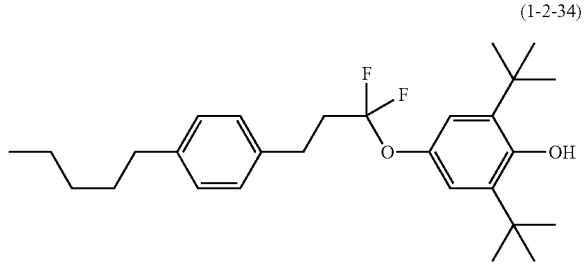
(1-2-35)
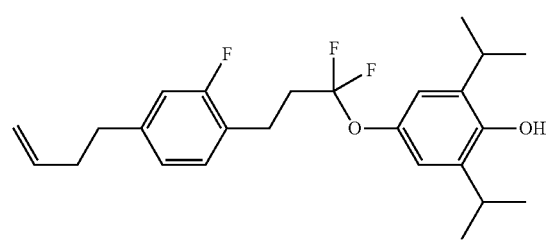
(1-3-1)
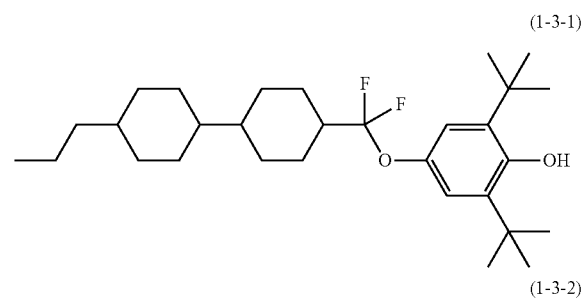
(1-3-2)
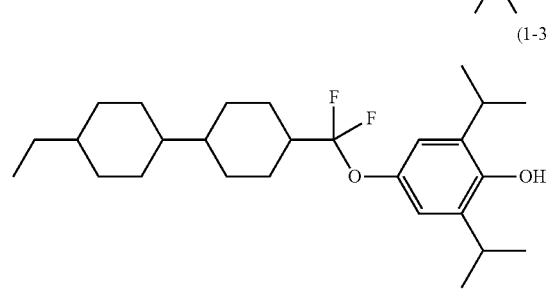
(1-3-3)
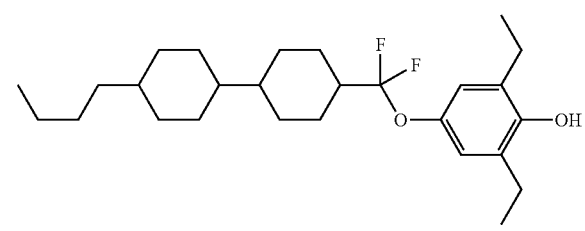
(1-3-4)
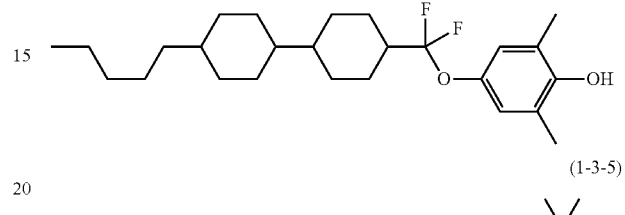
(1-3-5)
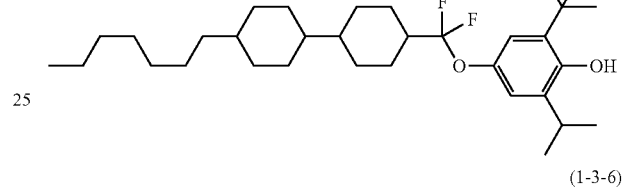
(1-3-6)
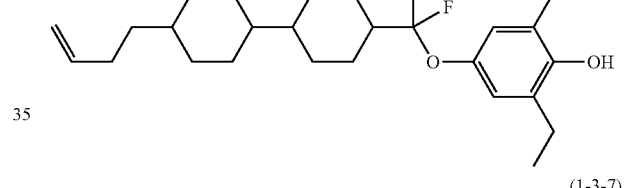
(1-3-7)
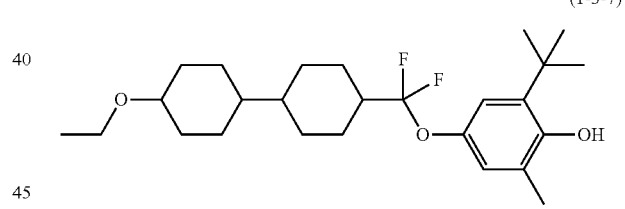
(1-3-8)
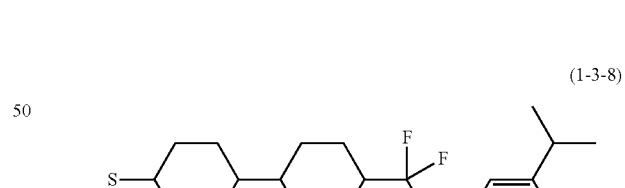
(1-3-9)
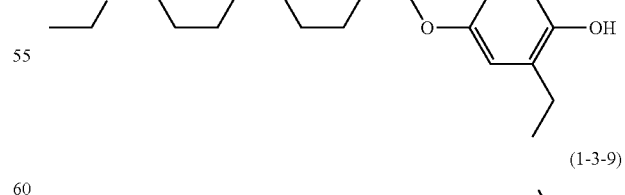

(1-3-10)
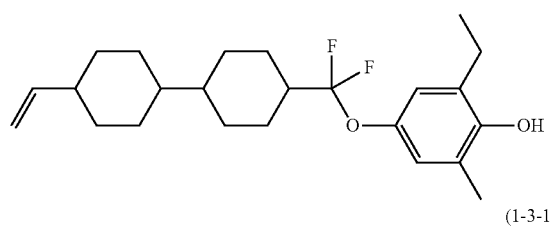
(1-3-11)
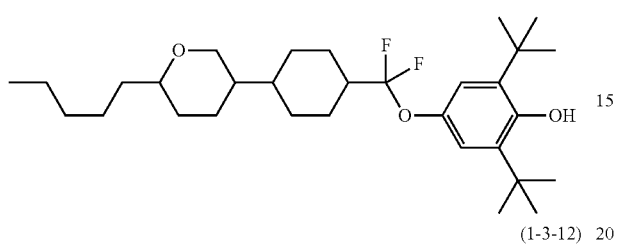
(1-3-12)
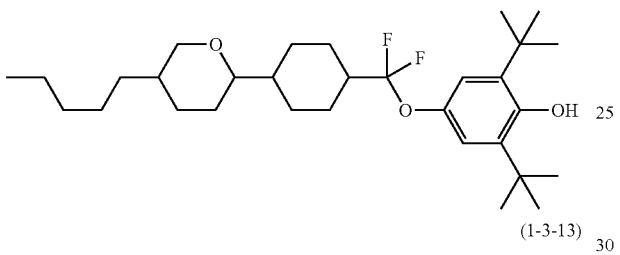
(1-3-13)
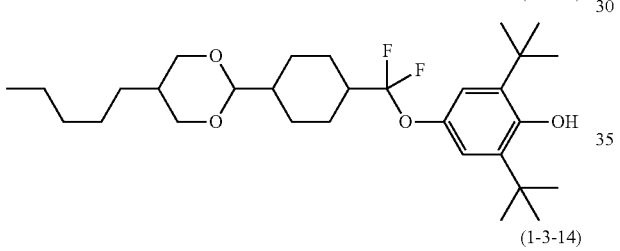
(1-3-14)
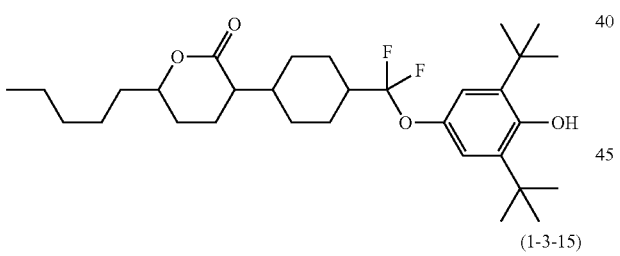
(1-3-15)
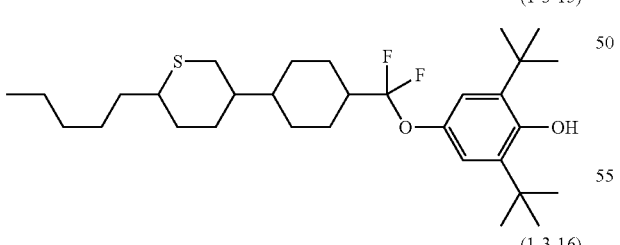
(1-3-16)
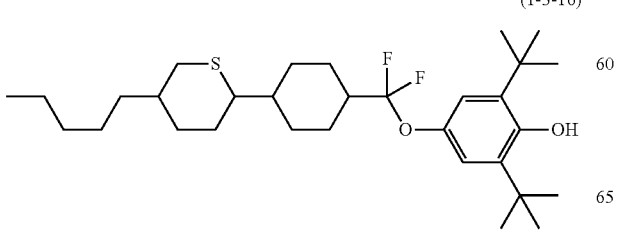
(1-3-17)
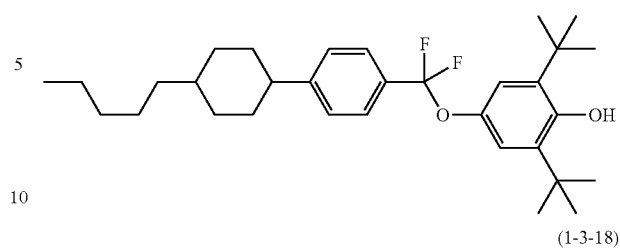
(1-3-18)
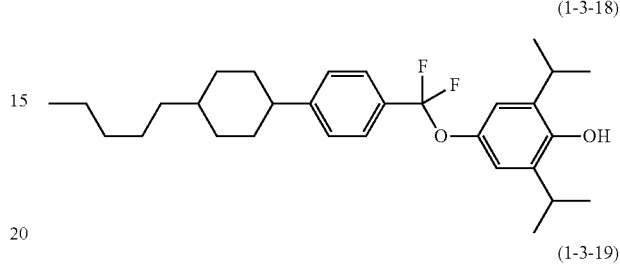
(1-3-19)
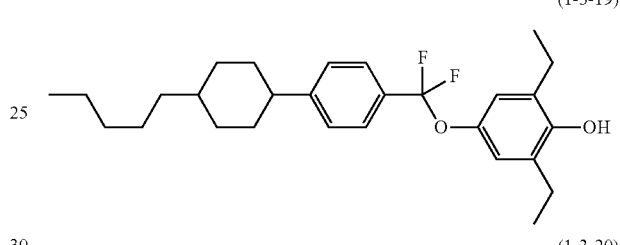
(1-3-20)
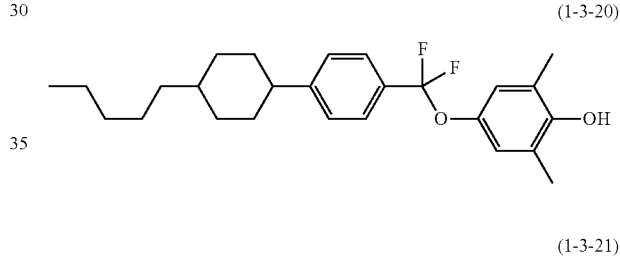
(1-3-21)
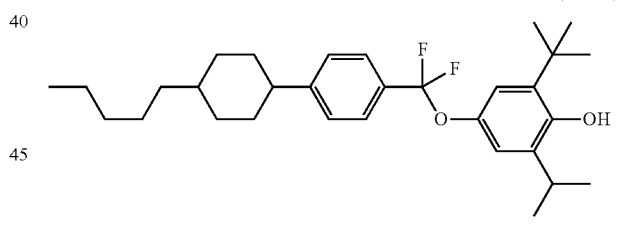
(1-3-22)
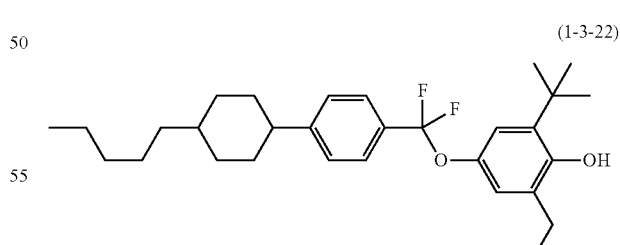
(1-3-23)
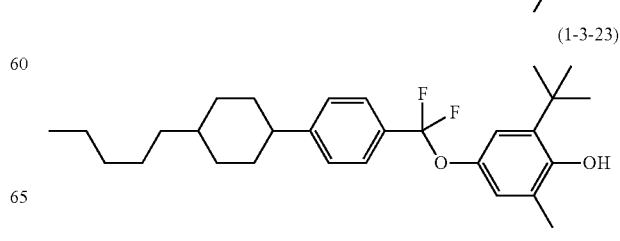

(1-3-24)
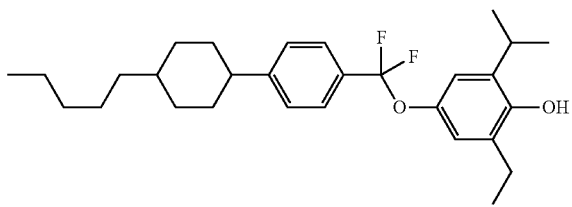
(1-3-25)
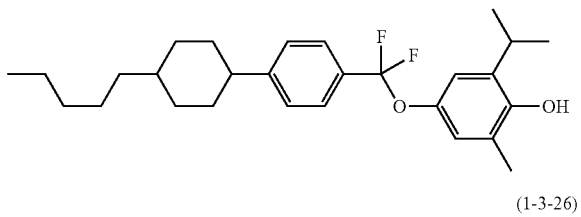
(1-3-26)
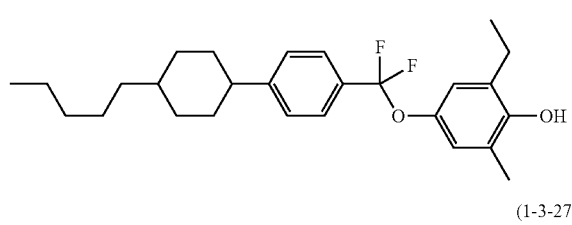
(1-3-27)
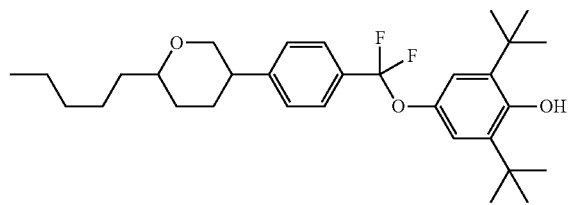
(1-3-28)
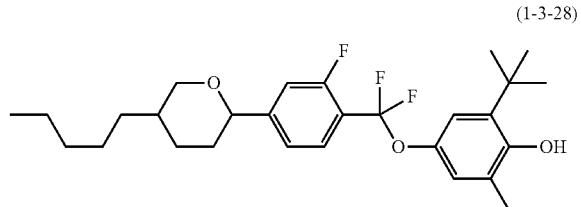
(1-3-29)
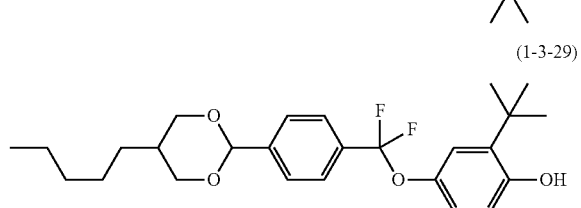
(1-3-30)
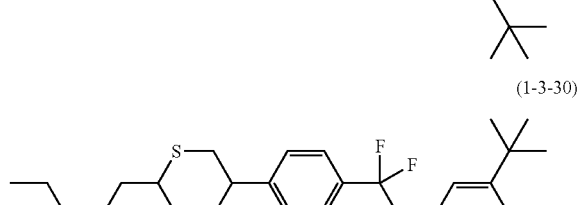
(1-3-31)
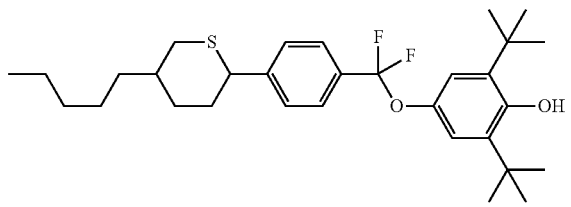
(1-3-32)
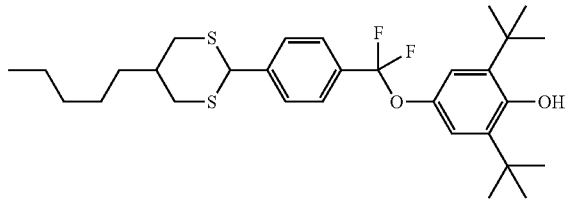
(1-3-33)
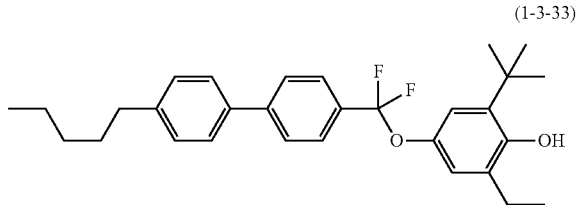
(1-3-34)
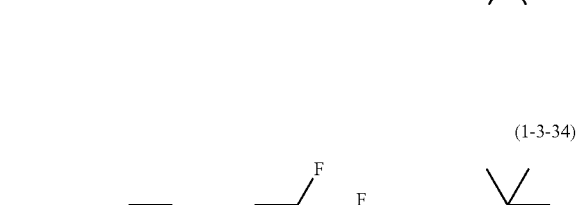
(1-3-35)
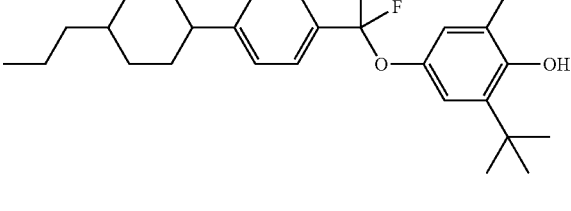
(1-3-36)
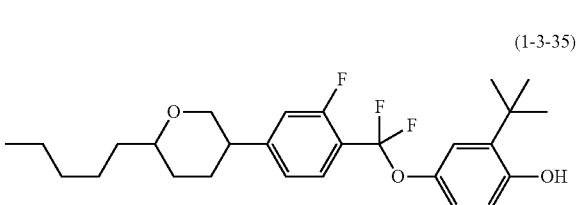

(1-3-37)
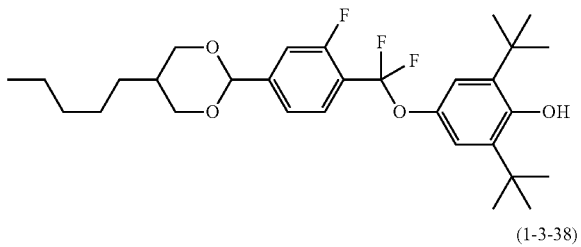
(1-3-38)
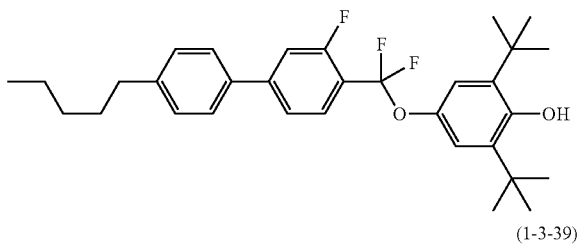
(1-3-39)
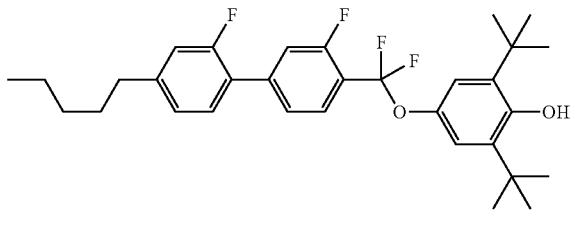
(1-3-40)
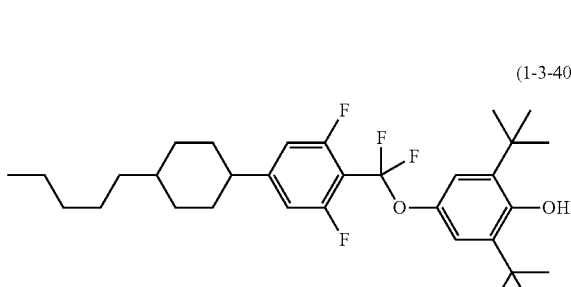
(1-3-41)
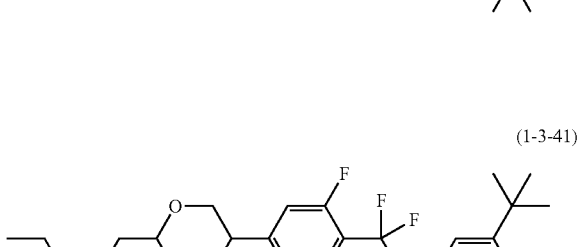
(1-3-42)
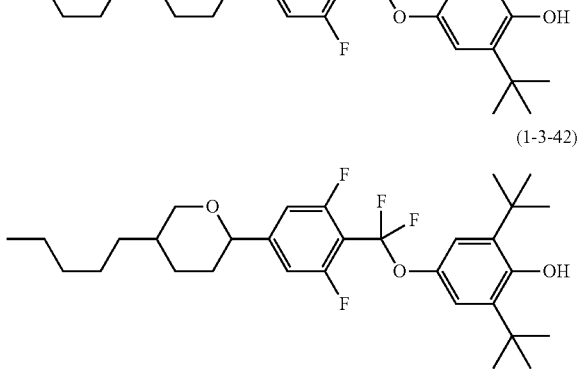
(1-3-43)
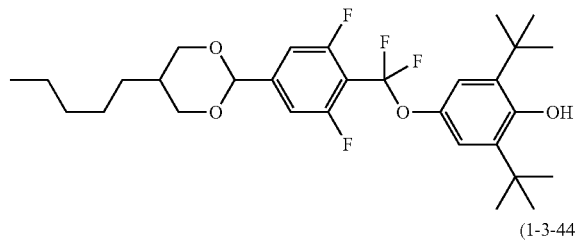
(1-3-44)
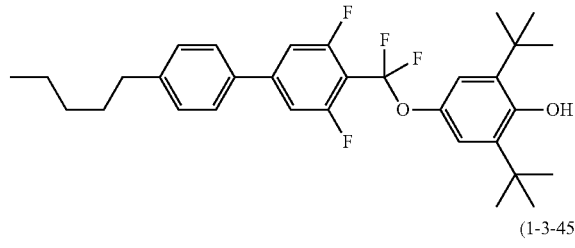
(1-3-45)
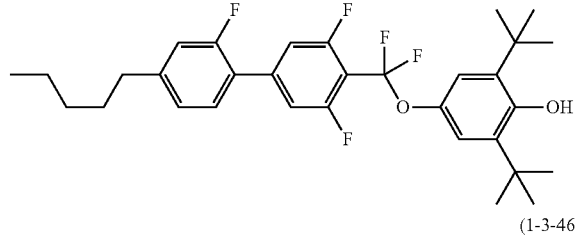
(1-3-46)
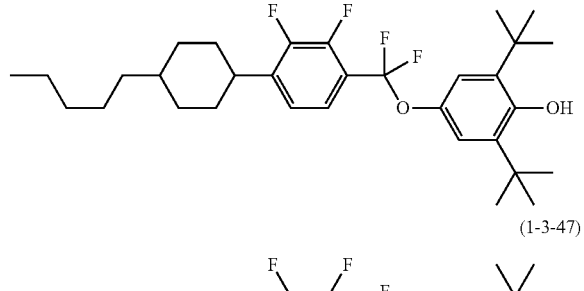
(1-3-47)
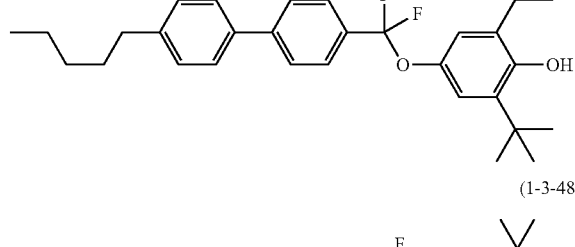
(1-3-48)
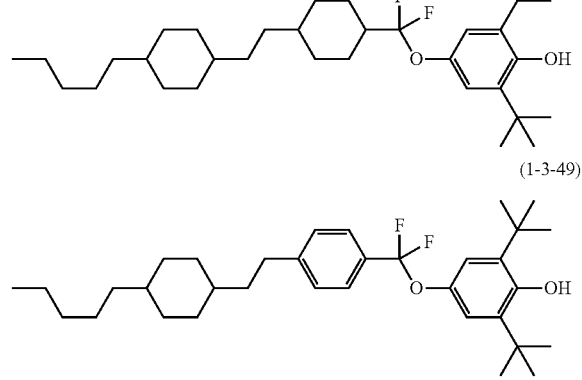
(1-3-49)

(1-3-50)
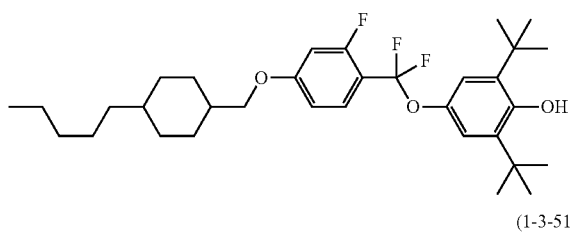

(1-3-51)
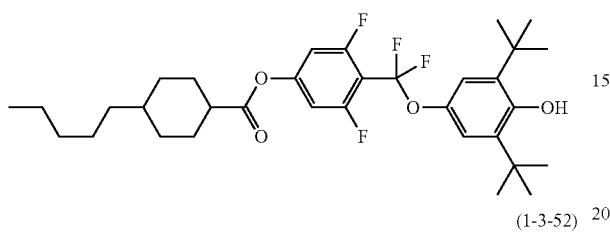

(1-3-52)
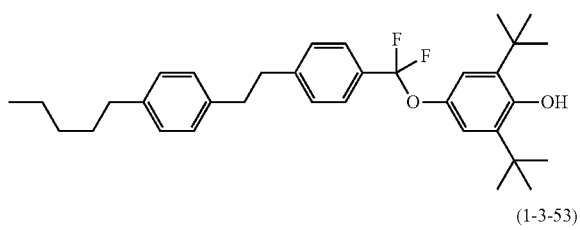

(1-3-53)
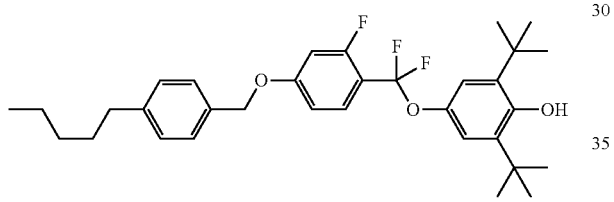

(1-3-54)
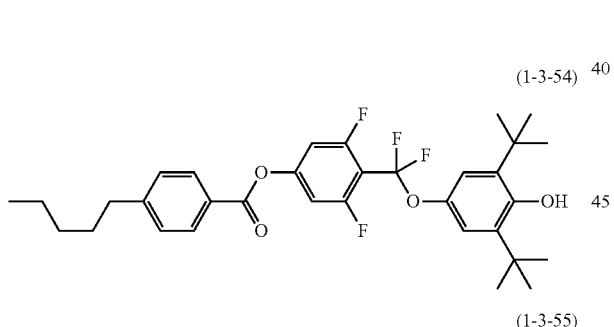

(1-3-55)
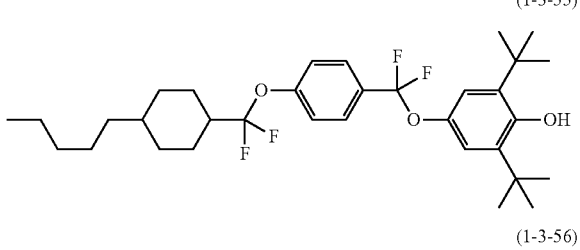

(1-3-56)

(1-3-57)
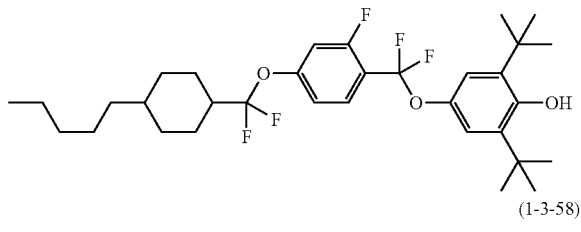

(1-3-58)
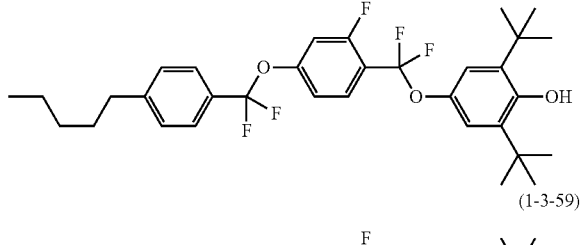

(1-3-59)
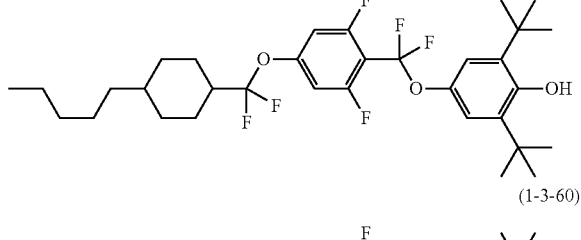

(1-3-60)
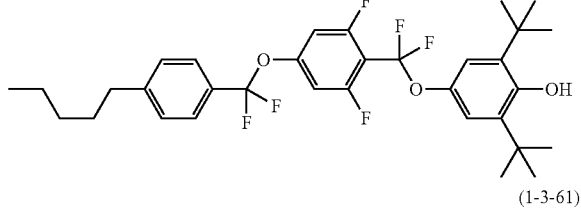

(1-3-61)
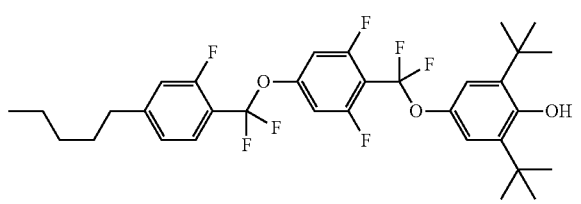

[Comparative Experiment]

The compound (1) is useful as an antioxidant. In order to examine this effect, the compound (1) was added to a liquid crystal composition A. A TN device including the composition was produced, and the voltage holding ratio (VHR-2 and VHR-3) was measured. The measurement method was as described in the above items (9) and (10). The components of the liquid crystal composition A and their ratios are as follows. A method of describing compounds using symbols is shown in Table 2.

(Liquid Crystal Composition A)

| | | |
|---|---|---|
| 3-HH-V | (2-1) | 18% |
| 3-HH-4 | (2-1) | 10% |
| 3-HB-O2 | (2-5) | 3% |
| 4-BB(F)B(F,F)XB(F,F)-F | (7-47) | 10% |
| 5-BB(F)B(F,F)XB(F,F)-F | (7-47) | 6% |
| 3-HHB-1 | (3-1) | 6% |
| 3-HHB-3 | (3-1) | 5% |
| 3-HHB-O1 | (3-1) | 5% |

-continued

| | | |
|---|---|---|
| 3-BB(F,F)XB(F,F)-F | (6-97) | 14% |
| 3-HHB(F,F)-F | (6-3) | 9% |
| 3-BB(F)B(F,F)-F | (6-69) | 7% |
| 3-GHB(F,F)-F | (6-109) | 4% |
| 3-HHXB(F,F)-F | (6-100) | 3% |

The compounds (1-2-1) and (1-3-1) were selected as the compound of the invention. The structural formulae of the compounds were described in Table 1. A well-known compound (BH7) was selected as an antioxidant for comparison, because this compound is used in Example 8 in WO 2014/162587. The compound (BH3L) described in the examples in JP H09-124529 was also selected. Each compound was added to the liquid crystal composition A in a ratio of 0.10%. This composition was placed into a TN device, and the voltage holding ratio was measured. The results were summarized in Table 1. The voltage holding ratio measured at 80° C. was expressed by VHR-2. Under these conditions, the compound of the invention and the comparative compounds all had substantially the same voltage holding ratio of about 99%. Next, the measurement was carried out after an ultraviolet treatment. After ultraviolet light had been irradiated for 20 minutes, as shown in the column of the voltage holding ratio (VHR-3), a large difference was observed. In the case of the comparative compounds, the voltage holding ratio was decreased sharply as 4.8% and 6.3%. However, in the case of the compounds (1-2-1) and (1-3-1), the voltage holding ratio stayed at 46.2% and 41.4%, respectively. Accordingly, since the compounds (1-2-1) and (1-3-1) had a larger VHR-3 as compared to the comparative compounds, it can be concluded that the compounds (1-2-1) and (1-3-1) have high stability to ultraviolet light.

TABLE 1

Comparison of Voltage Holding Ratio

| No. | Compound | Structural formula | Amount added (%) | VHR-2 (%) | VHR-3 (%) |
|---|---|---|---|---|---|
| 1 | Compound (1-2-1) | | 0.1 | 99.0 | 46.2 |
| 2 | Compound (1-3-1) | | 0.1 | 99.3 | 41.4 |
| 3 | Compound (BH7) | | 0.1 | 99.0 | 4.8 |
| 4 | Compound (BH3L) | | 0.1 | 99.0 | 6.3 |

2. Examples of Liquid Crystal Composition

The compounds in the examples (including use examples) were represented by symbols based on the definitions in the following Table 2. In Table 2, the stereo configuration of 1,4-cyclohexylene is trans. In the examples, the number in the parentheses following the symbol corresponds to the number of the compound. The symbol (-) means other liquid crystal compounds. The content (percentage) of a liquid crystal compound is a weight percentage (wt %) based on the weight of a liquid crystal composition. Finally, characteristic values of the liquid crystal composition were summarized. The characteristics were measured according to the methods described previously, and the measured values themselves were recorded without change (without extrapolation).

TABLE 2

| Method of Description of Compound Using Symbols R—(A$_1$)—Z$_1$— ... —Z$_n$—(A$_n$)—R' | |
|---|---|
| 1) Left terminal group R— | Symbol |
| C$_n$H$_{2n+1}$— | n- |
| C$_n$H$_{2n+1}$O— | nO— |
| C$_m$H$_{2m+1}$OC$_n$H$_{2n}$— | mOn- |
| CH$_2$=CH— | V— |
| C$_n$H$_{2n+1}$—CH=CH— | nV— |
| CH$_2$=CH—C$_n$H$_{2n}$— | Vn- |
| C$_m$H$_{2m+1}$—CH=CH—C$_n$H$_{2n}$— | mVn- |
| CF$_2$=CH— | VFF— |
| CF$_2$=CH—C$_n$H$_{2n}$— | VFFn- |
| 2) Right terminal group —R' | Symbol |
| —C$_n$H$_{2n+1}$ | -n |
| —OC$_n$H$_{2n+1}$ | —On |
| —COOCH$_3$ | —EMe |
| —CH=CH$_2$ | —V |
| —CH=CH—C$_n$H$_{2n+1}$ | —Vn |
| —C$_n$H$_{2n}$—CH=CH$_2$ | -nV |
| —C$_m$H$_{2m}$—CH=CH—C$_n$H$_{2n+1}$ | -mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —OCH=CH—CF$_3$ | —OVCF3 |
| —C≡N | —C |
| 3) Linking group —Z$_n$— | Symbol |
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| 4) Ring structure —(A$_n$)— | Symbol |
| (cyclohexane) | H |
| (benzene) | B |
| (fluorobenzene) | B(F) |
| (2-fluorobenzene) | B(2F) |
| (difluorobenzene) | B(F,F) |
| (2,5-difluorobenzene) | B(2F,5F) |
| (2,3-difluorobenzene) | B(2F,3F) |
| (pyrimidine) | Py |
| (dioxane) | G |
| (tetrahydropyran) | Dh |
| (fluoro-chromane) | Cro |
| (2-fluoro-3-chlorobenzene) | B(2F,3CL) |
| 5) Examples of description | |
| Example 1: 3-HH-V | |

TABLE 2-continued

Method of Description of Compound Using Symbols
R—(A₁)—Z₁— . . . —Zₙ—(Aₙ)—R'

Example 2: 3-BB(F,F)XB(F,F)-F

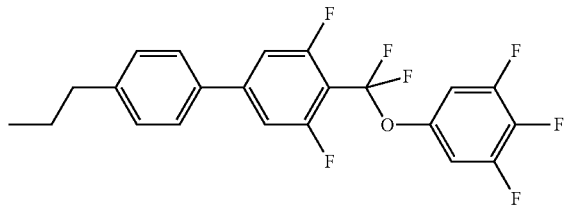

Example 3: 3-HH-4

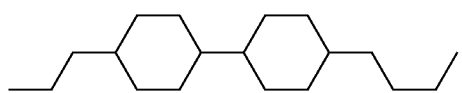

Example 4: 3-HBB(2F,3F)-O2

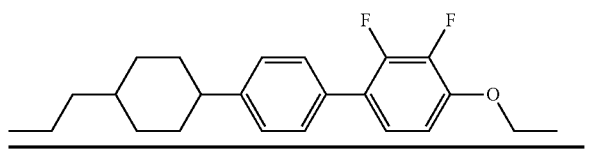

Use Example 1

| | | |
|---|---|---|
| 3-HB-O2 | (2-5) | 11% |
| 5-HB-CL | (5-2) | 15% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 9% |
| 5-PyBB-F | (6-80) | 9% |
| 5-HBB(F)B-2 | (4-5) | 10% |
| 5-HBB(F)B-3 | (4-5) | 9% |

The following compound (1-2-1) was added to the above composition in a ratio of 0.08%.

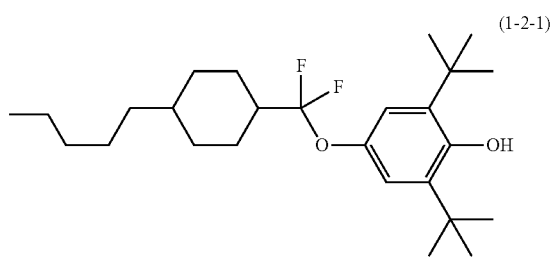 [SMILES: CCCCCC1CCC(C(F)(F)Oc2cc(C(C)(C)C)c(O)c(C(C)(C)C)c2)CC1]

NI=94.4° C.; η=37.9 mPa·s; Δn=0.185; and Δ∈=7.8.

Use Example 2

| | | |
|---|---|---|
| 2-HB-C | (8-1) | 6% |
| 3-HB-C | (8-1) | 10% |
| 3-HB-O2 | (2-5) | 15% |
| 2-BTB-1 | (2-10) | 4% |

-continued

| | | |
|---|---|---|
| 3-HHB-F | (6-1) | 5% |
| 3-HHB-1 | (3-1) | 7% |
| 3-HHB-O1 | (3-1) | 5% |
| 3-HHB-3 | (3-1) | 14% |
| 3-HHEB-F | (6-10) | 4% |
| 5-HHEB-F | (6-10) | 4% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

The following compound (1-3-1) was added to the above composition in a ratio of 0.05%.

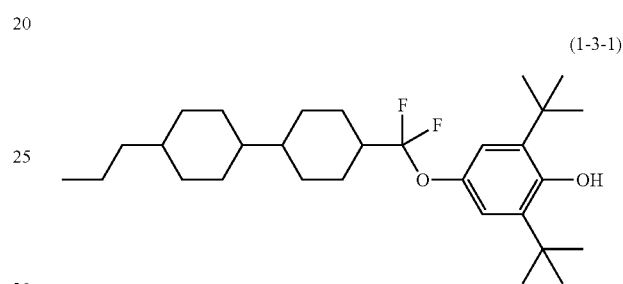

NI=99.6° C.; η=17.5 mPa·s; Δn=0.101; and Δ∈=4.5.

Use Example 3

| | | |
|---|---|---|
| 7-HB(F,F)-F | (5-4) | 5% |
| 3-HB-O2 | (2-5) | 5% |
| 2-HHB(F)-F | (6-2) | 10% |
| 3-HHB(F)-F | (6-2) | 9% |
| 5-HHB(F)-F | (6-2) | 9% |
| 2-HBB(F)-F | (6-23) | 9% |
| 3-HBB(F)-F | (6-23) | 9% |
| 5-HBB(F)-F | (6-23) | 16% |
| 2-HBB-F | (6-22) | 4% |
| 3-HBB-F | (6-22) | 5% |
| 5-HBB-F | (6-22) | 4% |
| 3-HBB(F,F)-F | (6-24) | 5% |
| 5-HBB(F,F)-F | (6-24) | 10% |

The following compound (1-2-16) was added to the above composition in a ratio of 0.05%.

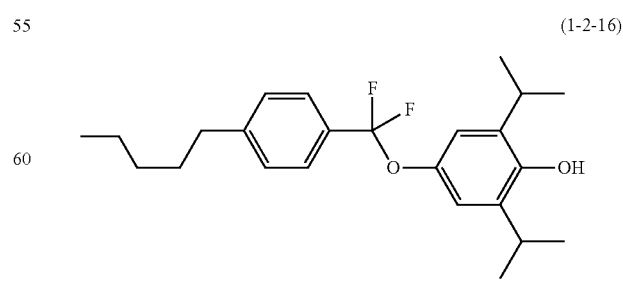

NI=83.6° C.; η=25.3 mPa·s; Δn=0.115; and Δ∈=5.6.

Use Example 4

| | | |
|---|---|---|
| 5-HB-CL | (5-2) | 13% |
| 3-HH-4 | (2-1) | 15% |
| 3-HH-5 | (2-1) | 4% |
| 3-HHB-F | (6-1) | 4% |
| 3-HHB-CL | (6-1) | 3% |
| 4-HHB-CL | (6-1) | 4% |
| 3-HHB(F)-F | (6-2) | 10% |
| 4-HHB(F)-F | (6-2) | 9% |
| 5-HHB(F)-F | (6-2) | 8% |
| 7-HHB(F)-F | (6-2) | 9% |
| 5-HBB(F)-F | (6-23) | 4% |
| 1O1-HBBH-5 | (4-1) | 3% |
| 3-HHBB(F,F)-F | (7-6) | 3% |
| 4-HHBB(F,F)-F | (7-6) | 2% |
| 5-HHBB(F,F)-F | (7-6) | 3% |
| 3-HH2BB(F,F)-F | (7-15) | 3% |
| 4-HH2BB(F,F)-F | (7-15) | 3% |

The following compound (1-2-1) was added to the above composition in a ratio of 0.1%.

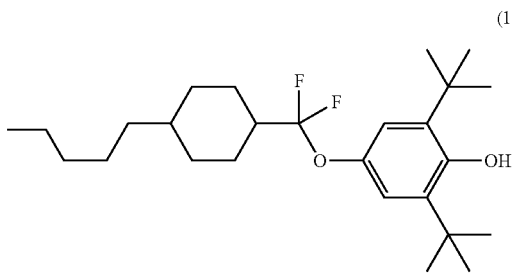

(1-2-1)

NI=117.0° C.; η=19.2 mPa·s; Δn=0.090; and Δ∈=3.6.

Use Example 5

| | | |
|---|---|---|
| 3-HHB(F,F)-F | (6-3) | 10% |
| 3-H2HB(F,F)-F | (6-15) | 8% |
| 4-H2HB(F,F)-F | (6-15) | 8% |
| 5-H2HB(F,F)-F | (6-15) | 10% |
| 3-HBB(F,F)-F | (6-24) | 19% |
| 5-HBB(F,F)-F | (6-24) | 20% |
| 3-H2BB(F,F)-F | (6-27) | 8% |
| 5-HHBB(F,F)-F | (7-6) | 4% |
| 5-HHEBB-F | (7-17) | 2% |
| 3-HH2BB(F,F)-F | (7-15) | 3% |
| 1O1-HBBH-4 | (4-1) | 4% |
| 1O1-HBBH-5 | (4-1) | 4% |

The following compound (1-3-1) was added to the above composition in a ratio of 0.1%.

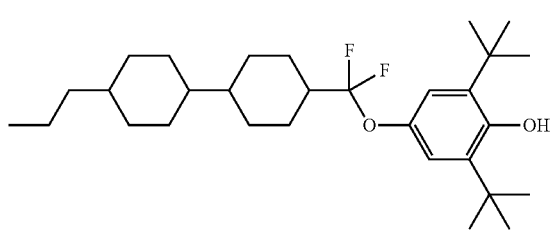

(1-3-1)

NI=100.3° C.; η=35.3 mPa·s; Δn=0.115; and Δ∈=8.9.

Use Example 6

| | | |
|---|---|---|
| 5-HB-F | (5-2) | 12% |
| 6-HB-F | (5-2) | 9% |
| 7-HB-F | (5-2) | 7% |
| 2-HHB-OCF3 | (6-1) | 7% |
| 3-HHB-OCF3 | (6-1) | 8% |
| 4-HHB-OCF3 | (6-1) | 7% |
| 5-HHB-OCF3 | (6-1) | 3% |
| 3-HH2B-OCF3 | (6-4) | 4% |
| 5-HH2B-OCF3 | (6-4) | 4% |
| 3-HHB(F,F)-OCF2H | (6-3) | 5% |
| 3-HHB(F,F)-OCF3 | (6-3) | 5% |
| 3-HH2B(F)-F | (6-5) | 3% |
| 3-HBB(F)-F | (6-23) | 10% |
| 5-HBB(F)-F | (6-23) | 10% |
| 5-HBBH-3 | (4-1) | 3% |
| 3-HB(F)BH-3 | (4-2) | 3% |

The following compound (1-2-16) was added to the above composition in a ratio of 0.1%.

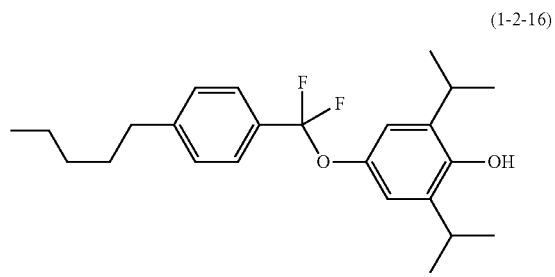 [SMILES: CCCCCc1ccc(C(F)(F)Oc2cc(C(C)C)c(O)c(C(C)C)c2)cc1]

(1-2-16)

NI=84.9° C.; η=15.2 mPa·s; Δn=0.092; and Δ∈=4.6.

Use Example 7

| | | |
|---|---|---|
| 5-HB-CL | (5-2) | 11% |
| 3-HH-4 | (2-1) | 8% |
| 3-HHB-1 | (3-1) | 6% |
| 3-HHB(F,F)-F | (6-3) | 8% |
| 3-HBB(F,F)-F | (6-24) | 19% |
| 5-HBB(F,F)-F | (6-24) | 15% |
| 3-HHEB(F,F)-F | (6-12) | 10% |
| 4-HHEB(F,F)-F | (6-12) | 4% |
| 5-HHEB(F,F)-F | (6-12) | 4% |
| 2-HBEB(F,F)-F | (6-39) | 4% |
| 3-HBEB(F,F)-F | (6-39) | 4% |
| 5-HBEB(F,F)-F | (6-39) | 3% |
| 3-HHBB(F,F)-F | (7-6) | 4% |

The following compound (1-2-1) was added to the above composition in a ratio of 0.05%.

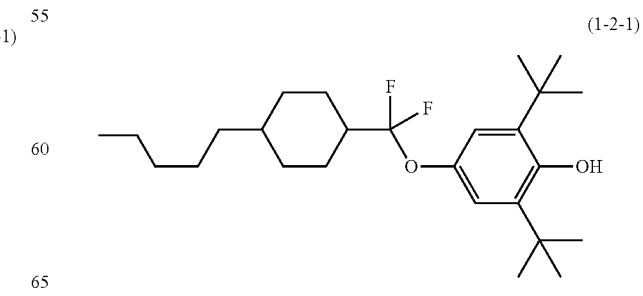

(1-2-1)

NI=79.2° C.; η=21.7 mPa·s; Δn=0.101; and Δ∈=8.6.

Use Example 8

| | | |
|---|---|---|
| 3-HB-CL | (5-2) | 5% |
| 5-HB-CL | (5-2) | 5% |
| 3-HHB-OCF3 | (6-1) | 5% |
| 3-H2HB-OCF3 | (6-13) | 5% |
| 5-H4HB-OCF | (6-19) | 15% |
| V-HHB(F)-F | (6-2) | 5% |
| 3-HHB(F)-F | (6-2) | 6% |
| 5-HHB(F)-F | (6-2) | 6% |
| 3-H4HB(F,F)-CF3 | (6-21) | 8% |
| 5-H4HB(F,F)-CF3 | (6-21) | 10% |
| 5-H2HB(F,F)-F | (6-15) | 5% |
| 5-H4HB(F,F)-F | (6-21) | 7% |
| 2-H2BB(F)-F | (6-26) | 5% |
| 3-H2BB(F)-F | (6-26) | 8% |
| 3-HBEB(F,F)-F | (6-39) | 5% |

The following compound (1-3-1) was added to the above composition in a ratio of 0.08%.

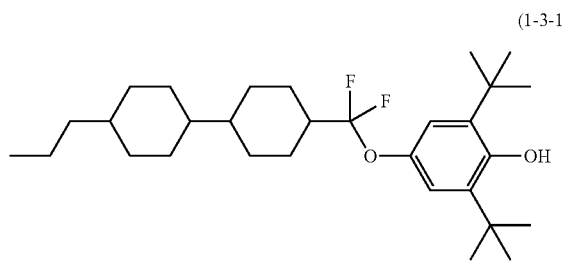

(1-3-1)

NI=70.5° C.; η=25.3 mPa·s; Δn=0.096; and Δ∈=8.3.

Use Example 9

| | | |
|---|---|---|
| 5-HB-CL | (5-2) | 20% |
| 3-HH-4 | (2-1) | 10% |
| 3-HH-5 | (2-1) | 5% |
| 3-HB-O2 | (2-5) | 15% |
| 3-HHB-1 | (3-1) | 8% |
| 3-HHB-O1 | (3-1) | 5% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 6% |
| 3-H2HB(F,F)-F | (6-15) | 5% |
| 4-H2HB(F,F)-F | (6-15) | 5% |

The following compound (1-2-16) was added to the above composition in a ratio of 0.06%.

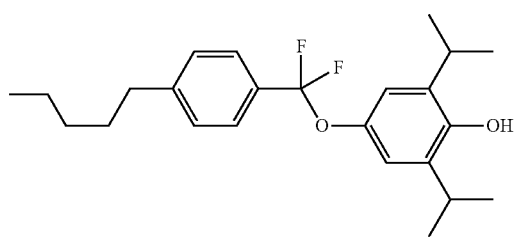

(1-2-16)

NI=73.1° C.; η=13.0 mPa·s; Δn=0.076; and Δ∈=2.8.

Use Example 10

| | | |
|---|---|---|
| 5-HB-CL | (5-2) | 5% |
| 7-HB(F)-F | (2-1) | 5% |
| 3-HH-4 | (2-1) | 11% |
| 3-HH-EMe | (2-2) | 10% |
| 3-HHEB-F | (6-10) | 9% |
| 5-HHEB-F | (6-10) | 10% |
| 3-HHEB(F,F)-F | (6-12) | 10% |
| 4-HHEB(F,F)-F | (6-12) | 6% |
| 4-HGB(F,F)-F | (6-103) | 6% |
| 5-HGB(F,F)-F | (6-103) | 7% |
| 2-H2GB(F,F)-F | (6-106) | 6% |
| 3-H2GB(F,F)-F | (6-106) | 6% |
| 5-GHB(F,F)-F | (6-109) | 9% |

The following compound (1-2-1) was added to the above composition in a ratio of 0.12%.

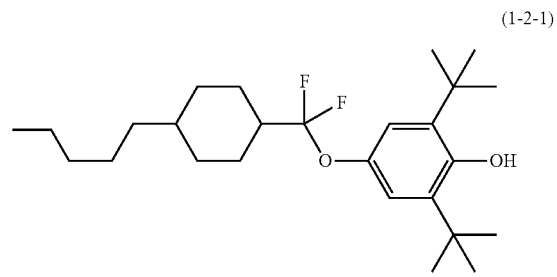 [SMILES: CCCCCC1CCC(C(F)(F)Oc2cc(C(C)(C)C)c(O)c(C(C)(C)C)c2)CC1]

(1-2-1)

NI=80.4° C.; η=22.4 mPa·s; Δn=0.064; and Δ∈=6.7.

Use Example 11

| | | |
|---|---|---|
| 3-HB-O1 | (2-5) | 15% |
| 3-HH-4 | (2-1) | 6% |
| 3-HB(2F,3F)-O2 | (9-1) | 10% |
| 5-HB(2F,3F)-O2 | (9-1) | 10% |
| 2-HHB(2F,3F)-1 | (10-1) | 13% |
| 3-HHB(2F,3F)-1 | (10-1) | 13% |
| 3-HHB(2F,3F)-O2 | (10-1) | 14% |
| 5-HHB(2F,3F)-O2 | (10-1) | 15% |
| 3-HHB-1 | (3-1) | 4% |

The following compound (1-3-1) was added to the above composition in a ratio of 0.12%.

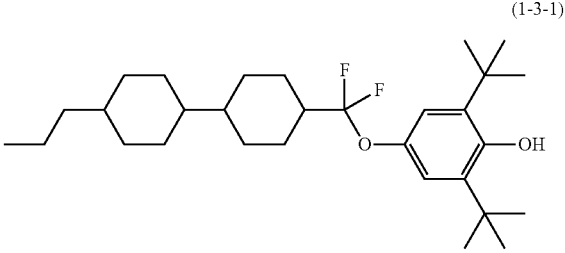 [SMILES: CCCC1CCC(C2CCC(C(F)(F)Oc3cc(C(C)(C)C)c(O)c(C(C)(C)C)c3)CC2)CC1]

(1-3-1)

NI=90.5° C.; η=35.7 mPa·s; Δn=0.090; and Δ∈=−3.4.

Use Example 12

| | | |
|---|---|---|
| 2-HH-5 | (2-1) | 5% |
| 3-HH-4 | (2-1) | 15% |
| 3-HH-5 | (2-1) | 4% |
| 3-HB-O2 | (2-5) | 10% |
| 3-H2B(2F,3F)-O2 | (9-4) | 13% |
| 5-H2B(2F,3F)-O2 | (9-4) | 14% |
| 3-HHB(2F,3CL)-O2 | (10-12) | 5% |
| 2-HBB(2F,3F)-O2 | (10-7) | 4% |
| 3-HBB(2F,3F)-O2 | (10-7) | 10% |
| 5-HBB(2F,3F)-O2 | (10-7) | 10% |
| 3-HHB-1 | (3-1) | 3% |
| 3-HHB-3 | (3-1) | 4% |
| 3-HHB-O1 | (3-1) | 3% |

The following compound (1-2-16) was added to the above composition in a ratio of 0.1%.

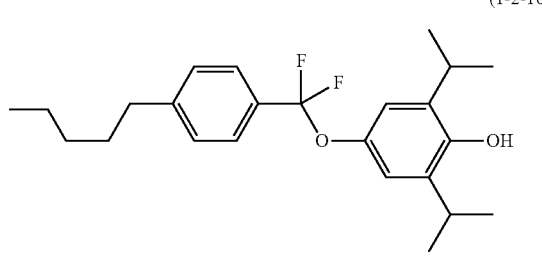

(1-2-16)

NI=79.9° C.; η=19.9 mPa·s; Δn=0.095; and Δ∈=−4.0.

Use Example 13

| | | |
|---|---|---|
| 2-HH-3 | (2-1) | 20% |
| 3-HH-4 | (2-1) | 8% |
| 1-BB-3 | (2-8) | 8% |
| 3-HB-O2 | (2-5) | 4% |
| 3-BB(2F,3F)-O2 | (9-3) | 9% |
| 5-BB(2F,3F)-O2 | (9-3) | 7% |
| 2-HH1OB(2F,3F)-O2 | (10-5) | 15% |
| 3-HH1OB(2F,3F)-O2 | (10-5) | 18% |
| 3-HHB-1 | (3-1) | 5% |
| 3-HHB-O1 | (3-1) | 3% |
| 5-B(F)BB-2 | (3-8) | 3% |

The following compound (1-2-1) was added to the above composition in a ratio of 0.07%.

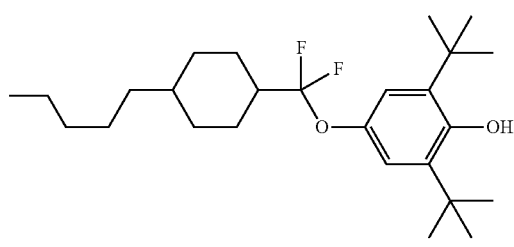

(1-2-1)

NI=73.6° C.; η=15.9 mPa·s; Δn=0.100; and Δ∈=−3.2.

Use Example 14

| | | |
|---|---|---|
| 2-HH-3 | (2-1) | 20% |
| 7-HB-1 | (2-5) | 8% |
| 5-HB-O2 | (2-5) | 8% |
| 3-HB(2F,3F)-O2 | (9-1) | 16% |
| 5-HB(2F,3F)-O2 | (9-1) | 15% |
| 3-HHB(2F,3CL)-O2 | (10-12) | 3% |
| 4-HHB(2F,3CL)-O2 | (10-12) | 3% |
| 5-HHB(2F,3CL)-O2 | (10-12) | 3% |
| 3-HH1OCRo(7F,8F)-5 | (13-6) | 5% |
| 5-HBB(F)B-2 | (4-5) | 10% |
| 5-HBB(F)B-3 | (4-5) | 9% |

The following compound (1-3-1) was added to the above composition in a ratio of 0.09%.

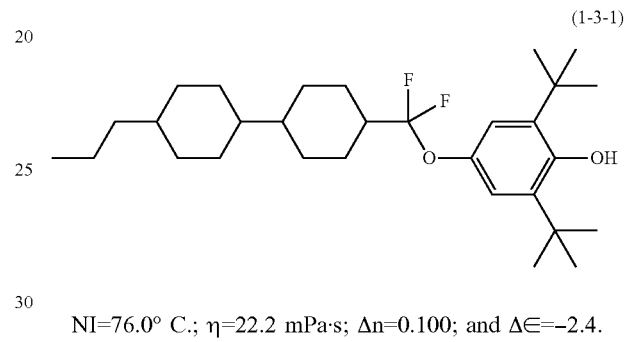

(1-3-1)

NI=76.0° C.; η=22.2 mPa·s; Δn=0.100; and Δ∈=−2.4.

Use Example 15

| | | |
|---|---|---|
| 1-BB-3 | (2-8) | 12% |
| 3-HH-V | (2-1) | 27% |
| 3-BB(2F,3F)-O2 | (9-3) | 12% |
| 2-HH1OB(2F,3F)-O2 | (10-5) | 13% |
| 3-HH1OB(2F,3F)-O2 | (10-5) | 22% |
| 3-HHB-1 | (3-1) | 7% |
| 5-B(F)BB-2 | (3-8) | 7% |

The following compound (1-2-16) was added to the above composition in a ratio of 0.05%.

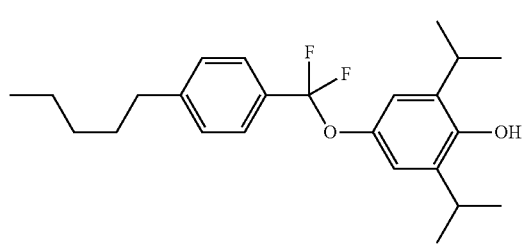

(1-2-16)

NI=76.1° C.; η=14.8 mPa·s; Δn=0.110; and Δ∈=−3.0.

Use Example 16

| | | |
|---|---|---|
| 2-HH-3 | (2-1) | 6% |
| 3-HH-V1 | (2-1) | 10% |

| | | |
|---|---|---|
| 1 V2-HH-1 | (2-1) | 8% |
| 1 V2-HH-3 | (2-1) | 7% |
| 3-BB(2F,3F)-O2 | (9-3) | 8% |
| 5-BB(2F,3F)-O2 | (9-3) | 4% |
| 3-H1OB(2F,3F)-O2 | (9-5) | 7% |
| 2-HH1OB(2F,3F)-O2 | (10-5) | 9% |
| 3-HH1OB(2F,3F)-O2 | (10-5) | 17% |
| 3-HDhB(2F,3F)-O2 | (10-3) | 8% |
| 3-HHB-1 | (3-1) | 4% |
| 3-HHB-3 | (3-1) | 3% |
| 2-BB(2F,3F)B-3 | (11-1) | 9% |

The following compound (1-2-1) was added to the above composition in a ratio of 0.1%.

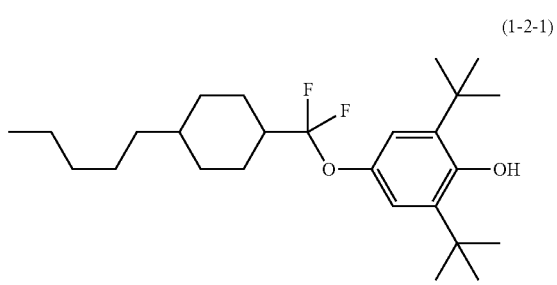 [SMILES: CCCCCC1CCC(C(F)(F)Oc2cc(C(C)(C)C)c(O)c(C(C)(C)C)c2)CC1]

(1-2-1)

NI=85.7 η=21.2 mPa·s; Δn=0.105; and Δ∈=−4.4.

Use Example 17

| | | |
|---|---|---|
| 1 V2-BEB(F,F)-C | (8-15) | 6% |
| 3-HB-C | (8-1) | 18% |
| 2-BTB-1 | (2-10) | 10% |
| 5-HH-VFF | (2-1) | 30% |
| 3-HHB-1 | (3-1) | 4% |
| VFF-HHB-1 | (3-1) | 8% |
| VFF2-HHB-1 | (3-1) | 9% |
| 3-H2BTB-2 | (3-17) | 5% |
| 3-H2BTB-3 | (3-17) | 5% |
| 3-H2BTB-4 | (3-17) | 5% |

The following compound (1-3-1) was added to the above composition in a ratio of 0.1%.

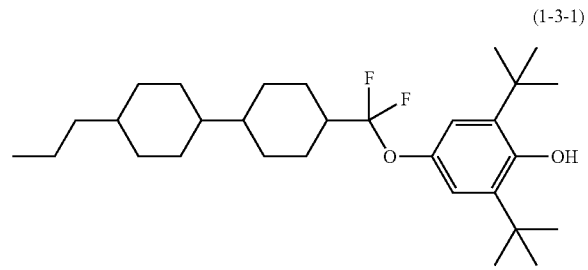 [SMILES: CCCC1CCC(C2CCC(C(F)(F)Oc3cc(C(C)(C)C)c(O)c(C(C)(C)C)c3)CC2)CC1]

(1-3-1)

NI=81.8° C.; η=11.8 mPa·s; Δn=0.132; and Δ∈=6.5.

Use Example 18

| | | |
|---|---|---|
| 5-HB(F)B(F,F)XB(F,F)-F | (7-41) | 4% |
| 3-BB(F)B(F,F)XB(F,F)-F | (7-47) | 4% |
| 4-BB(F)B(F,F)XB(F,F)-F | (7-47) | 5% |
| 5-BB(F)B(F,F)XB(F,F)-F | (7-47) | 5% |
| 3-HH-V | (2-1) | 41% |
| 3-HH-V1 | (2-1) | 7% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1 V2-BB-F | (5-1) | 3% |
| 3-BB(F,F)XB(F,F)-F | (6-97) | 11% |
| 3-HHBB(F,F)-F | (7-6) | 3% |

The following compound (1-2-16) was added to the above composition in a ratio of 0.1%.

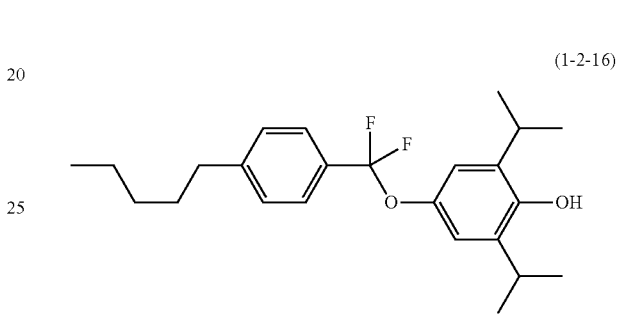

(1-2-16)

NI=82.0° C.; η=12.1 mPa·s; Δn=0.106; and Δ∈6.4.

Use Example 19

| | | |
|---|---|---|
| 3-GB(F)B(F,F)XB(F,F)-F | (7-53) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 41% |
| 3-HH-V1 | (2-1) | 6% |
| 3-HHEH-5 | (3-13) | 4% |
| 3-HHB-1 | (3-1) | 4% |
| V-HHB-1 | (3-1) | 5% |
| V2-BB(F)B-1 | (3-6) | 5% |
| 1 V2-BB-F | (5-1) | 3% |
| 3-BB(F,F)XB(F,F)-F | (6-97) | 5% |
| 3-GB(F,F)XB(F,F)-F | (6-113) | 4% |
| 3-HHBB(F,F)-F | (7-6) | 5% |

The following compound (1-2-1) was added to the above composition in a ratio of 0.12%.

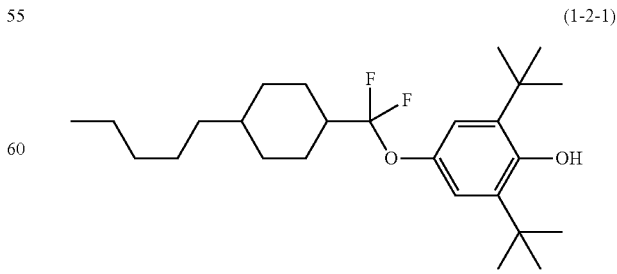

(1-2-1)

NI=86.0° C.; η=14.1 mPa·s; Δn=0.104; and Δ∈=7.0.

Use Example 20

| | | |
|---|---|---|
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 41% |
| 3-HH-V1 | (2-1) | 7% |
| 3-HHB-1 | (3-1) | 4% |
| V-HHB-1 | (3-1) | 5% |
| V2-HHB-1 | (3-1) | 3% |
| V2-BB(F)B-1 | (3-6) | 5% |
| 1 V2-BB-F | (5-1) | 3% |
| 3-BB(F,F)XB(F,F)-F | (6-97) | 11% |
| 3-HHBB(F,F)-F | (7-6) | 3% |

The following compound (1-2-15) was added to the above composition in a ratio of 0.15%.

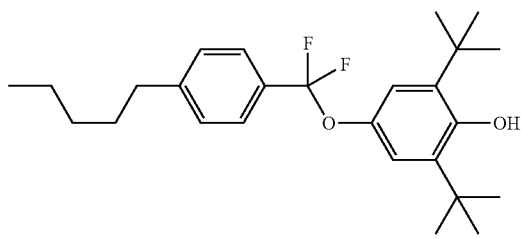

(1-2-15)

NI=82.0° C.; η=10.9 mPa·s; Δn=0.107; and Δ∈=6.4.

Use Example 21

| | | |
|---|---|---|
| 3-GB(F)B(F,F)XB(F,F)-F | (7-53) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 41% |
| 3-HH-V1 | (2-1) | 7% |
| 3-HHB-1 | (3-1) | 4% |
| V-HHB-1 | (3-1) | 5% |
| V2-HHB-1 | (3-1) | 3% |
| V2-BB(F)B-1 | (3-6) | 5% |
| 1 V2-BB-F | (5-1) | 3% |
| 3-HHXB(F,F)-F | (6-100) | 5% |
| 3-BB(F,F)XB(F,F)-F | (6-97) | 6% |
| 3-HHBB(F,F)-F | (7-6) | 3% |

The following compound (1-3-34) was added to the above composition in a ratio of 0.1%.

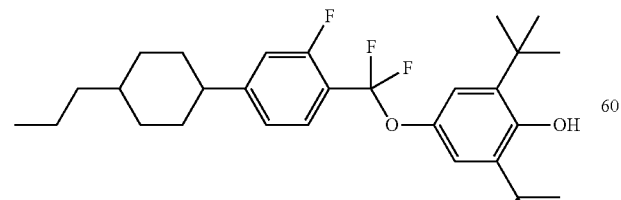

(1-3-34)

NI=86.3° C.; η=11.2 mPa·s; Δn=0.105; and Δ∈=6.6.

INDUSTRIAL APPLICABILITY

The compound of the invention is useful as an antioxidant. The liquid crystal composition containing the compound satisfies at least one of characteristics such as high maximum temperature, low minimum temperature, small viscosity, suitable optical anisotropy, large positive or negative dielectric anisotropy, large specific resistance, high stability to ultraviolet light, high stability to heat, and a large elastic constant, etc., or achieves a suitable balance between at least two of the above characteristics. The liquid crystal display device containing the composition has characteristics such as short response time, a large voltage holding ratio, a low threshold voltage, a large contrast ratio, and long service life, etc., and can thus be used in liquid crystal projectors and liquid crystal TVs, etc.

What is claimed is:

1. A compound represented by formula (1),

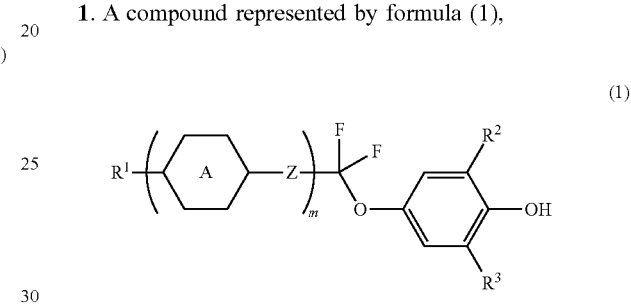

(1)

wherein in formula (1), $R^1$ is alkyl having 1 to 5 carbons; $R^2$ and $R^3$ are t-butyl; ring A is 1,4-cyclohexylene; Z is a single bond; and m is 2.

2. The compound of claim 1, wherein in formula (1), $R^1$ is alkyl having 3 to 5 carbons.

3. A liquid crystal composition, containing the compound of claim 1.

4. The liquid crystal composition of claim 3, further containing at least one compound selected from the group consisting of compounds represented by formulae (2) to (4),

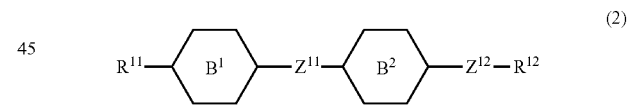

(2)

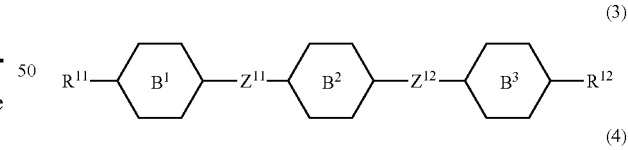

(3)

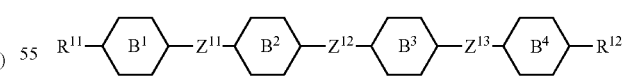

(4)

wherein in formulae (2) to (4),
$R^{11}$ and $R^{12}$ are independently alkyl having 1 to 10 carbons or alkenyl having 2 to 10 carbons, wherein at least one —CH$_2$— in the alkyl or alkenyl is optionally replaced with —O—, and at least one hydrogen in the alkyl or alkenyl is optionally replaced with fluorine;
ring $B^1$, ring $B^2$, ring $B^3$, and ring $B^4$ are independently 1,4-cyclohexylene, 1,4-phenylene, 2-fluoro-1,4-phenylene, 2,5-difluoro-1,4-phenylene, or pyrimidine-2,5-diyl; and $Z^{11}$, $Z^{12}$, and $Z^{13}$ are independently a single bond, —CH$_2$CH$_2$—, —CH=CH—, —C≡C—, or —COO—.

5. The liquid crystal composition of claim 3, further containing at least one compound selected from the group consisting of compounds represented by formulae (5) to (7),

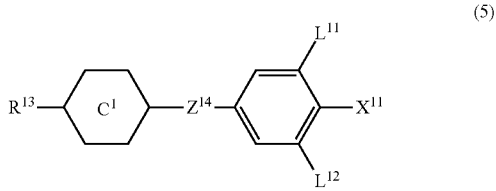
(5)

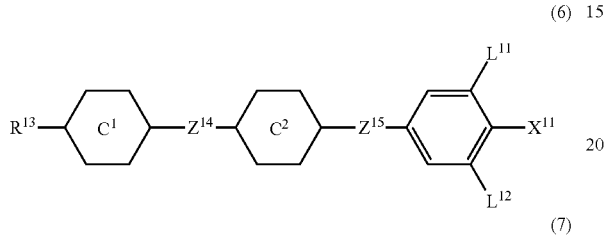
(6)

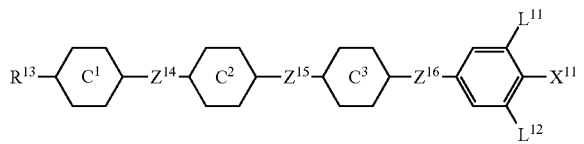
(7)

wherein in formulae (5) to (7),
$R^{13}$ is alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine;
$X^{11}$ is fluorine, chlorine, —OCF$_3$, —CF$_3$, —CHF$_2$, —CH$_2$F, —OCF$_2$CHF$_2$, or —OCF$_2$CHFCF$_3$;
ring $C^1$, ring $C^2$ and ring $C^3$ are independently 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl;
$Z^{14}$, $Z^{15}$, and $Z^{16}$ are independently a single bond, —CH$_2$CH$_2$—, —CH=CH—, —COO—, —CF$_2$O—, —OCF$_2$—, —CH$_2$O—, or —(CH$_2$)$_4$—; and
$L^{11}$ and $L^{12}$ are independently hydrogen or fluorine.

6. The liquid crystal composition of claim 3, further containing at least one compound represented by formula (8),

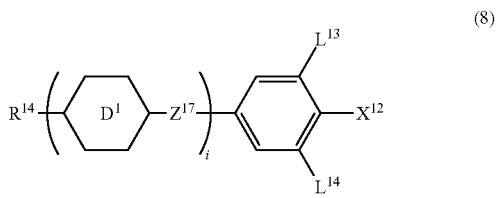
(8)

wherein in formula (8),
$R^{14}$ is alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine;
$X^{12}$ is —C≡N or —C≡C—C≡N;
ring $D^1$ is 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl;
$Z^{17}$ is a single bond, —CH$_2$CH$_2$—, —COO—, —CF$_2$O—, —OCF$_2$—, or —CH$_2$O—;
$L^{13}$ and $L^{14}$ are independently hydrogen or fluorine; and
i is 1, 2, 3, or 4.

7. The liquid crystal composition of claim 3, further containing at least one compound selected from the group consisting of compounds represented by formulae (9) to (15),

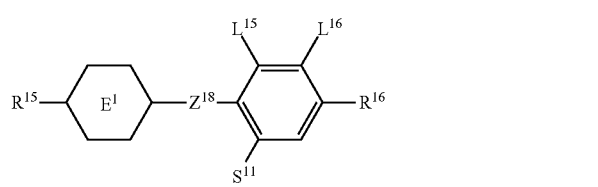
(9)

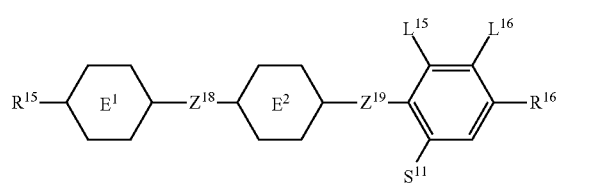
(10)

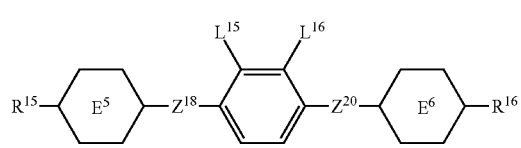
(11)

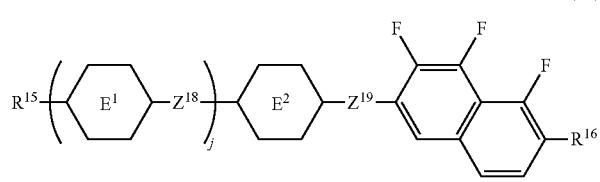
(12)

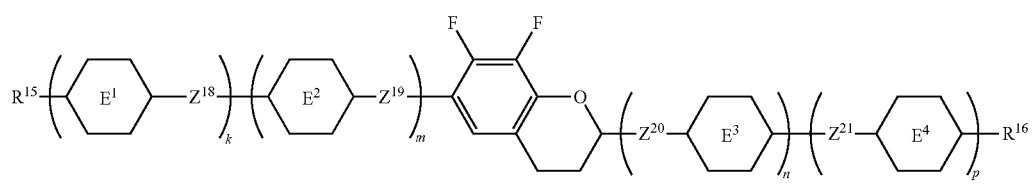
(13)

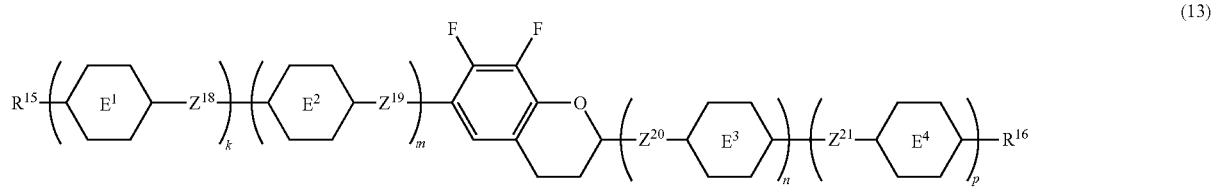

-continued

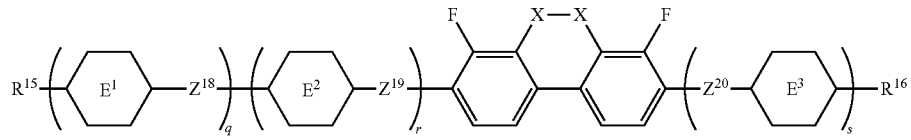
(14)

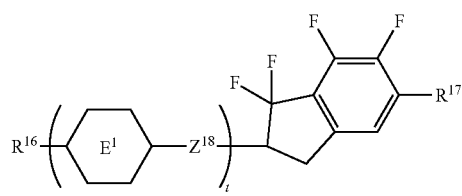
(15)

wherein in formulae (9) to (15), $R^{15}$ and $R^{16}$ are independently alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine;

$R^{17}$ is hydrogen, fluorine, alkyl having 1 to 10 carbons, or alkenyl having 2 to 10 carbons, wherein at least one —$CH_2$— in the alkyl and alkenyl is optionally replaced with —O—, and at least one hydrogen in the alkyl and alkenyl is optionally replaced with fluorine;

ring $E^1$, ring $E^2$, ring $E^3$, and ring $E^4$ are independently 1,4-cyclohexylene, 1,4-cyclohexenylene, 1,4-phenylene in which at least one hydrogen is optionally replaced with fluorine, tetrahydropyran-2,5-diyl, or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl, or decahydronaphthalene-2,6-diyl;

$Z^{18}$, $Z^{19}$, $Z^{20}$, and $Z^{21}$ are independently a single bond, —$CH_2CH_2$—, —COO—, —$CH_2O$—, —$OCF_2$—, or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, the sum of k, m, n and p is 1 or 2, the sum of q, r and s is 0, 1, 2, or 3, and t is 1, 2, or 3.

8. A method for stabilizing a liquid crystal composition by adding the compound of claim 1.

9. A liquid crystal display device, containing the liquid crystal composition of claim 3.

10. The liquid crystal display device of claim 9, wherein an operating mode of the liquid crystal display device comprises a TN mode, an ECB mode, an OCB mode, a VA mode, an IPS mode, a PSA mode, an FFS mode, or an FPA mode, and a driving method for the liquid crystal display device comprises an active matrix method.

* * * * *